United States Patent
Willis et al.

(10) Patent No.: US 10,624,695 B2
(45) Date of Patent: Apr. 21, 2020

(54) VISUAL ELECTRODE ABLATION SYSTEMS

(71) Applicant: INTUITIVE SURGICAL OPERATIONS, INC., Sunnyvale, CA (US)

(72) Inventors: N. Parker Willis, Atherton, CA (US); Zachary J. Malchano, San Francisco, CA (US); Chris A. Rothe, San Mateo, CA (US); Vahid Saadat, Atherton, CA (US); Ruey-Feng Peh, Singapore (SG); David Miller, Boulder, CO (US); Edmund A. Tam, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 230 days.

(21) Appl. No.: 14/226,151

(22) Filed: Mar. 26, 2014

(65) Prior Publication Data
US 2014/0316406 A1 Oct. 23, 2014

Related U.S. Application Data

(62) Division of application No. 12/118,439, filed on May 9, 2008, now Pat. No. 8,709,008.
(Continued)

(51) Int. Cl.
*A61B 18/12* (2006.01)
*A61B 18/14* (2006.01)
(Continued)

(52) U.S. Cl.
CPC ...... *A61B 18/1492* (2013.01); *A61B 1/00089* (2013.01); *A61B 1/012* (2013.01);
(Continued)

(58) Field of Classification Search
CPC .......... A61B 2018/00809; A61B 2018/00839; A61B 2018/1472; A61B 2018/00214;
(Continued)

(56) References Cited

U.S. PATENT DOCUMENTS

| 623,022 A | 4/1899 | Johnson |
|---|---|---|
| 2,305,462 A | 12/1942 | Wolf |

(Continued)

FOREIGN PATENT DOCUMENTS

| DE | 10028155 A1 | 12/2000 |
|---|---|---|
| EP | 0283661 A2 | 9/1988 |

(Continued)

OTHER PUBLICATIONS

Avitall B., et al., "Right-Sided Driven Atrial Fibrillation in a Sterile Pericarditis Dog Model," Pacing and Clinical Electrophysiology, 1994, vol. 17, pp. 774.
(Continued)

*Primary Examiner* — Daniel W Fowler
(74) *Attorney, Agent, or Firm* — Haynes and Boone, LLP

(57) ABSTRACT

A method of ablating a tissue region within a blood-filled environment comprises restraining a fluid within a visualization field in a portion of the blood-filled environment and visualizing the tissue region through the fluid within the visualization field. The method also includes transmitting ablating electrical energy from the fluid into the visualized tissue region.

16 Claims, 52 Drawing Sheets

Related U.S. Application Data

(60) Provisional application No. 60/917,487, filed on May 11, 2007.

(51) Int. Cl.
*A61B 1/00* (2006.01)
*A61B 1/012* (2006.01)
*A61B 17/00* (2006.01)
*A61B 18/00* (2006.01)

(52) U.S. Cl.
CPC .............. *A61B 2017/00106* (2013.01); *A61B 2018/00214* (2013.01); *A61B 2018/00577* (2013.01); *A61B 2018/00642* (2013.01); *A61B 2018/00809* (2013.01); *A61B 2018/00839* (2013.01); *A61B 2018/1472* (2013.01); *A61B 2218/002* (2013.01)

(58) Field of Classification Search
CPC ........... A61B 2018/00577; A61B 2018/00642; A61B 2218/002; A61B 18/1492; A61B 1/00089; A61B 1/012; A61B 2017/00106
See application file for complete search history.

(56) References Cited

U.S. PATENT DOCUMENTS

| | | |
|---|---|---|
| 2,453,862 A | 11/1948 | Salisbury |
| 3,559,651 A | 2/1971 | Moss |
| 3,874,388 A | 4/1975 | King et al. |
| 4,175,545 A | 11/1979 | Termanini |
| 4,326,529 A | 4/1982 | Doss et al. |
| 4,445,892 A | 5/1984 | Hussein et al. |
| 4,470,407 A | 9/1984 | Hussein |
| 4,517,976 A | 5/1985 | Murakoshi et al. |
| 4,569,335 A | 2/1986 | Tsuno |
| 4,576,146 A | 3/1986 | Kawazoe et al. |
| 4,615,333 A | 10/1986 | Taguchi |
| 4,619,247 A | 10/1986 | Inoue et al. |
| 4,676,258 A | 6/1987 | Inokuchi et al. |
| 4,681,093 A | 7/1987 | Ono et al. |
| 4,709,698 A | 12/1987 | Johnston et al. |
| 4,710,192 A | 12/1987 | Liotta et al. |
| 4,727,418 A | 2/1988 | Kato et al. |
| 4,784,133 A | 11/1988 | Mackin |
| 4,848,323 A | 7/1989 | Marijnissen et al. |
| 4,911,148 A | 3/1990 | Sosnowski et al. |
| 4,914,521 A | 4/1990 | Adair |
| 4,943,290 A | 7/1990 | Rexroth et al. |
| 4,950,285 A | 8/1990 | Wilk |
| 4,957,484 A | 9/1990 | Murtfeldt |
| 4,961,738 A | 10/1990 | Mackin |
| 4,976,710 A | 12/1990 | Mackin |
| 4,991,578 A | 2/1991 | Cohen |
| 4,994,069 A | 2/1991 | Ritchart et al. |
| 4,998,916 A | 3/1991 | Hammerslag et al. |
| 4,998,972 A | 3/1991 | Chin et al. |
| 5,047,028 A | 9/1991 | Qian |
| 5,057,106 A | 10/1991 | Kasevich et al. |
| 5,090,959 A | 2/1992 | Samson et al. |
| 5,123,428 A | 6/1992 | Schwarz |
| RE34,002 E | 7/1992 | Adair |
| 5,156,141 A | 10/1992 | Krebs et al. |
| 5,171,259 A | 12/1992 | Inoue |
| 5,281,238 A | 1/1994 | Chin et al. |
| 5,282,827 A | 2/1994 | Kensey et al. |
| 5,306,234 A | 4/1994 | Johnson |
| 5,313,943 A | 5/1994 | Houser et al. |
| 5,330,496 A | 7/1994 | Alferness |
| 5,334,159 A | 8/1994 | Turkel |
| 5,334,193 A | 8/1994 | Nardella |
| 5,336,252 A | 8/1994 | Cohen |
| 5,339,800 A | 8/1994 | Wiita et al. |
| 5,348,554 A | 9/1994 | Imran et al. |
| 5,353,792 A | 10/1994 | Luebbers et al. |
| 5,370,647 A | 12/1994 | Graber et al. |
| 5,373,840 A | 12/1994 | Knighton |
| 5,375,612 A | 12/1994 | Cottenceau et al. |
| 5,385,148 A | 1/1995 | Lesh et al. |
| 5,391,182 A | 2/1995 | Chin |
| 5,403,326 A | 4/1995 | Harrison et al. |
| 5,405,376 A | 4/1995 | Mulier et al. |
| 5,421,338 A | 6/1995 | Crowley et al. |
| 5,431,649 A | 7/1995 | Mulier et al. |
| 5,453,785 A | 9/1995 | Lenhardt et al. |
| 5,462,521 A | 10/1995 | Brucker et al. |
| 5,471,515 A | 11/1995 | Fossum et al. |
| 5,498,230 A | 3/1996 | Adair |
| 5,505,730 A | 4/1996 | Edwards |
| 5,515,853 A | 5/1996 | Smith et al. |
| 5,527,338 A | 6/1996 | Purdy |
| 5,549,603 A | 8/1996 | Feiring |
| 5,558,619 A | 9/1996 | Kami et al. |
| 5,571,088 A | 11/1996 | Lennox et al. |
| 5,575,756 A | 11/1996 | Karasawa et al. |
| 5,575,810 A | 11/1996 | Swanson et al. |
| 5,584,872 A | 12/1996 | LaFontaine et al. |
| 5,591,119 A | 1/1997 | Adair |
| 5,593,422 A | 1/1997 | Muijs Van De Moer et al. |
| 5,593,424 A | 1/1997 | Northrup, III |
| 5,606,975 A * | 3/1997 | Liang .................. A61B 8/12 600/437 |
| 5,672,153 A | 9/1997 | Lax et al. |
| 5,676,693 A | 10/1997 | LaFontaine |
| 5,681,308 A | 10/1997 | Edwards et al. |
| 5,695,448 A | 12/1997 | Kimura et al. |
| 5,697,281 A | 12/1997 | Eggers et al. |
| 5,697,882 A | 12/1997 | Eggers et al. |
| 5,709,224 A | 1/1998 | Behl et al. |
| 5,713,907 A | 2/1998 | Hogendijk et al. |
| 5,713,946 A | 2/1998 | Ben-Haim |
| 5,716,321 A | 2/1998 | Kerin et al. |
| 5,722,403 A * | 3/1998 | McGee .................. A61N 1/44 600/373 |
| 5,725,523 A | 3/1998 | Mueller |
| 5,746,747 A | 5/1998 | McKeating |
| 5,749,846 A | 5/1998 | Edwards et al. |
| 5,749,890 A | 5/1998 | Shaknovich |
| 5,754,313 A | 5/1998 | Pelchy et al. |
| 5,766,137 A | 6/1998 | Omata |
| 5,769,846 A | 6/1998 | Edwards et al. |
| 5,792,045 A | 8/1998 | Adair |
| 5,797,903 A | 8/1998 | Swanson et al. |
| 5,823,947 A | 10/1998 | Yoon et al. |
| 5,827,268 A | 10/1998 | Laufer |
| 5,829,447 A | 11/1998 | Stevens et al. |
| 5,842,973 A | 12/1998 | Bullard |
| 5,843,118 A | 12/1998 | Sepetka et al. |
| 5,848,969 A | 12/1998 | Panescu et al. |
| 5,860,974 A * | 1/1999 | Abele .................. A61B 8/12 600/374 |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | LaFontaine et al. |
| 5,904,651 A | 5/1999 | Swanson et al. |
| 5,908,445 A | 6/1999 | Whayne et al. |
| 5,925,038 A | 7/1999 | Panescu et al. |
| 5,928,250 A | 7/1999 | Koike et al. |
| 5,929,901 A | 7/1999 | Adair et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,986,693 A | 11/1999 | Adair et al. |
| 5,997,571 A | 12/1999 | Farr et al. |
| 6,004,269 A | 12/1999 | Crowley et al. |
| 6,012,457 A | 1/2000 | Lesh |
| 6,024,740 A | 2/2000 | Lesh et al. |

(56) References Cited

U.S. PATENT DOCUMENTS

| | | |
|---|---|---|
| 6,027,501 A | 2/2000 | Goble et al. |
| 6,036,685 A | 3/2000 | Mueller |
| 6,043,839 A | 3/2000 | Adair et al. |
| 6,047,218 A | 4/2000 | Whayne et al. |
| 6,063,077 A | 5/2000 | Schaer |
| 6,063,081 A | 5/2000 | Mulier et al. |
| 6,068,653 A | 5/2000 | LaFontaine |
| 6,071,279 A | 6/2000 | Whayne et al. |
| 6,071,302 A | 6/2000 | Sinofsky et al. |
| 6,081,740 A | 6/2000 | Gombrich et al. |
| 6,086,528 A | 7/2000 | Adair |
| 6,086,534 A | 7/2000 | Kesten |
| 6,099,498 A | 8/2000 | Addis |
| 6,099,514 A | 8/2000 | Sharkey et al. |
| 6,102,905 A | 8/2000 | Baxter et al. |
| 6,112,123 A | 8/2000 | Kelleher et al. |
| 6,115,626 A | 9/2000 | Whayne et al. |
| 6,123,703 A | 9/2000 | Tu et al. |
| 6,123,718 A | 9/2000 | Tu et al. |
| 6,129,724 A | 10/2000 | Fleischman et al. |
| 6,139,508 A | 10/2000 | Simpson et al. |
| 6,142,993 A | 11/2000 | Whayne et al. |
| 6,152,144 A | 11/2000 | Lesh et al. |
| 6,156,350 A | 12/2000 | Constantz |
| 6,159,203 A | 12/2000 | Sinofsky |
| 6,161,543 A | 12/2000 | Cox et al. |
| 6,164,283 A | 12/2000 | Lesh |
| 6,167,297 A | 12/2000 | Benaron |
| 6,168,591 B1 | 1/2001 | Sinofsky |
| 6,168,594 B1 | 1/2001 | LaFontaine et al. |
| 6,174,307 B1 | 1/2001 | Daniel et al. |
| 6,178,346 B1 | 1/2001 | Amundson et al. |
| 6,190,381 B1 | 2/2001 | Olsen et al. |
| 6,211,904 B1 | 4/2001 | Adair et al. |
| 6,224,553 B1 | 5/2001 | Nevo |
| 6,231,561 B1 | 5/2001 | Frazier et al. |
| 6,235,044 B1 | 5/2001 | Root et al. |
| 6,237,605 B1 | 5/2001 | Vaska et al. |
| 6,238,393 B1 | 5/2001 | Mulier et al. |
| 6,240,312 B1 | 5/2001 | Alfano et al. |
| 6,254,598 B1 | 7/2001 | Edwards et al. |
| 6,258,083 B1 | 7/2001 | Daniel et al. |
| 6,263,224 B1 | 7/2001 | West |
| 6,270,492 B1 | 8/2001 | Sinofsky |
| 6,275,255 B1 | 8/2001 | Adair et al. |
| 6,290,689 B1 | 9/2001 | Delaney et al. |
| 6,306,081 B1 | 10/2001 | Ishikawa et al. |
| 6,310,642 B1 | 10/2001 | Adair et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,777 B1 | 11/2001 | Comben |
| 6,315,778 B1 | 11/2001 | Gambale et al. |
| 6,322,536 B1 | 11/2001 | Rosengart et al. |
| 6,325,797 B1 | 12/2001 | Stewart et al. |
| 6,328,727 B1 | 12/2001 | Frazier et al. |
| 6,358,247 B1 | 3/2002 | Altman et al. |
| 6,358,248 B1 | 3/2002 | Mulier et al. |
| 6,375,654 B1 | 4/2002 | McIntyre |
| 6,379,345 B1 | 4/2002 | Constantz |
| 6,385,476 B1 | 5/2002 | Osadchy et al. |
| 6,387,043 B1 | 5/2002 | Yoon |
| 6,387,071 B1 | 5/2002 | Constantz |
| 6,394,096 B1 | 5/2002 | Constantz |
| 6,396,873 B1 | 5/2002 | Goldstein et al. |
| 6,398,780 B1 | 6/2002 | Farley et al. |
| 6,401,719 B1 | 6/2002 | Farley et al. |
| 6,409,722 B1 | 6/2002 | Hoey et al. |
| 6,416,511 B1 | 7/2002 | Lesh et al. |
| 6,419,669 B1 | 7/2002 | Frazier et al. |
| 6,423,051 B1 | 7/2002 | Kaplan et al. |
| 6,423,055 B1 | 7/2002 | Farr et al. |
| 6,423,058 B1 | 7/2002 | Edwards et al. |
| 6,428,536 B2 | 8/2002 | Panescu et al. |
| 6,436,118 B1 | 8/2002 | Kayan |
| 6,440,061 B1 | 8/2002 | Wenner et al. |
| 6,440,119 B1 | 8/2002 | Nakada et al. |
| 6,458,151 B1 | 10/2002 | Saltiel |
| 6,464,697 B1 | 10/2002 | Edwards et al. |
| 6,474,340 B1 | 11/2002 | Vaska et al. |
| 6,475,223 B1 | 11/2002 | Werp et al. |
| 6,478,769 B1 | 11/2002 | Parker |
| 6,482,162 B1 | 11/2002 | Moore |
| 6,484,727 B1 | 11/2002 | Vaska et al. |
| 6,485,489 B2 | 11/2002 | Teirstein et al. |
| 6,488,671 B1 | 12/2002 | Constantz et al. |
| 6,494,902 B2 | 12/2002 | Hoey et al. |
| 6,497,705 B2 | 12/2002 | Comben |
| 6,500,174 B1 | 12/2002 | Maguire et al. |
| 6,502,576 B1 | 1/2003 | Lesh |
| 6,514,249 B1 | 2/2003 | Maguire et al. |
| 6,517,533 B1 | 2/2003 | Swaminathan |
| 6,517,534 B1 * | 2/2003 | McGovern ......... A61B 18/1485 606/28 |
| 6,527,979 B2 | 3/2003 | Constantz et al. |
| 6,532,380 B1 | 3/2003 | Close et al. |
| 6,533,767 B2 | 3/2003 | Johansson et al. |
| 6,537,272 B2 | 3/2003 | Christopherson et al. |
| 6,540,733 B2 | 4/2003 | Constantz et al. |
| 6,540,744 B2 | 4/2003 | Hassett et al. |
| 6,544,195 B2 | 4/2003 | Wilson et al. |
| 6,547,780 B1 | 4/2003 | Sinofsky |
| 6,558,375 B1 | 5/2003 | Sinofsky et al. |
| 6,558,382 B2 | 5/2003 | Jahns et al. |
| 6,562,020 B1 | 5/2003 | Constantz et al. |
| 6,572,609 B1 | 6/2003 | Farr et al. |
| 6,579,285 B2 | 6/2003 | Sinofsky |
| 6,585,732 B2 | 7/2003 | Mulier et al. |
| 6,587,709 B2 | 7/2003 | Solf et al. |
| 6,593,884 B1 | 7/2003 | Gilboa et al. |
| 6,605,055 B1 | 8/2003 | Sinofsky et al. |
| 6,613,062 B1 | 9/2003 | Leckrone et al. |
| 6,622,732 B2 | 9/2003 | Constantz |
| 6,626,855 B1 | 9/2003 | Weng et al. |
| 6,626,900 B1 | 9/2003 | Sinofsky et al. |
| 6,635,070 B2 | 10/2003 | Leeflang et al. |
| 6,645,202 B1 | 11/2003 | Pless et al. |
| 6,650,923 B1 | 11/2003 | Lesh et al. |
| 6,658,279 B2 | 12/2003 | Swanson et al. |
| 6,659,940 B2 | 12/2003 | Adler |
| 6,673,090 B2 | 1/2004 | Root et al. |
| 6,676,656 B2 | 1/2004 | Sinofsky |
| 6,679,836 B2 | 1/2004 | Couvillon, Jr. et al. |
| 6,682,526 B1 | 1/2004 | Jones et al. |
| 6,689,128 B2 | 2/2004 | Sliwa et al. |
| 6,692,430 B2 | 2/2004 | Adler |
| 6,701,581 B2 | 3/2004 | Senovich et al. |
| 6,701,931 B2 | 3/2004 | Sliwa et al. |
| 6,702,780 B1 | 3/2004 | Gilboa et al. |
| 6,704,043 B2 | 3/2004 | Goldstein et al. |
| 6,706,039 B2 | 3/2004 | Mulier et al. |
| 6,712,798 B2 | 3/2004 | Constantz |
| 6,719,747 B2 | 4/2004 | Constantz et al. |
| 6,719,755 B2 | 4/2004 | Sliwa et al. |
| 6,730,063 B2 | 5/2004 | Delaney et al. |
| 6,736,810 B2 | 5/2004 | Hoey et al. |
| 6,751,492 B2 | 6/2004 | Ben-Haim |
| 6,755,790 B2 | 6/2004 | Stewart et al. |
| 6,755,811 B1 | 6/2004 | Constantz |
| 6,764,487 B2 | 7/2004 | Mulier et al. |
| 6,771,996 B2 | 8/2004 | Bowe et al. |
| 6,773,402 B2 | 8/2004 | Govari et al. |
| 6,780,151 B2 | 8/2004 | Grabover et al. |
| 6,805,128 B1 | 10/2004 | Pless et al. |
| 6,805,129 B1 | 10/2004 | Pless et al. |
| 6,811,562 B1 | 11/2004 | Pless |
| 6,833,814 B2 | 12/2004 | Gilboa et al. |
| 6,840,923 B1 | 1/2005 | Lapcevic |
| 6,840,936 B2 | 1/2005 | Sliwa et al. |
| 6,849,073 B2 | 2/2005 | Hoey et al. |
| 6,858,005 B2 | 2/2005 | Ohline et al. |
| 6,858,026 B2 | 2/2005 | Sliwa et al. |
| 6,863,668 B2 | 3/2005 | Gillespie et al. |
| 6,866,651 B2 | 3/2005 | Constantz |

(56) References Cited

U.S. PATENT DOCUMENTS

| | | |
|---|---|---|
| 6,887,237 B2 | 5/2005 | McGaffigan |
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,916,284 B2 | 7/2005 | Moriyama |
| 6,923,805 B1 | 8/2005 | LaFontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,962,589 B2 | 11/2005 | Mulier et al. |
| 6,971,394 B2 | 12/2005 | Sliwa et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,019,610 B2 | 3/2006 | Creighton et al. |
| 7,025,746 B2 | 4/2006 | Tal |
| 7,030,904 B2 | 4/2006 | Adair et al. |
| 7,041,098 B2 | 5/2006 | Farley et al. |
| 7,042,487 B2 | 5/2006 | Nakashima |
| 7,044,135 B2 | 5/2006 | Lesh |
| 7,052,493 B2 | 5/2006 | Vaska et al. |
| 7,090,683 B2 | 8/2006 | Brock et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,186,214 B2 | 3/2007 | Ness |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,416,552 B2 | 8/2008 | Paul et al. |
| 7,435,248 B2 | 10/2008 | Taimisto et al. |
| 7,527,625 B2 | 5/2009 | Knight et al. |
| 7,534,204 B2 | 5/2009 | Starksen et al. |
| 7,569,052 B2 | 8/2009 | Phan et al. |
| 7,736,347 B2 | 6/2010 | Kaplan et al. |
| 7,758,499 B2 | 7/2010 | Adler |
| 7,860,555 B2 | 12/2010 | Saadat |
| 7,860,556 B2 | 12/2010 | Saadat |
| 8,131,350 B2 | 3/2012 | Saadat et al. |
| 8,137,333 B2 | 3/2012 | Saadat et al. |
| 8,709,008 B2 | 4/2014 | Willis et al. |
| 9,155,587 B2 | 10/2015 | Willis et al. |
| 2001/0020126 A1 | 9/2001 | Swanson et al. |
| 2001/0039416 A1 | 11/2001 | Moorman et al. |
| 2001/0047136 A1 | 11/2001 | Domanik et al. |
| 2001/0047184 A1 | 11/2001 | Connors |
| 2002/0004644 A1 | 1/2002 | Koblish |
| 2002/0026127 A1* | 2/2002 | Balbierz ............ A61B 18/1206 600/567 |
| 2002/0026145 A1 | 2/2002 | Bagaoisan et al. |
| 2002/0054852 A1 | 5/2002 | Cate |
| 2002/0065455 A1 | 5/2002 | Ben-Haim et al. |
| 2002/0087169 A1 | 7/2002 | Brock et al. |
| 2002/0091304 A1 | 7/2002 | Ogura et al. |
| 2002/0138088 A1 | 9/2002 | Nash et al. |
| 2002/0143326 A1 | 10/2002 | Foley et al. |
| 2002/0165598 A1 | 11/2002 | Wahr et al. |
| 2002/0169377 A1 | 11/2002 | Khairkhahan et al. |
| 2002/0188289 A1* | 12/2002 | Hegde ............ A61B 18/1492 606/41 |
| 2003/0009085 A1 | 1/2003 | Arai et al. |
| 2003/0035156 A1 | 2/2003 | Cooper |
| 2003/0036698 A1 | 2/2003 | Kohler et al. |
| 2003/0069572 A1* | 4/2003 | Wellman ............ A61B 18/1442 606/41 |
| 2003/0069593 A1 | 4/2003 | Tremulis et al. |
| 2003/0120142 A1 | 6/2003 | Dubuc et al. |
| 2003/0120268 A1* | 6/2003 | Bertolero ............ A61B 1/12 606/32 |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0208252 A1* | 11/2003 | O'Boyle ............ A61B 18/1492 607/122 |
| 2003/0212394 A1 | 11/2003 | Pearson et al. |
| 2003/0220574 A1 | 11/2003 | Markus et al. |
| 2003/0222325 A1 | 12/2003 | Jacobsen et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210239 A1 | 10/2004 | Nash et al. |
| 2004/0215180 A1 | 10/2004 | Starkebaum et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0249367 A1 | 12/2004 | Saadat et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0090818 A1 | 4/2005 | Pike et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0069303 A1 | 3/2006 | Couvillon, Jr. |
| 2006/0074398 A1 | 4/2006 | Whiting et al. |

(56) References Cited

U.S. PATENT DOCUMENTS

| | | |
|---|---|---|
| 2006/0074410 A1* | 4/2006 | Malecki ............ A61B 18/1492 606/32 |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0258909 A1 | 11/2006 | Saadat et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043351 A1* | 2/2007 | Fleischman ......... A61B 18/148 606/49 |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0265609 A1 | 11/2007 | Thapliyal et al. |
| 2007/0265610 A1 | 11/2007 | Thapliyal et al. |
| 2007/0270686 A1 | 11/2007 | Ritter et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015445 A1 | 1/2008 | Saadat et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033241 A1 | 2/2008 | Peh et al. |
| 2008/0057106 A1 | 3/2008 | Erickson et al. |
| 2008/0058590 A1 | 3/2008 | Saadat et al. |
| 2008/0058650 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0188759 A1 | 8/2008 | Saadat et al. |
| 2008/0214889 A1 | 9/2008 | Saadat et al. |
| 2008/0228032 A1 | 9/2008 | Starksen et al. |
| 2008/0275300 A1 | 11/2008 | Rothe et al. |
| 2008/0281293 A1 | 11/2008 | Peh et al. |
| 2008/0287790 A1 | 11/2008 | Li |
| 2008/0287805 A1 | 11/2008 | Li |
| 2009/0030276 A1 | 1/2009 | Saadat et al. |
| 2009/0054803 A1 | 2/2009 | Saadat et al. |
| 2009/0062790 A1 | 3/2009 | Malchano et al. |
| 2009/0076489 A1 | 3/2009 | Welches et al. |
| 2009/0076498 A1 | 3/2009 | Saadat et al. |
| 2009/0082623 A1 | 3/2009 | Rothe et al. |
| 2009/0125022 A1 | 5/2009 | Saadat et al. |
| 2009/0143640 A1 | 6/2009 | Saadat et al. |
| 2009/0187074 A1 | 7/2009 | Saadat et al. |
| 2009/0203962 A1 | 8/2009 | Miller et al. |
| 2009/0221871 A1 | 9/2009 | Peh et al. |
| 2009/0227999 A1 | 9/2009 | Willis et al. |
| 2009/0264727 A1 | 10/2009 | Markowitz et al. |
| 2009/0267773 A1 | 10/2009 | Markowitz et al. |
| 2009/0275799 A1 | 11/2009 | Saadat et al. |
| 2009/0299363 A1 | 12/2009 | Saadat et al. |
| 2009/0326572 A1 | 12/2009 | Peh et al. |
| 2010/0004506 A1 | 1/2010 | Saadat |
| 2010/0004633 A1 | 1/2010 | Rothe et al. |
| 2010/0004661 A1 | 1/2010 | Verin et al. |
| 2010/0010311 A1 | 1/2010 | Miller et al. |
| 2010/0094081 A1 | 4/2010 | Rothe et al. |
| 2010/0130836 A1 | 5/2010 | Malchano et al. |
| 2011/0060227 A1 | 3/2011 | Saadat |
| 2011/0060298 A1 | 3/2011 | Saadat |
| 2011/0144576 A1 | 6/2011 | Rothe et al. |
| 2012/0016221 A1 | 1/2012 | Saadat et al. |
| 2012/0059366 A1 | 3/2012 | Drews et al. |
| 2012/0150046 A1 | 6/2012 | Watson et al. |

FOREIGN PATENT DOCUMENTS

| | | |
|---|---|---|
| EP | 0301288 A1 | 2/1989 |
| JP | S5993413 A | 5/1984 |
| JP | S59181315 A | 10/1984 |
| JP | H01221133 A | 9/1989 |
| JP | H03284265 A | 12/1991 |
| JP | H05103746 A | 4/1993 |
| JP | H0951897 A | 2/1997 |
| JP | H1299725 A | 11/1999 |
| JP | 2001258822 A | 9/2001 |
| WO | WO-9221292 A2 | 12/1992 |
| WO | WO-9407413 A1 | 4/1994 |
| WO | WO-9503843 A1 | 2/1995 |
| WO | WO-9818388 A1 | 5/1998 |
| WO | WO-03039350 A2 | 5/2003 |
| WO | WO-03053491 A2 | 7/2003 |
| WO | WO-03101287 A2 | 12/2003 |
| WO | WO-2004043272 A1 | 5/2004 |
| WO | WO-2004080508 A2 | 9/2004 |
| WO | WO-2005070330 A1 | 8/2005 |
| WO | WO-2005077435 A1 | 8/2005 |
| WO | WO-2005081202 A1 | 9/2005 |
| WO | WO-2006017517 A2 | 2/2006 |
| WO | WO-2006024015 A1 | 3/2006 |
| WO | WO-2006083794 A2 | 8/2006 |
| WO | WO-2006091597 A1 | 8/2006 |
| WO | WO-2006126979 A2 | 11/2006 |
| WO | WO-2007067323 A2 | 6/2007 |
| WO | WO-2007079268 A2 | 7/2007 |
| WO | WO-2007133845 A2 | 11/2007 |
| WO | WO-2007134258 A2 | 11/2007 |
| WO | WO-2008015625 A2 | 2/2008 |
| WO | WO-2008021994 A2 | 2/2008 |
| WO | WO-2008021997 A2 | 2/2008 |
| WO | WO-2008021998 A2 | 2/2008 |
| WO | WO-2008024261 A2 | 2/2008 |
| WO | WO-2008079828 A2 | 7/2008 |
| WO | WO-2008141238 A1 | 11/2008 |
| WO | WO-2009112262 A2 | 9/2009 |

OTHER PUBLICATIONS

Avitall, et al. "A Catheter System to Ablate Atrial Fibrillation in a Sterile Pericarditis Dog Model," Pacing and Clinical Electrophysiology, 1994, vol. 17, pp. 774.

Avitall, "Vagally Mediated Atrial Fibrillation in a Dog Model can be Ablated by Placing Linear Radiofrequency Lesions at the Junction of the Right Atrial Appendage and the Superior Vena Cava," Pacing and Clinical Electrophysiology, 1995, vol. 18, pp. 857.

Baker B.M., et al., "Nonpharmacologic Approaches to the Treatment of Atrial Fibrillation and Atrial Flutter," Journal of Cardiovascular Electrophysiology, 1995, vol. 6 (10 Pt 2), pp. 972-978.

Bhakta D., et al., "Principles of Electroanatomic Mapping," Indian Pacing and Electrophysiology Journal, 2008, vol. 8 (1), pp. 32-50.

Bidoggia H., et al., "Transseptal Left Heart Catheterization: Usefulness of the Intracavitary Electrocardiogram in the Localization of the Fossa Ovalis," Cathet Cardiovasc Diagn, 1991, vol. 24 (3), pp. 221-225, PMID: 1764747 [online], [retrieved Feb. 15, 2010]. Retrieved

(56) References Cited

OTHER PUBLICATIONS from the Internet: <URL: http://www.ncbi.nlm.nih.gov/sites/entrez>.
Bredikis J.J., et al., "Surgery of Tachyarrhythmia: Intracardiac Closed Heart Cryoablation," Pacing and Clinical Electrophysiology, 1990, vol. 13 (Part 2), pp. 1980-1984.
Communication from the Examining Division for Application No. EP06734083.6 dated Nov. 12, 2010, 3 pages.
Communication from the Examining Division for Application No. EP06734083.6 dated Oct. 23, 2009, 1 page.
Communication from the Examining Division for Application No. EP08746822.9 dated Jul. 13, 2010, 1 page.
Co-pending U.S. Appl. No. 61/286,283, filed Dec. 14, 2009.
Co-pending U.S. Appl. No. 61/297,462, filed Jan. 22, 2010.
Cox J.L., "Cardiac Surgery for Arrhythmias," Journal of Cardiovascular Electrophysiology, 2004, vol. 15, pp. 250-262.
Cox J.L., et al., "Five-Year Experience With the Maze Procedure for Atrial Fibrillation," The Annals of Thoracic Surgery, 1993, vol. 56, pp. 814-824.
Cox J.L., et al., "Modification of the Maze Procedure for Atrial Flutter and Atrial Fibrillation," The Journal of Thoracic and Cardiovascular Surgery, 1995, vol. 110, pp. 473-484.
Cox J.L., "The Status of Surgery for Cardiac Arrhythmias," Circulation, 1985, vol. 71, pp. 413-417.
Cox J.L., "The Surgical Treatment of Atrial Fibrillation," The Journal of Thoracic and Cardiovascular Surgery, 1991, vol. 101, pp. 584-592.
Elvan A., et al., "Radiofrequency Catheter Ablation of the Atria Reduces Inducibility and Duration of Atrial Fibrillation in Dogs," Circulation, vol. 91, 1995, pp. 2235-2244 [online], [retrieved Feb. 4, 2013]. Retrieved from the Internet: <URL: http://circ.ahajournals.org/cgi/content/full/91/8/2235>.
Elvan A., et al., "Radiofrequency Catheter Ablation (RFCA) of the Atria Effectively Abolishes Pacing Induced Chronic Atrial Fibrillation," Pacing and Clinical Electrophysiology, 1995, vol. 18, pp. 856.
Elvan, et al., "Replication of the 'Maze' Procedure by Radiofrequency Catheter Ablation Reduces the Ability to Induce Atrial Fibrillation," Pacing and Clinical Electrophysiology, 1994, vol. 17, pp. 774.
European Search Report for Application No. EP07799466.3 dated Nov. 18, 2010, 9 pages.
European Search Report for Application No. EP08746822.9 dated Mar. 29, 2010, 7 Pages.
Examination Communication for Application No. EP06734083.6 dated May 18, 2010, 3 Pages.
Extended European Search Report for Application No. EP06734083.6 dated Jul. 1, 2009, 6 pages.
Extended European Search Report for Application No. EP08755266.7 dated Oct. 22, 2013, 6 Pages.
Fieguth H.G., et al., "Inhibition of Atrial Fibrillation by Pulmonary Vein Isolation and Auricular Resection—Experimental Study in a Sheep Model," The European Journal of Cardio-Thoracic Surgery, 1997, vol. 11, pp. 714-721.
Final Office Action dated Mar. 1, 2010 for U.S. Appl. No. 12/117,655, filed May 8, 2008.
Final Office Action dated Jun. 2, 2011 for U.S. Appl. No. 12/117,655, filed May 8, 2008.
Final Office Action dated May 12, 2011 for U.S. Appl. No. 11/775,771, filed Jul. 10, 2007.
Final Office Action dated Sep. 16, 2010 for U.S. Appl. No. 11/828,267, filed Jul. 25, 2007.
Hoey M.F., et al., "Intramural Ablation Using Radiofrequency Energy Via Screw-Tip Catheter and Saline Electrode," Pacing and Clinical Electrophysiology, 1995, vol. 18, Part II, 487.
Huang, "Increase in the Lesion Size and Decrease in the Impedance Rise with a Saline Infusion Electrode Catheter for Radiofrequency," Circulation, 1989, vol. 80 (4), II-324.
International Search Report and Written Opinion for Application No. PCT/US2008/063324, dated Sep. 22, 2008, 8 pages.
Moser K.M., et al., "Angioscopic Visualization of Pulmonary Emboli," Chest, 1980, vol. 77 (2), pp. 198-201.
Nakamura F., et al., "Percutaneous Intracardiac Surgery With Cardioscopic Guidance," SPIE, 1992, vol. 1642, pp. 214-216.
Non-Final Office Action dated Jun. 7, 2011 for U.S. Appl. No. 12/323,281, filed Nov. 25, 2008.
Non-Final Office Action dated Jun. 8, 2009 for U.S. Appl. No. 12/117,655, filed May 8, 2008.
Non-Final Office Action dated May 9, 2011 for U.S. Appl. No. 11/961,950, filed Dec. 20, 2007.
Non-Final Office Action dated May 9, 2011 for U.S. Appl. No. 11/961,995, filed Dec. 20, 2007.
Non-Final Office Action dated May 9, 2011 for U.S. Appl. No. 11/962,029, filed Dec. 20, 2007.
Non-Final Office Action dated Jun. 10, 2010 for U.S. Appl. No. 11/560,742, filed Nov. 16, 2006.
Non-Final Office Action dated Apr. 11, 2011 for U.S. Appl. No. 11/763,399, filed Jun. 14, 2007.
Non-Final Office Action dated Mar. 11, 2011 for U.S. Appl. No. 11/848,202, filed Aug. 30, 2007.
Non-Final Office Action dated May 11, 2011 for U.S. Appl. No. 11/828,267, filed Jul. 25, 2007.
Non-Final Office Action dated Apr. 12, 2011 for U.S. Appl. No. 12/499,011, filed Jul. 7, 2009.
Non-Final Office Action dated Jan. 14, 2010 for U.S. Appl. No. 11/828,267, filed Jul. 25, 2007.
Non-Final Office Action dated Dec. 16, 2010 for U.S. Appl. No. 12/117,655, filed May 8, 2008.
Non-Final Office Action dated Feb. 18, 2011 for U.S. Appl. No. 12/947,198, filed Nov. 16, 2010.
Non-Final Office Action dated Feb. 18, 2011 for U.S. Appl. No. 12/947,246, filed Nov. 16, 2006.
Non-Final Office Action dated May 20, 2011 for U.S. Appl. No. 11/775,819, filed Jul. 10, 2007.
Non-Final Office Action dated May 20, 2011 for U.S. Appl. No. 11/877,386, filed Oct. 23, 2007.
Non-Final Office Action dated Jul. 21, 2010 for U.S. Appl. No. 11/687,597, filed Mar. 16, 2007.
Non-Final Office Action dated Apr. 22, 2011 for U.S. Appl. No. 12/367,019, filed Feb. 6, 2009.
Non-Final Office Action dated May 23, 2011 for U.S. Appl. No. 11/775,837, filed Jul. 10, 2007.
Non-Final Office Action dated Nov. 24, 2010 for U.S. Appl. No. 11/848,429, filed Aug. 31, 2007.
Non-Final Office Action dated Nov. 24, 2010 for U.S. Appl. No. 12/464,800, filed May 12, 2009.
Non-Final Office Action dated Apr. 25, 2011 for U.S. Appl. No. 11/959,158, filed Dec. 18, 2007.
Non-Final Office Action dated Feb. 25, 2010 for U.S. Appl. No. 11/259,498, filed Oct. 25, 2005.
Non-Final Office Action dated Feb. 25, 2011 for U.S. Appl. No. 11/848,207, filed Aug. 30, 2007.
Non-Final Office Action dated Apr. 26, 2011 for U.S. Appl. No. 11/848,532, filed Aug. 31, 2007.
Non-Final Office Action dated Apr. 27, 2011 for U.S. Appl. No. 11/828,281, filed Jul. 25, 2007.
Non-Final Office Action dated Aug. 27, 2010 for U.S. Appl. No. 11/775,771, filed Jul. 10, 2007.
Non-Final Office Action dated Dec. 27, 2010 for U.S. Appl. No. 12/026,455, filed Feb. 5, 2008.
Notice of Allowance dated Feb. 3, 2011 for U.S. Appl. No. 11/560,732, filed Nov. 16, 2006.
Notice of Allowance dated Jun. 13, 2011 for Japanese Application No. 2007-554156 filed Jan. 30, 2006.
Notice of Allowance dated Nov. 15, 2010 for U.S. Appl. No. 11/259,498, filed Oct. 25, 2005.
Notice of Allowance dated Nov. 15, 2010 for U.S. Appl. No. 11/560,742, filed Nov. 16, 2006.
Notice of Allowance dated Feb. 24, 2011 for U.S. Appl. No. 11/560,732, filed Mar. 16, 2007.
Notice of Allowance dated Feb. 24, 2011 for U.S. Appl. No. 11/687,597, filed Mar. 16, 2007.

(56) References Cited

OTHER PUBLICATIONS

Office Action dated Feb. 15, 2011 for Japanese Application No. 2007-554156 filed Jan. 30, 2006.

Office Action dated Apr. 27, 2011 for Japanese Application No. 2009-500630 filed Mar. 16, 2007.

Pappone C., et al., "Circumferential Radiofrequency Ablation of Pulmonary Vein Ostia," Circulation, 2000, vol. 102, pp. 2619-2628.

Sethi K.K., et al., "Transseptal catheterization for the electrophysiologist: modification with a 'view'," Journal of Interventional Cardiac Electrophysiology, 2001, vol. 5 (1), pp. 97-99.

Supplemental European Search Report for Application No. EP07758716 dated Feb. 28, 2001, 8 Pages.

Supplementary European search report for Application No. EP07812146.4 dated Nov. 18, 2010, 8 Pages.

Supplementary European Search Report for Application No. EP07841754, dated Jun. 30, 2010, 6 pages.

Thiagalingam A., et al., "Cooled Needle Catheter Ablation Creates Deeper and Wider Lesions than Irrigated Tip Catheter Ablation," Journal of Cardiovascular Electrophysiology, 2005, vol. 16 (5), pp. 1-8.

Uchida Y., "Developmental History of Cardioscopes", in: Coronary Angioscopy, Chapter 19, Futura Publishing Company, Inc., 2001, pp. 187-197.

Willkampf F.H., et al., "Radiofrequency Ablation with a Cooled Porous Electrode Catheter," JACC, Abstract, 1988, vol. 11 (2), pp. 17A.

Extended European Search Report for Application No. 15201701.8, dated Feb. 5, 2016, 9 pages.

\* cited by examiner

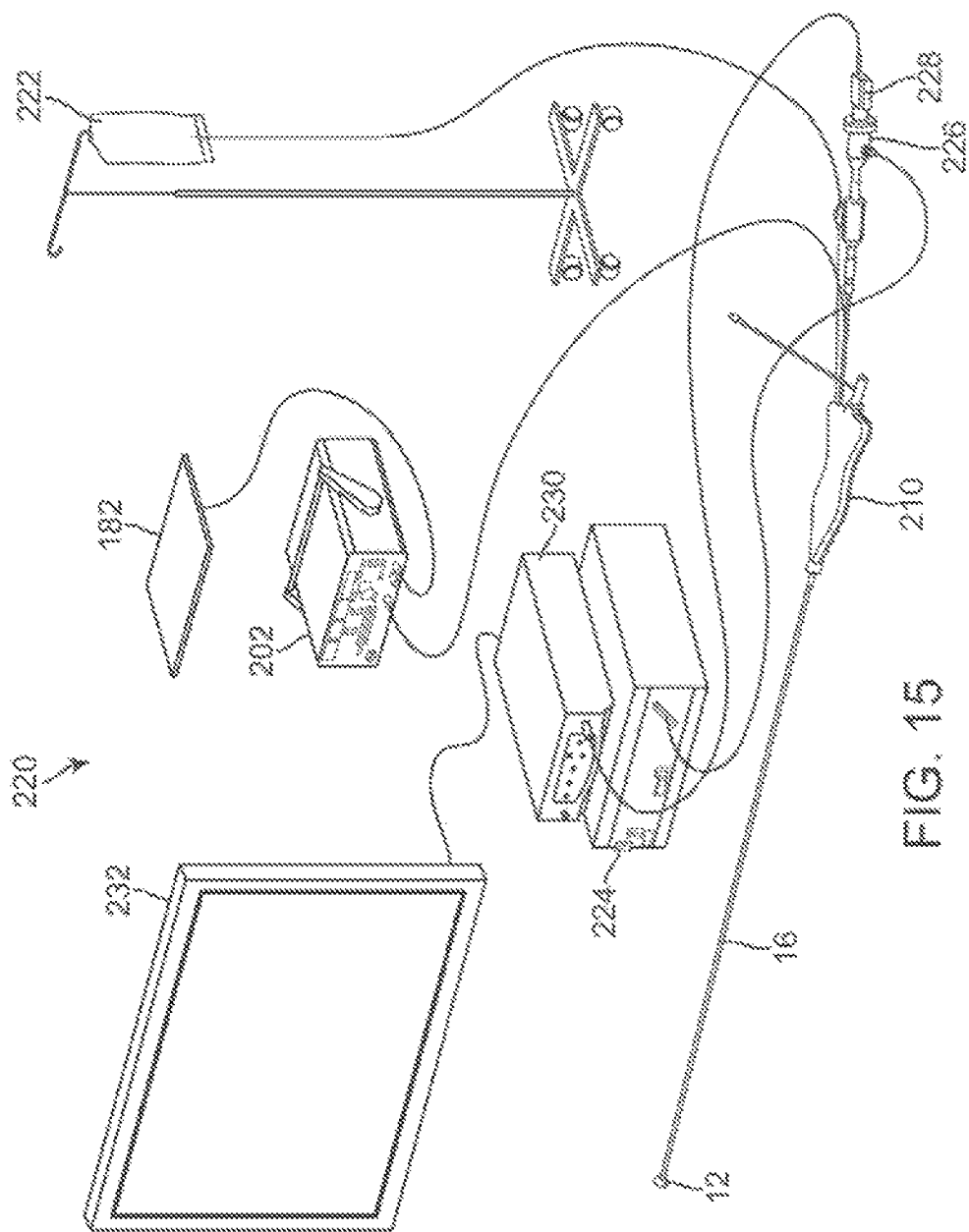

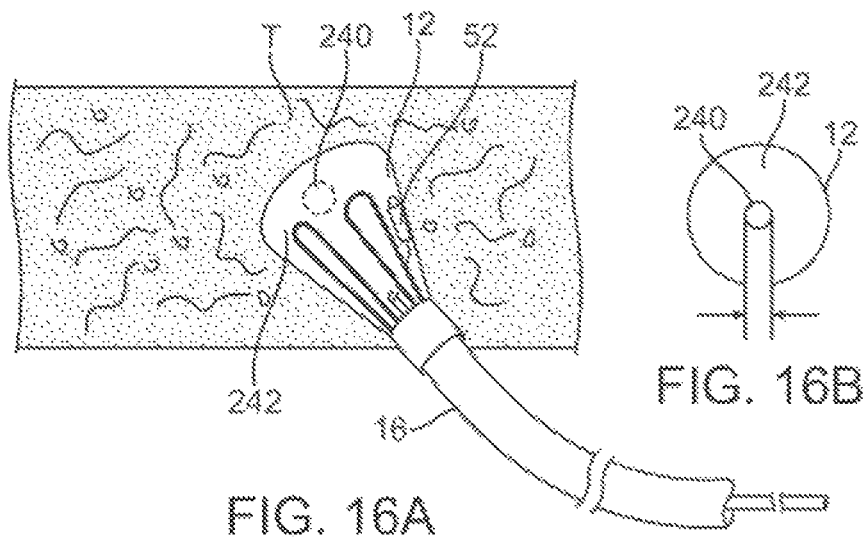
FIG. 16A
FIG. 16B
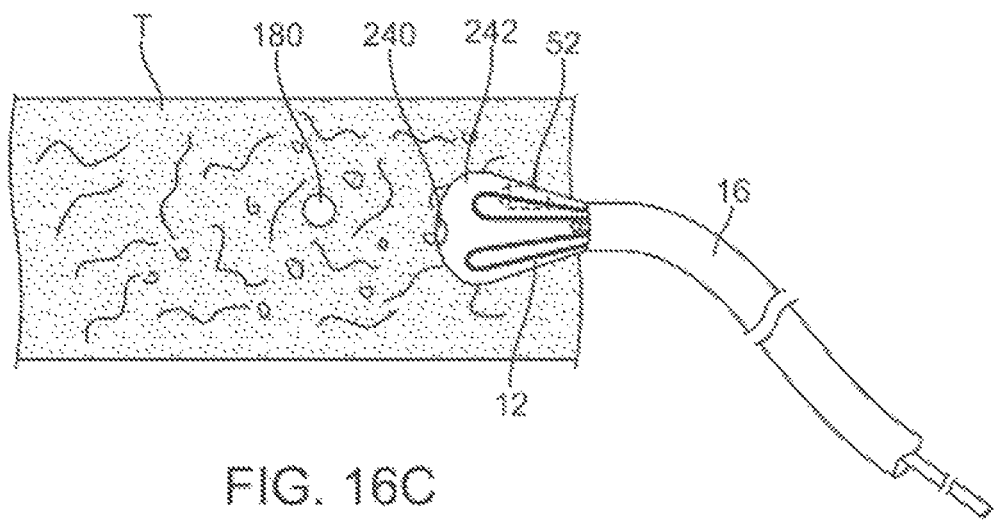
FIG. 16C

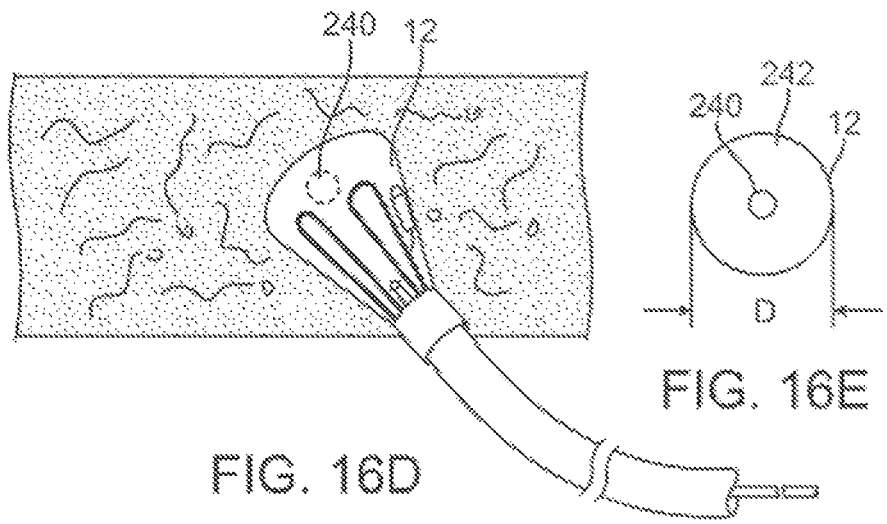
FIG. 16D
FIG. 16E
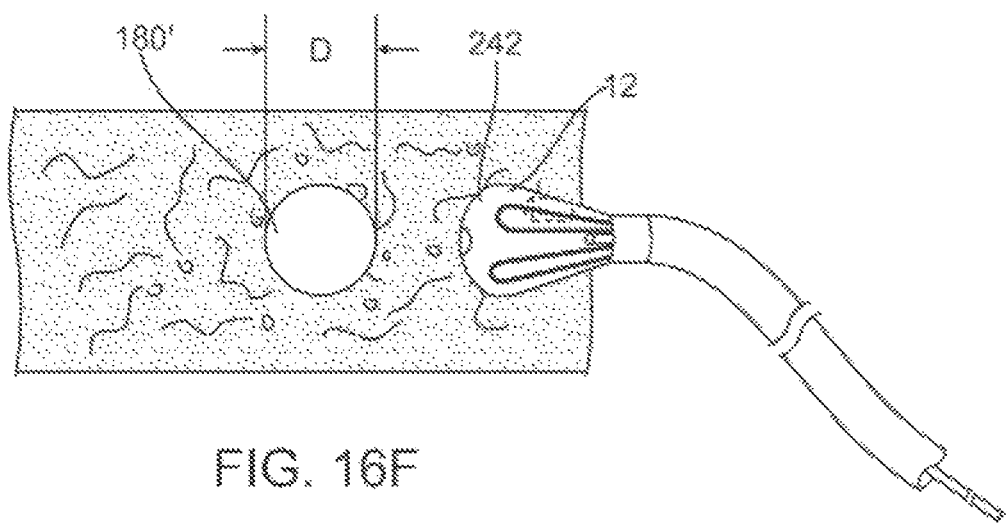
FIG. 16F

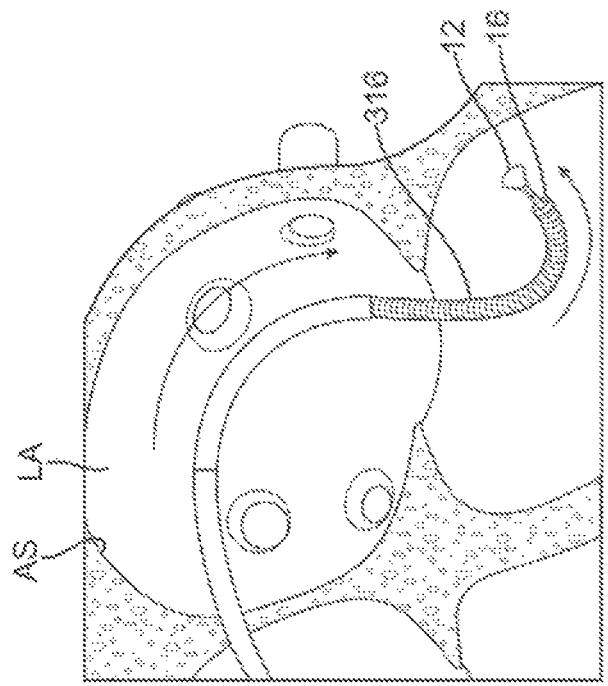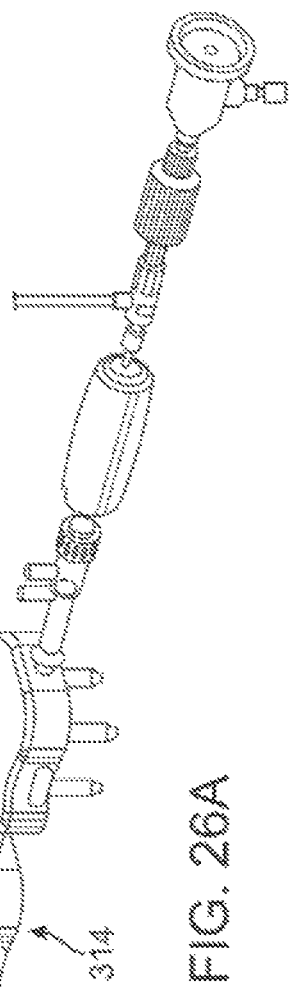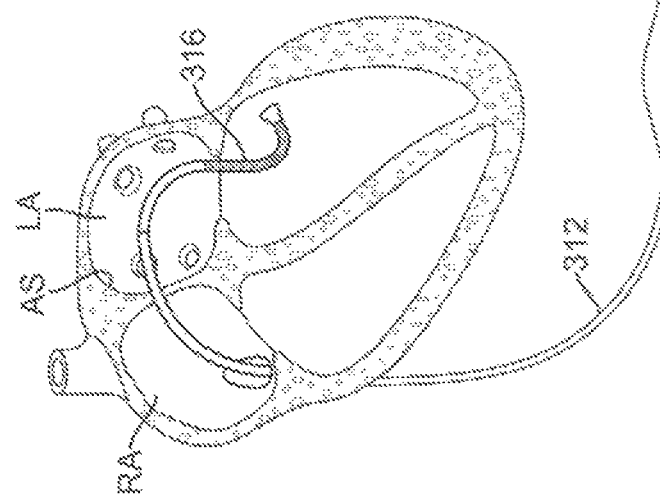
FIG. 26B
FIG. 26A

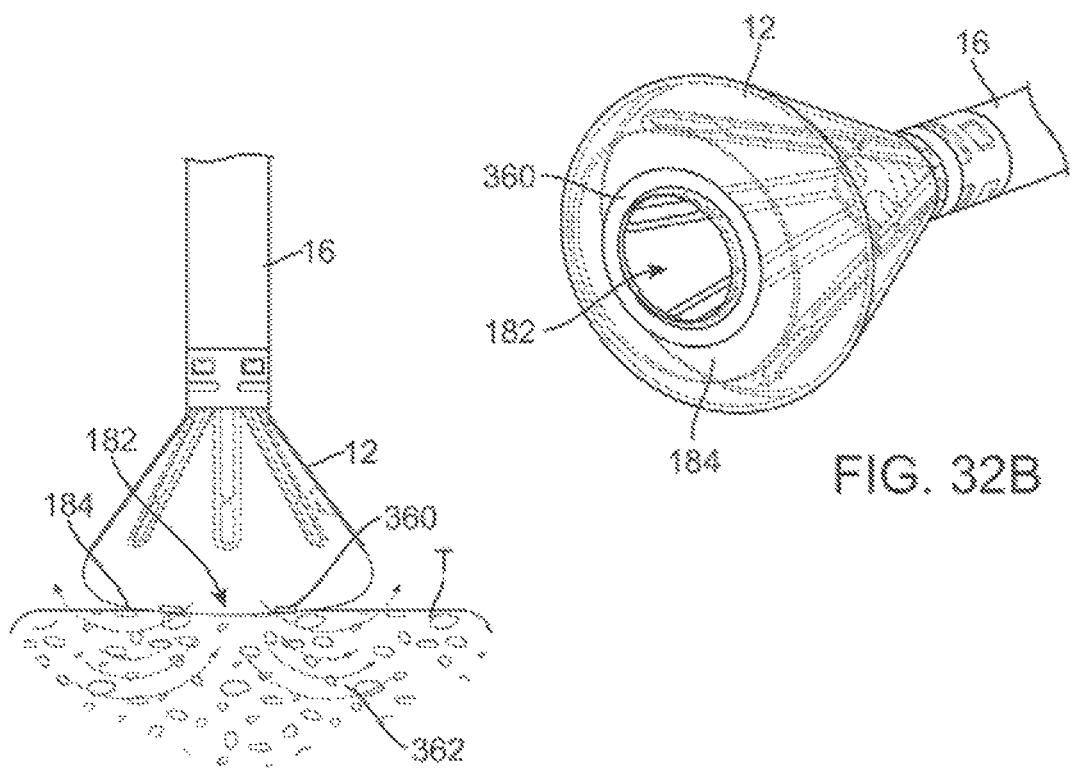
FIG. 32A
FIG. 32B
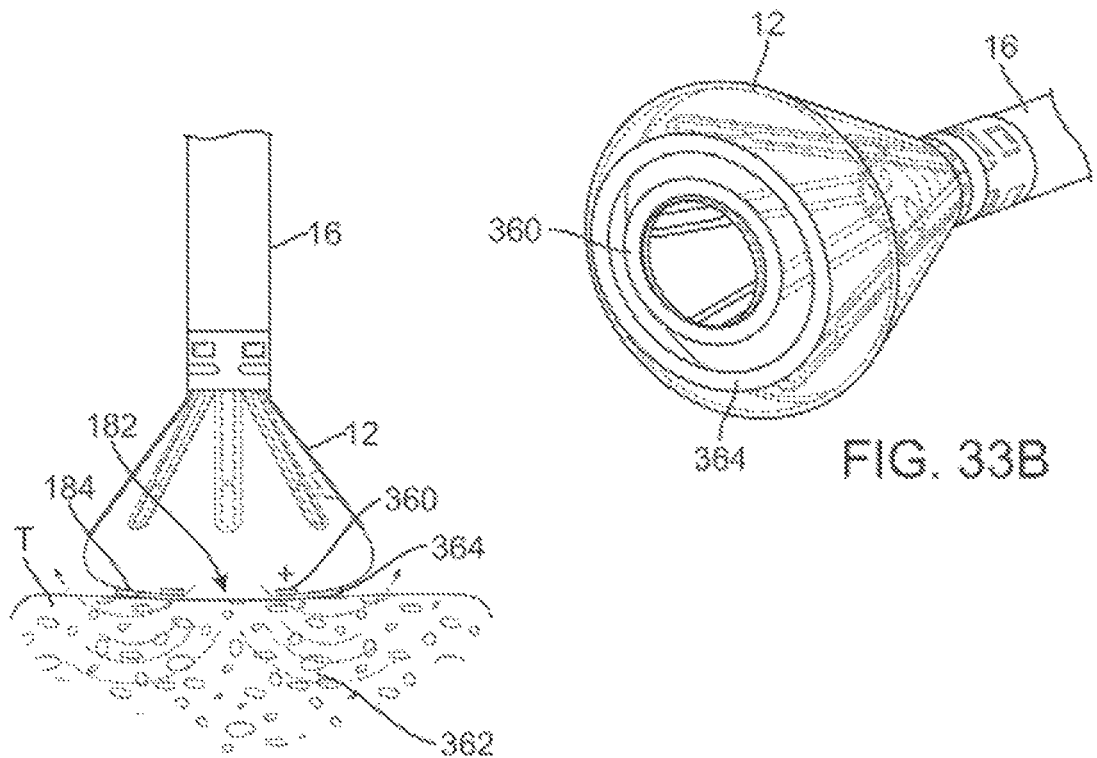
FIG. 33A
FIG. 33B

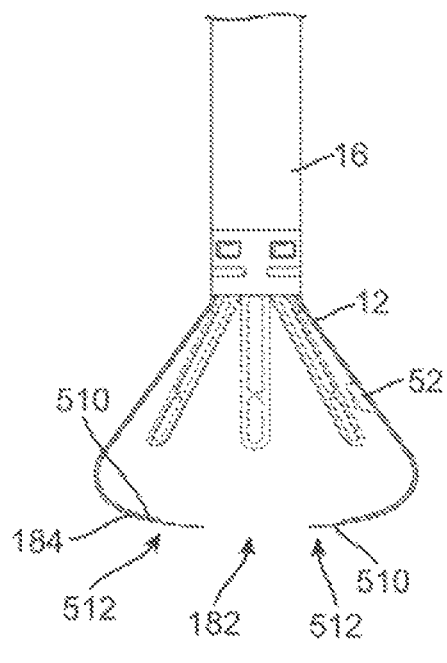
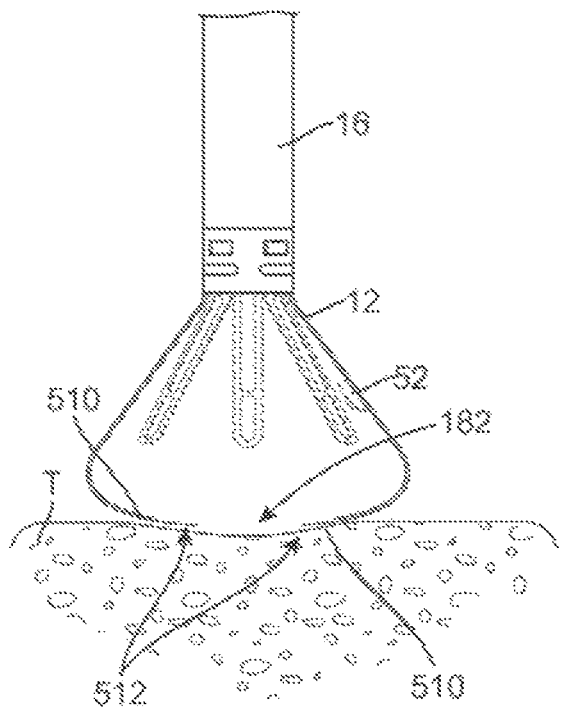
FIG. 44A   FIG. 44B
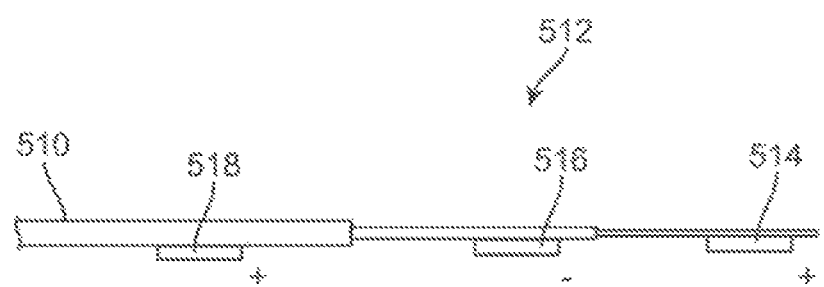
FIG. 44C

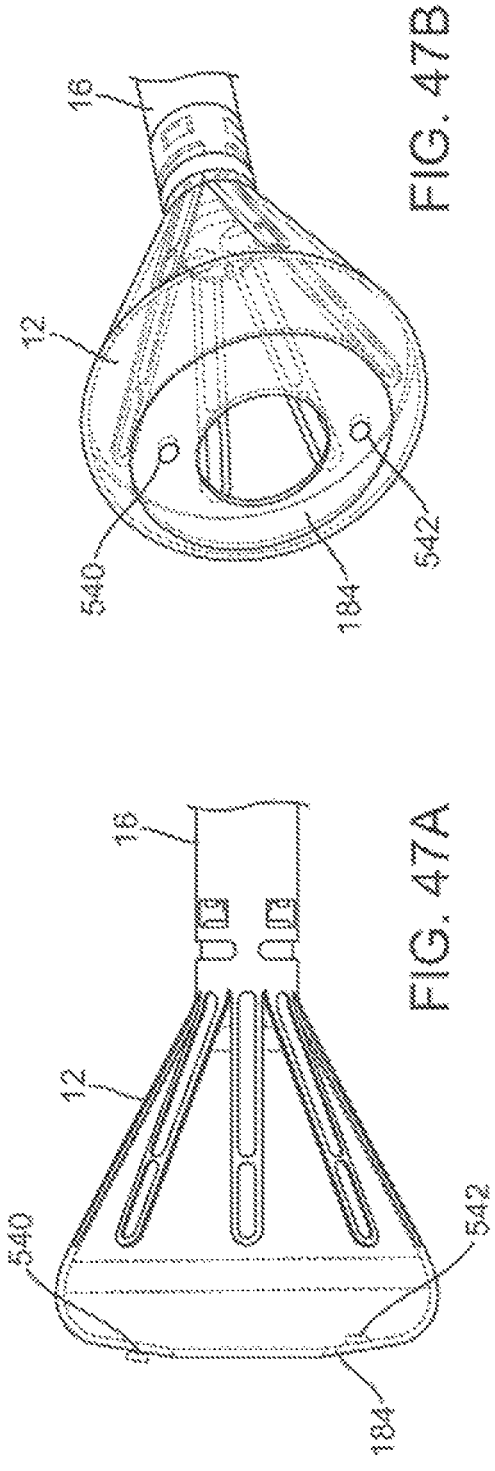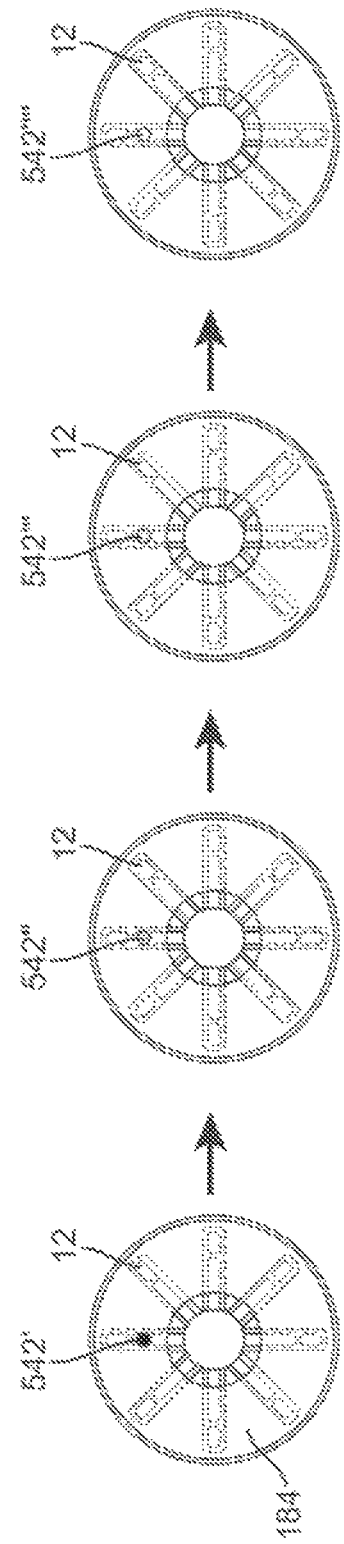

VISUAL ELECTRODE ABLATION SYSTEMS

CROSS-REFERENCE TO RELATED APPLICATIONS

This application is a Divisional of U.S. patent application Ser. No. 12/118,439, filed May 9, 2008, entitled "Visual Electrode Ablation Systems," which claims the benefit of priority to U.S. Prov. Pat. App. 60/917,487 filed May 11, 2007, the full disclosures of which (including all references incorporated by reference therein) are incorporated by reference herein for all purposes.

FIELD OF THE INVENTION

The present invention relates generally to medical devices used for accessing, visualizing, and/or treating regions of tissue within a body. More particularly, the present invention relates to methods and apparatus for intravascularly accessing regions within the body, such as within the heart, and ablating tissue regions via energy delivery through an electrolytic fluid through which the tissue to be treated is also visualized.

BACKGROUND OF THE INVENTION

Conventional devices for accessing and visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Moreover, many of the conventional imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. Nos. 5,895, 417; 5,941,845; and 6,129,724, used on the epicardial surface of the heart may be difficult in assuring a transmural lesion or complete blockage of electrical signals. In addition, current devices may have difficulty dealing with varying thickness of tissue through which a transmural lesion is desired.

Conventional accompanying imaging devices, such as fluoroscopy, are unable to detect perpendicular electrode orientation, catheter movement during the cardiac cycle, and image catheter position throughout lesion formation. Without real-time visualization, it is difficult to reposition devices to another area that requires transmural lesion ablation. The absence of real-time visualization also poses the risk of incorrect placement and ablation of critical structures such as sinus node tissue which can lead to fatal consequences.

BRIEF SUMMARY OF THE INVENTION

A tissue imaging system which is able to provide real-time in vivo access to and images of tissue regions within body lumens such as the heart through opaque media such as blood and which also provides instruments for therapeutic procedures is provided by the invention.

The tissue-imaging apparatus relates to embodiments of a device and method to provide real-time images in vivo of tissue regions within a body lumen such as a heart, which is filled with blood flowing dynamically through it. Such an apparatus may be utilized for many procedures, e.g., mitral valvuloplasty, left atrial appendage closure, arrhythmia ablation (such as treatment for atrial fibrillation), transseptal access and patent foramen ovale closure among other procedures. Further details of such a visualization catheter and methods of use are shown and described in U.S. Pat. Pub. 2006/0184048 A1, which is incorporated herein by reference in its entirety.

Generally, the embodiments of a tissue imaging and manipulation device depicted in the present invention meet the challenge and solve the problem of accessing regions of the body which are typically difficult to access. The design and control of the catheter shaft and the distal tip of the device as disclosed here provide a device uniquely capable of accessing a region such as the human heart, which is a region not only difficult to access, but which also has continuous blood flow. The blood flow provides a barrier to visualizing the local tissue, which in turn makes any manipulation at the local tissue nearly impossible. The unique elements that form the catheter shaft and the distal tip of the device, including the separate control of the shaft and tip and several optional modes of manipulation of either or both, provide for a device adaptable to addressing the challenges inherent in intravascular access and manipulation of heart tissue, and for accomplishing a procedure in any other difficult-to-access region in the body which is bathed in a medium that interfers with visualization.

Blood is continuously flowing through the heart at all times, and as such presents a challenge to direct visualization and subsequent manipulation of heart tissue. The tissue imaging and manipulation apparatus can comprise a delivery catheter or sheath through which a deployment catheter and imaging hood may be advanced for placement against or adjacent to the tissue to be imaged. The deployment catheter can have a fluid delivery lumen through it as well as an imaging lumen within which an optical imaging fiber or electronic imaging assembly may be disposed for imaging tissue. The distal tip of the device is an articulatable tip connected to the catheter shaft, when deployed, the imaging hood within the articulatable tip may be expanded into any number of shapes, e.g., cylindrical, conical as shown, semispherical, etc., provided that an open area or field is defined by the imaging hood. The open area of the articulatable tip is the area within which the tissue region of interest may be imaged. The imaging hood may also define an atraumatic contact lip or edge for placement or abutment against the tissue surface in the region of interest. The distal end of the deployment catheter or separate manipulatable catheters within a delivery sheath may be articulated through various controlling mechanisms such as push-pull wires manually or via computer control.

The visualization catheter may also have one or more membranes or layers of a polymeric material which covers at least a portion of the open area. The membrane or layer may be an extension of the deployed hood or it may be a separate structure. In either case, the membrane or layer may define at least one opening which allows for fluid communication between the visualization hood and the fluid environment within which the catheter is immersed.

In operation, after the imaging hood (at the articulatable tip) has been deployed, fluid may be pumped at a positive pressure through the fluid delivery lumen (within the catheter) until the fluid fills the open area completely and displaces any blood from within the open area. When the hood and membrane or layer is pressed against the tissue region to be visualized or treated, the contact between the one or more openings and the tissue surface may help to retain the clear fluid within the hood for visualization. Moreover, the membrane or layer may help to retain the fluid within the hood while also minimizing any fluid leakage therefrom. Additionally, the one or more openings may also provide for direct access to the underlying tissue region to be treated by any number of tools or instruments positioned within the hood at the articulatable tip.

The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

The imaging hood may be deployed into an expanded shape and retracted within a catheter utilizing various mechanisms. Moreover, an imaging element, such as a CCD/CMOS imaging camera, may be positioned distally or proximally of the imaging hood when collapsed into its low-profile configuration. Such a configuration may reduce or eliminate friction during deployment and retraction as well as increase the available space within the catheter not only for the imaging unit but also for the hood.

In further controlling the flow of the purging fluid within the hood, various measures may be taken in configuring the assembly to allow for the infusion and controlled retention of the clearing fluid into the hood. By controlling the infusion and retention of the clearing fluid, the introduction of the clearing fluid into the patient body may be limited and the clarity of the imaging of the underlying tissue through the fluid within the hood may be maintained for relatively longer periods of time by inhibiting, delaying, or preventing the infusion of surrounding blood into the viewing field.

When ablating the underlying visualized tissue, a number of instruments may be utilized for performing the ablation upon the tissue, e.g., advancing an ablation probe through the hood and into ablative contact with the tissue while under direct visualization. Yet because an ablative probe is surrounded by the purging fluid, such as saline, which is already utilized for visualizing through to the underlying tissue, the conductive properties of the fluid may be taken advantage of by passing electrical currents directly through the fluid itself to the underlying tissue. Thus, tissue regions which are directly imaged through the fluid within the imaging hood may be ablated via electrical energy conducted through the fluid without the need for a separate ablation probe or instrument.

Ablation within the hood may further provide an isolated and controlled environment for tissue ablation. With the blood purged from the hood interior, the visual electrode system may provide for more efficient ablation with less power and time involved and may further facilitate the formation of transmural lesions in the treated tissue. Additionally, the purging fluid may be varied in temperature, for example, to provide cooling to the underlying ablated tissue and the fluid may also be infused with any number of biological compounds for enhancing treatment of the tissue. Because the hood may also form a seal against regions with uneven anatomy, such as trabeculated tissue surfaces, the discharging electrode may ablate such tissue surfaces so long as the fluid discharged from hood is in contact with the underlying tissue rather than having to articulate a separate ablation probe for directly contacting the tissue regions between folds.

A visual electrode may thus be utilized for transmitting energy such as RF energy to the underlying tissue while simultaneously visualizing the same tissue being treated. This may be accomplished by use of a discharging electrode positioned through the deployment catheter to reside at least partially within the hood such that the electrode is in contact with the purging fluid. In other variations, one or more of the support struts along the hood itself may be optionally utilized as the discharging electrode. In either case, an unobstructed view of the ablation site directly beneath the electrode may be provided. This unobstructed view may not only provide visual confirmation of sufficient electrode-to-tissue contact, but may also provide visual confirmation of any changes in the color tissue. For example, visual confirmation of the blanching of the tissue color from a pink color to a whitened color may indicate confirmation of lesion formation and may be further indicative of sufficient electrode-to-tissue contact. Additionally, the blanched tissue may be indicative of a width and/or depth of the lesion formed in real time.

To access regions within the body, e.g., the chambers of the heart, the visual electrode assembly may be positioned upon an articulatable catheter having a dual-steering capability, such as a proximal section configured to articulate in a first plane, and a distal section configured to articulate in multiple planes, e.g., four-way steering capability. Alternatively, a passively steerable deployment catheter may be steered via an articulatable outer sheath which may be manually or computer controlled. Moreover, steering may further be enhanced by orientation markers placed upon the hood itself. Corresponding marks may be placed upon the handle as well to provide a directional indication of articulation direction when viewed upon a monitor of the visualization field and in manipulating the hood accordingly.

Variations in the electrode structure may also be varied as well as variations in the hood structure itself to further facilitate visual ablation. For instance, the hood may be configured as an expandable membrane having one or more purging ports for ablation against angled tissue surfaces. Also, the discharging electrode may be formed as a sputter coated ring placed upon the distal membrane or other variations may be utilized.

Other variations may incorporate the use of suction or negative pressure formation within the hood to facilitate the formation of a seal between the aperture and underlying tissue. Such systems may be configured to form a recirculating flow within the hood to reduce saline discharge as well as to provide a cooling effect upon the treated tissue.

Because the ablative energy is transmitted through the purging fluid, lesions having a relatively wider area may be formed than possible with conventional ablation probes. The lesion area may be formed according to the size and/or shape of the aperture through which the purging fluid contacts the underlying tissue. Alternatively, a thin layer of saline fluid from the aperture may additionally become isolated beneath the base of the hood, thus further increasing the potential area for lesion formation. To facilitate measurement of the lesions under visualization, the hood and/or distal membrane may incorporate gradations or markings for estimating the size of lesions formed by the visual electrode.

Additionally, the visual confirmation of the ablated tissue may allow the user to also identify lesion borders during or post-treatment and may facilitate the formation of overlapping lesions to form contiguous lesions about tissue regions, such as the pulmonary vein ostia. Also, the hood may be utilized to locate previously formed discontiguous lesions for ablation of any gaps between these lesions.

Color feedback may also be utilized in determining whether irreversible tissue damage has been achieved as well as for determining temperature feedback during an ablation treatment. Such feedback may be provided not only by the tissue color itself, but also by features such as one or more thermochromic indicators positioned along the hood in contact with the treated tissue or within the hood for monitoring a temperature of the purging fluid.

Aside from visual confirmation of lesion formation, unobstructed visual confirmation of the tissue during ablation may allow for the monitoring of bubble formation upon the tissue surface as indications of potential endocardial disruptions. Software incorporating algorithms using edge detection technology may be utilized to monitor the tissue surface for parameters such as the quantity and/or rate of bubble formation within the visual field. Such monitoring may be utilized to automatically to reduce or cease power levels to prevent any endocardial disruptions from occurring as a safety measure.

Other variations may incorporate the use of one or more electrode assemblies across the distal membrane of the hood to not only ensure contact with the tissue but for other features such as enabling electrocardiogram readings. Yet other features may include the use of ultrasound transducers for measuring tissue thicknesses for adjusting power levels accordingly. Such ultrasound transducers can also be used to determine the distance between the hood and the tissue to facilitate catheter manipulation and steering.

BRIEF DESCRIPTION OF THE DRAWINGS

FIG. 15 illustrates an assembly view of another example of a visualization system configured for visualized ablation while viewed upon a monitor.

FIGS. 16A and 16B illustrate perspective and end views, respectively, of a visualization catheter positioned upon a tissue region for ablation treatment.

FIG. 16C illustrates a perspective view of the visualization catheter having completed ablation treatment and the resulting lesion upon the treated tissue.

FIGS. 16D and 16E illustrate perspective and end views, respectively, of another example where the hood may isolate the region of tissue beneath the distal membrane for ablation.

FIG. 16F illustrates a perspective view of the resulting lesion which is formed beneath the distal membrane approximating the diameter of the entire hood.

FIGS. 26A and 26B show partial cross-sectional side views of the visualization catheter advanced through and articulated by a robotically controllable sheath.

FIGS. 32A and 32B show side and perspective views, respectively, of another variation where a ring electrode is formed directly upon the distal membrane adjacent to the aperture.

FIGS. 33A and 33B show side and perspective views, respectively, of yet another variation where concentric ring electrodes are formed directly upon the distal membrane to form a bipolar electrode configuration.

FIGS. 44A and 44B show partial cross-sectional side views of another variation utilizing electrodes positioned upon biased support members for detecting electrical activity of the underlying ablated tissue.

FIG. 44C shows a detail side view of an electrode assembly positioned upon one of the biased support members.

FIGS. 47A and 47B show side and perspective views of another variation of the hood which may incorporate one or more thermochromic indicators for visually monitoring a temperature of the ablated tissue and/or of the purging fluid.

FIGS. 48A to 48D illustrate end views of the hood with the one or more thermochromic indicators changing its color to indicate a temperature of the ablated tissue.

DETAILED DESCRIPTION OF THE INVENTION

Various exemplary embodiments of the invention are described below. Reference is made to these examples in a non-limiting sense. They are provided to illustrate more, broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

The tissue-imaging and manipulation apparatus of the invention is able to provide real-time images in vivo of tissue regions within a body lumen such as a heart, which are filled with blood flowing dynamically through the region. The apparatus is also able to provide intravascular tools and instruments for performing various procedures upon the imaged tissue regions. Such an apparatus may be utilized for many procedures, e.g., facilitating transseptal; access to the left atrium, cannulating the coronary sinus, diagnosis of valve regurgitation/stenosis, valvuloplasty, atrial appendage closure, arrhythmogenic focus ablation (such as for treating atrial fibrillation), among other procedures. Disclosure and information regarding tissue visualization catheters generally which can be applied to the invention are shown and described in further detail in commonly owned U.S. patent application Ser. No. 11/259,498 filed Oct. 25, 2005, and published as 2006/0184048, which is incorporated herein by reference in its entirety. The basic apparatus for visualizing and manipulating tissue upon intravascular access to the target region are depicted in FIGS. 1-10. The specific details of the invention that permit specific access to difficult-to-access regions such as regions in the heart are depicted in FIGS. 11 to 32. Specific embodiments depicting devices and methods for specific heart-based tissue manipulations such as forming lesions around the pulmonary ostia are shown in FIGS. 28 to 32.

Figure 1A:
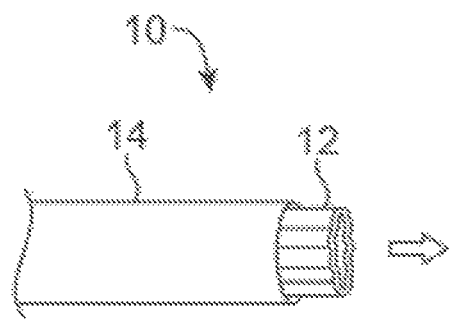
FIG. 1A shows a side view of one variation of a tissue imaging apparatus during deployment from a sheath or delivery catheter.
Figure 1B:
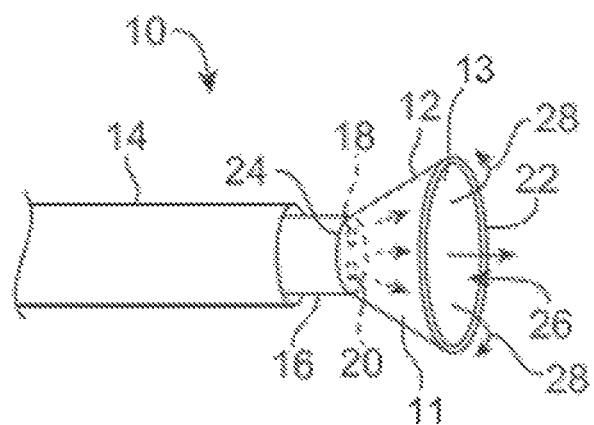
FIG. 1B shows the deployed tissue imaging apparatus of FIG. 1A having an optionally expandable hood or sheath attached to an imaging and/or diagnostic catheter.
Figure 1C:
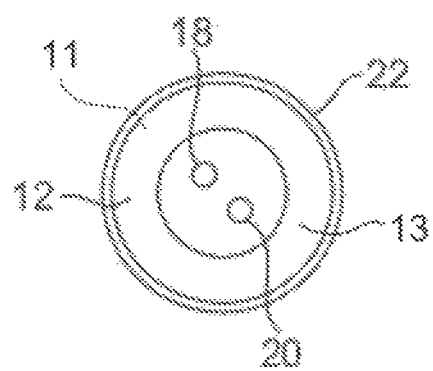
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
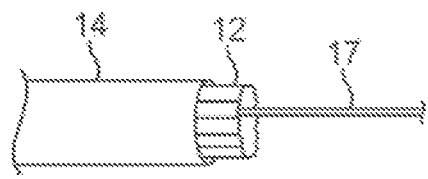
FIGS. 1D to 1F show the apparatus of FIGS. 1A to 1C with an additional lumen, e.g., for passage of a guidewire therethrough.
Figure 1E:
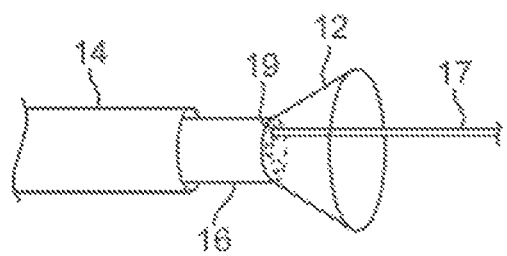
Figure 1F:
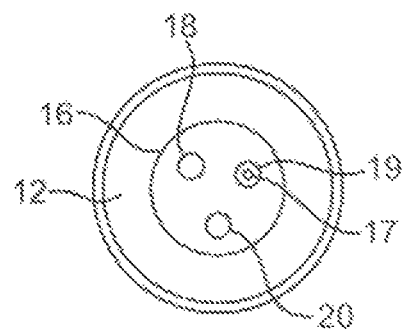

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 2A:
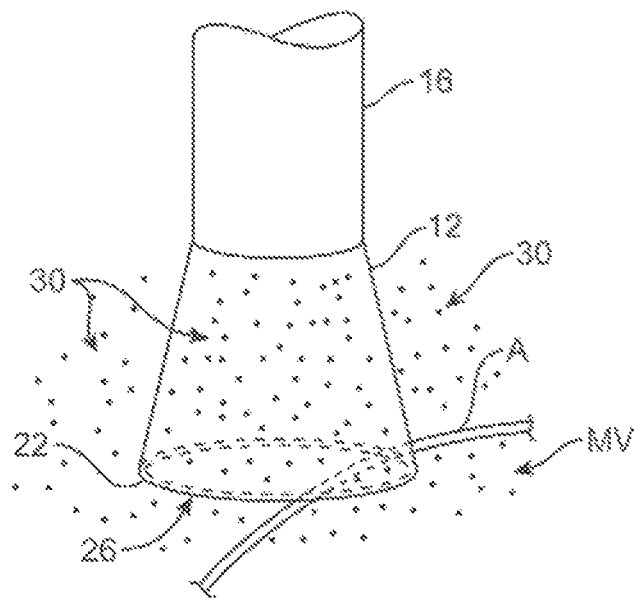
FIGS. 2A and 2B show one example of a deployed tissue imager positioned against or adjacent to the tissue to be imaged and a flow of fluid, such as saline, displacing blood from within the expandable hood.
Figure 2B:
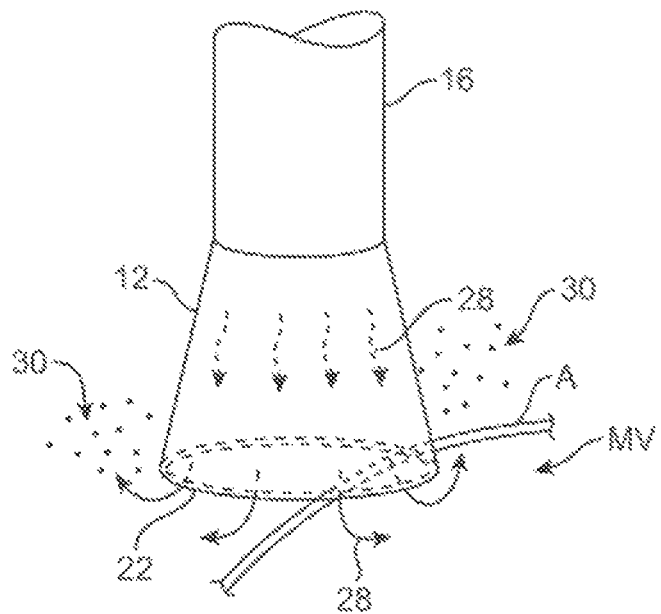

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3A:
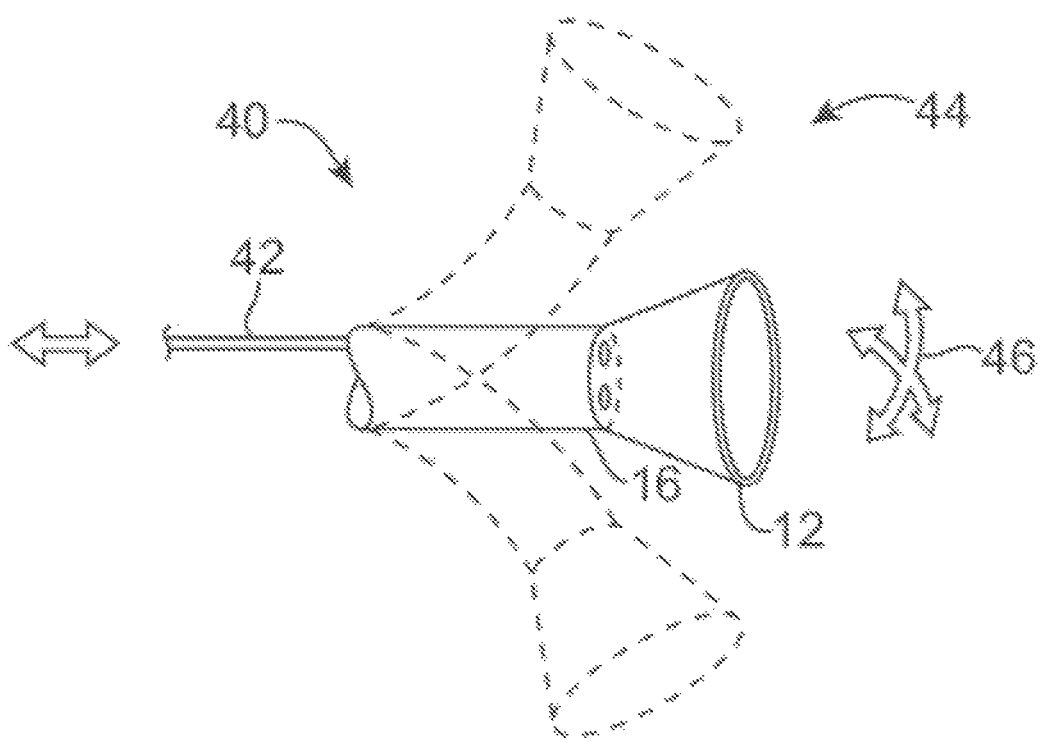
FIG. 3A shows an articulatable imaging assembly which may be manipulated via push-pull wires or by computer control.
Figure 3B:
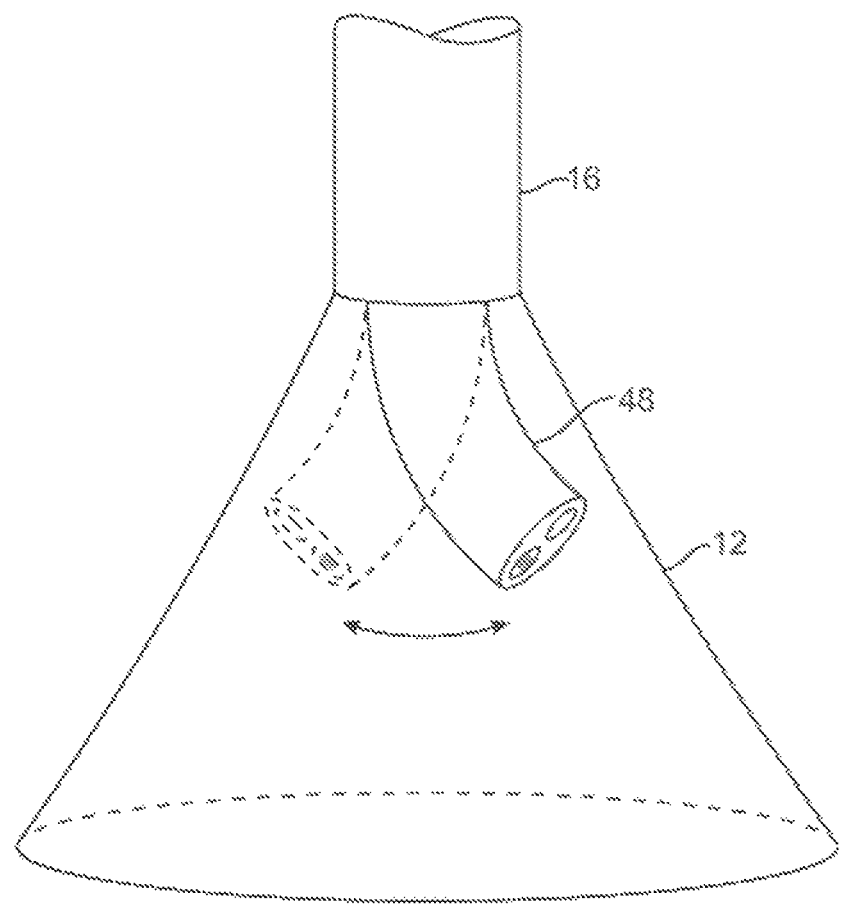
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
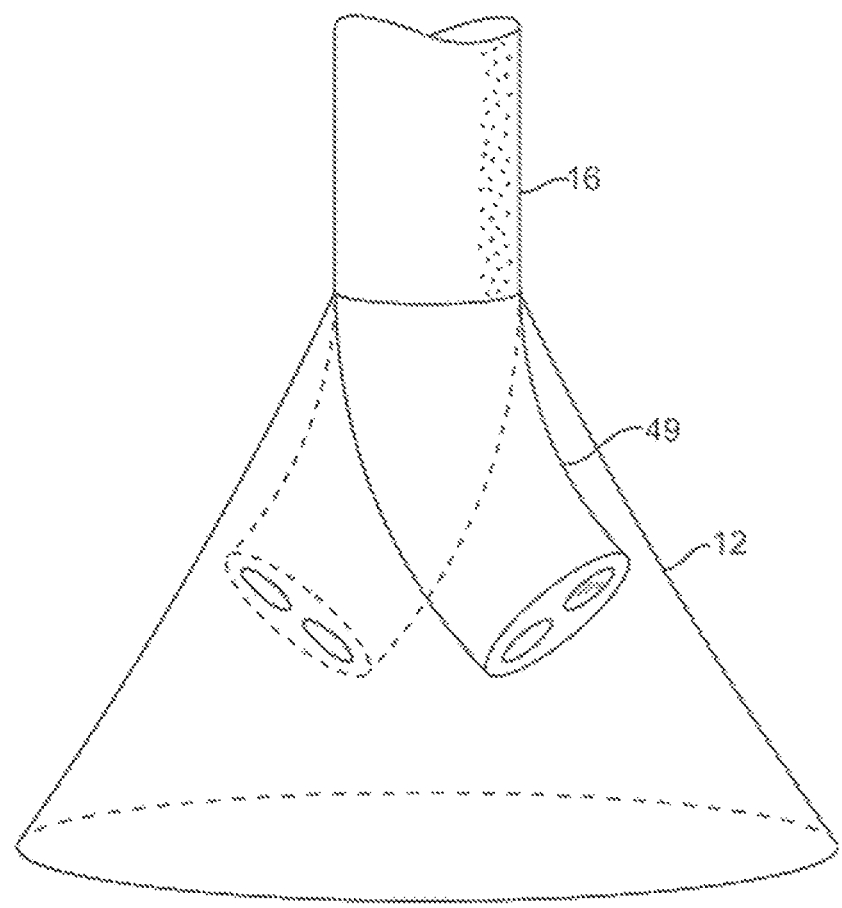

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
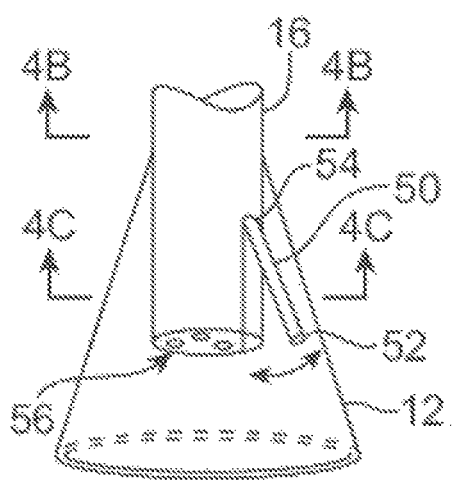
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52, e.g., a CCD or CMOS imager or optical fiber, attached at its distal end with its proximal end connected to deployment catheter 16 via a pivoting connection 54.

Figure 4B:
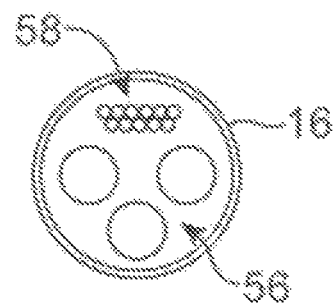
Figure 4C:
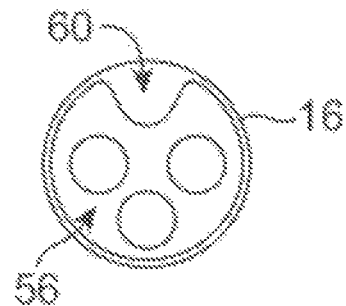

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

Figure 4D:
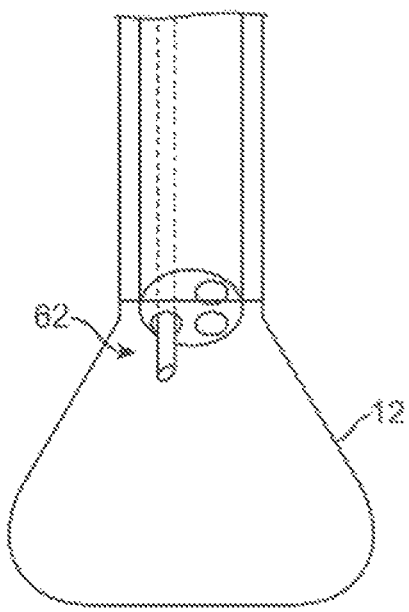
FIGS. 4D and 4E show examples of various visualization imagers which may be utilized within or along the imaging hood.
Figure 4E:
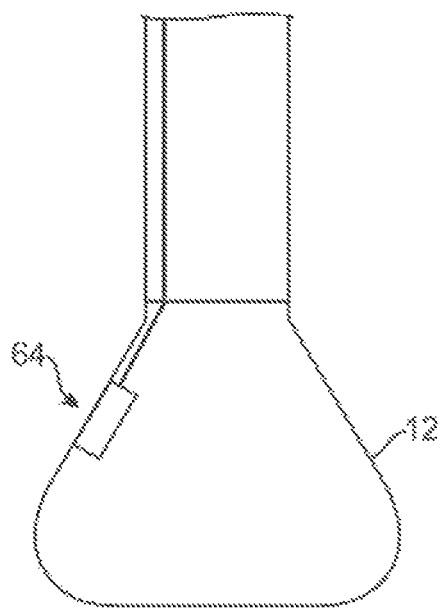

FIG. 4D shows a partial cross-sectional view of an example where one or more optical fiber bundles 62 may be positioned within the catheter and within imaging hood 12 to provide direct in-line imaging of the open area within hood 12. FIG. 4E shows another example where an imaging element 64 (e.g., CCD or CMOS electronic imager) may be placed along an interior surface of imaging hood 12 to provide imaging of the open area such that the imaging element 64 is, off-axis relative to a longitudinal axis of the hood 12. The off-axis position of element 64 may provide for direct visualization and uninhibited access by instruments from the catheter to the underlying tissue during treatment.

Figure 5:
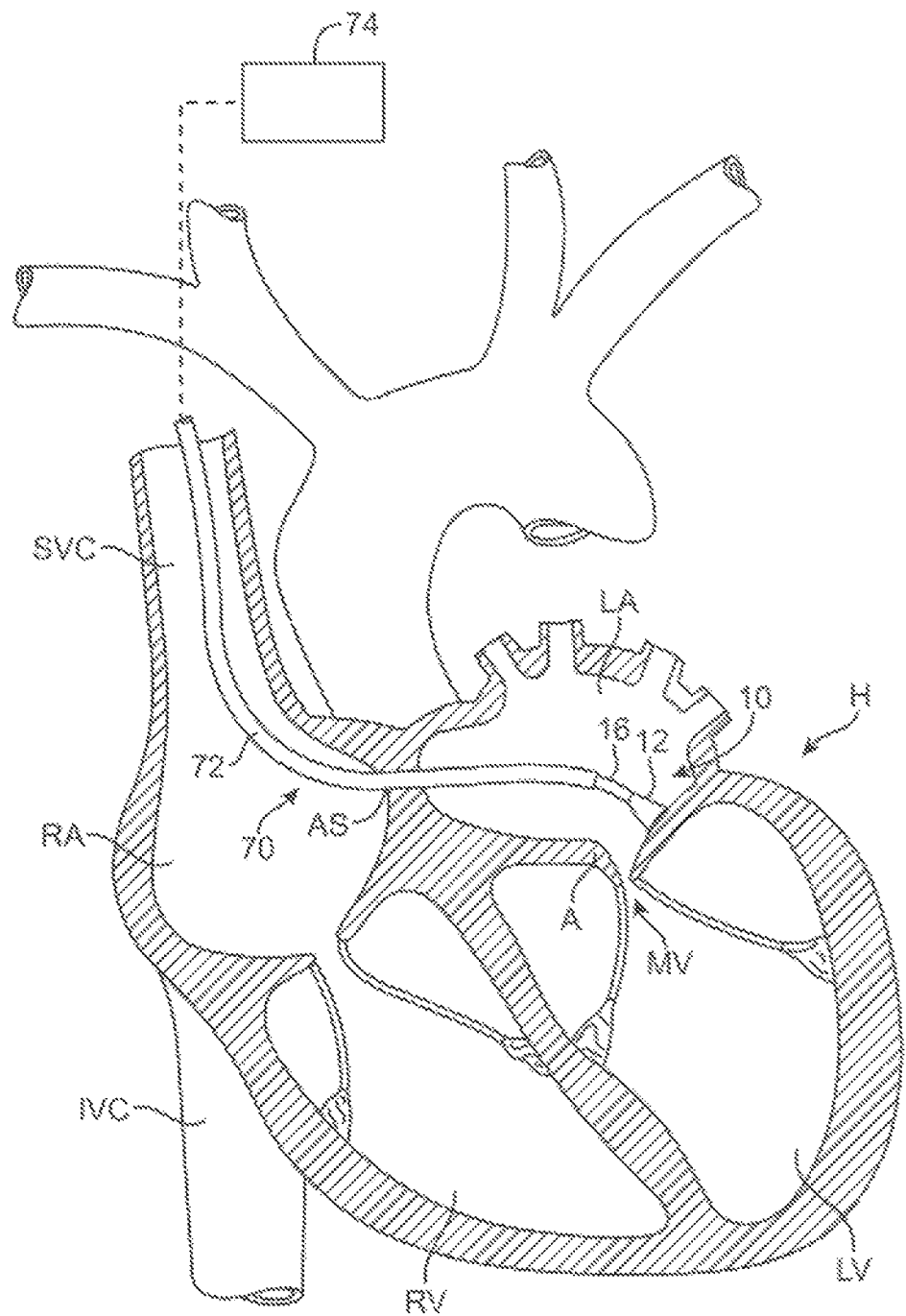
FIG. 5 shows an illustrative view of an example of a tissue imager advanced intravascularly within a heart for imaging tissue regions within an atrial chamber.

FIG. 5 shows an illustrative cross-sectional view of a heart H having tissue regions of interest being viewed via an imaging assembly 10. In this example, delivery catheter assembly 70 may be introduced percutaneously into the patient's vasculature and advanced through the superior vena cava SVC and into the right atrium RA. The delivery catheter or sheath 72 may be articulated through the atrial septum AS and into the left atrium LA for viewing or treating the tissue, e.g., the annulus A, surrounding the mitral valve MV. As shown, deployment catheter 16 and imaging hood 12 may be advanced out of delivery catheter 72 and brought into contact or in proximity to the tissue region of interest. In other examples, delivery catheter assembly 70 may be advanced through the inferior vena cava IVC, if so desired. Moreover, other regions of the heart H, e.g., the right ventricle RV or left ventricle LV, may also be accessed and imaged or treated by imaging assembly 10.

In accessing regions of the heart H or other parts of the body, the delivery catheter or sheath 14 may comprise a conventional intra-vascular catheter or an endoluminal delivery device. Alternatively, robotically-controlled delivery catheters may also be optionally utilized with the imaging assembly described herein, in which case a computer-controller 74 may be used to control the articulation and positioning of the delivery catheter 14. An example of a robotically-controlled delivery catheter which may be utilized is described in further detail in US Pat. Pub. 2002/0087169 A1 to Brock et al. entitled "Flexible Instrument", which is incorporated herein by reference in its entirety. Other robotically-controlled delivery catheters manufactured by Hansen Medical, Inc. (Mountain View, Calif.) may also be utilized with the delivery catheter 14.

Figure 6A:
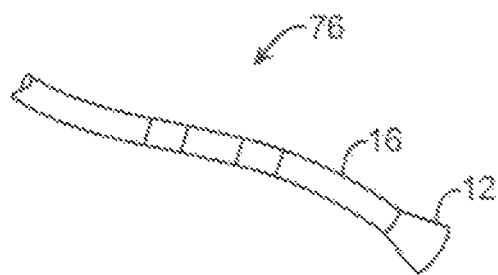
FIGS. 6A to 6C illustrate deployment catheters having one or more optional inflatable balloons or anchors for stabilizing the device during a procedure.
Figure 6B:
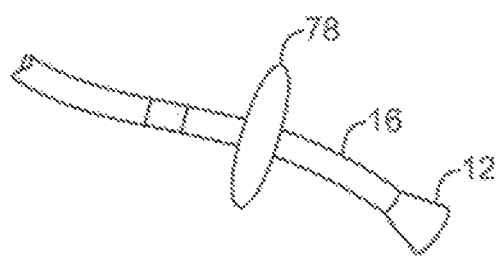
Figure 6C:
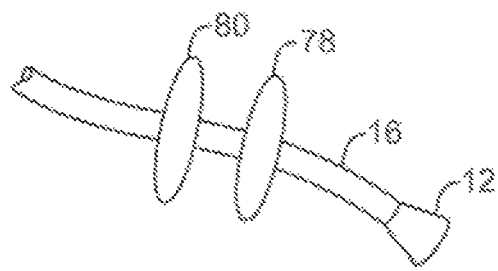

To facilitate stabilization of the deployment catheter 16 during a procedure, one or more inflatable balloons or anchors 76 may be positioned along the length of catheter 16, as shown in FIG. 6A. For example, when utilizing a transseptal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
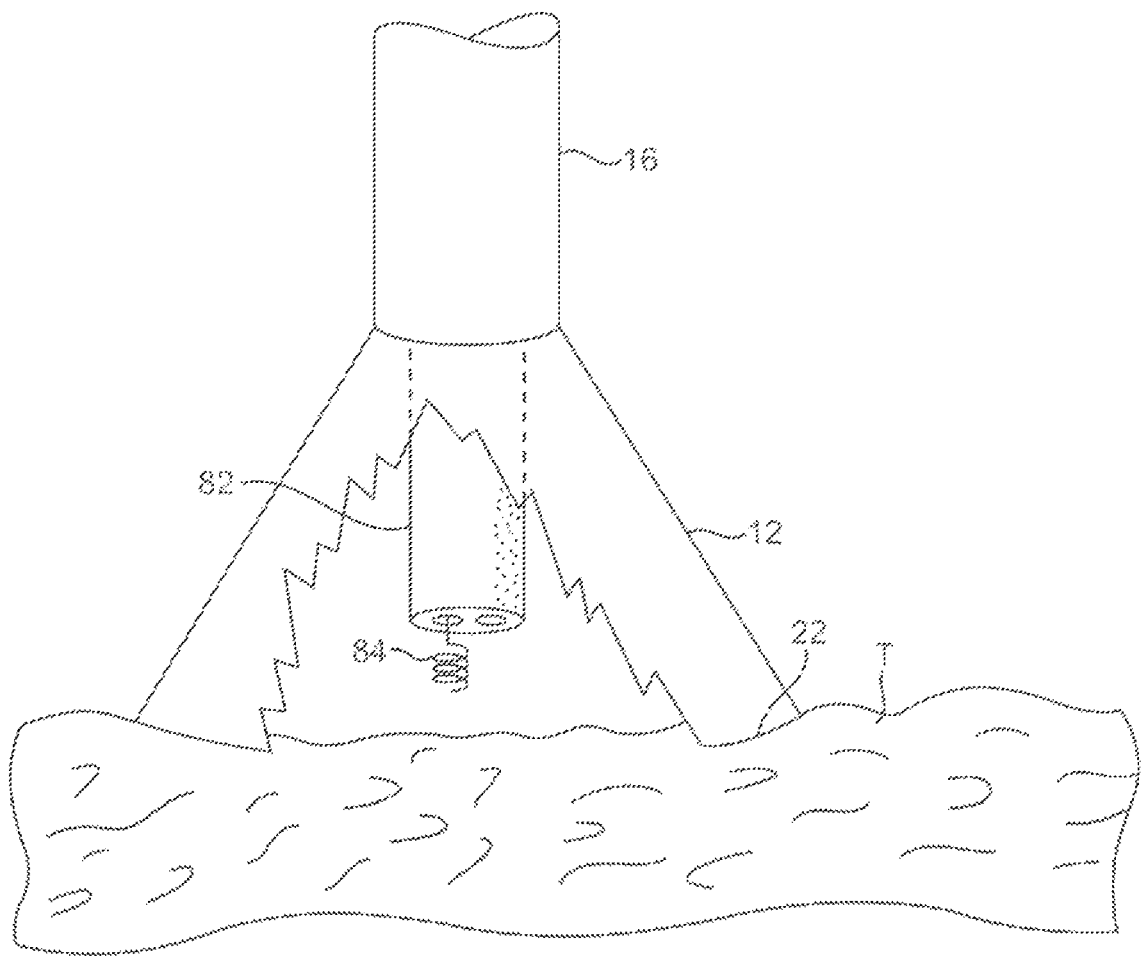
FIGS. 7A and 7B illustrate a variation of an anchoring mechanism such as a helical tissue piercing device for temporarily stabilizing the imaging hood relative to a tissue surface.
Figure 7B:
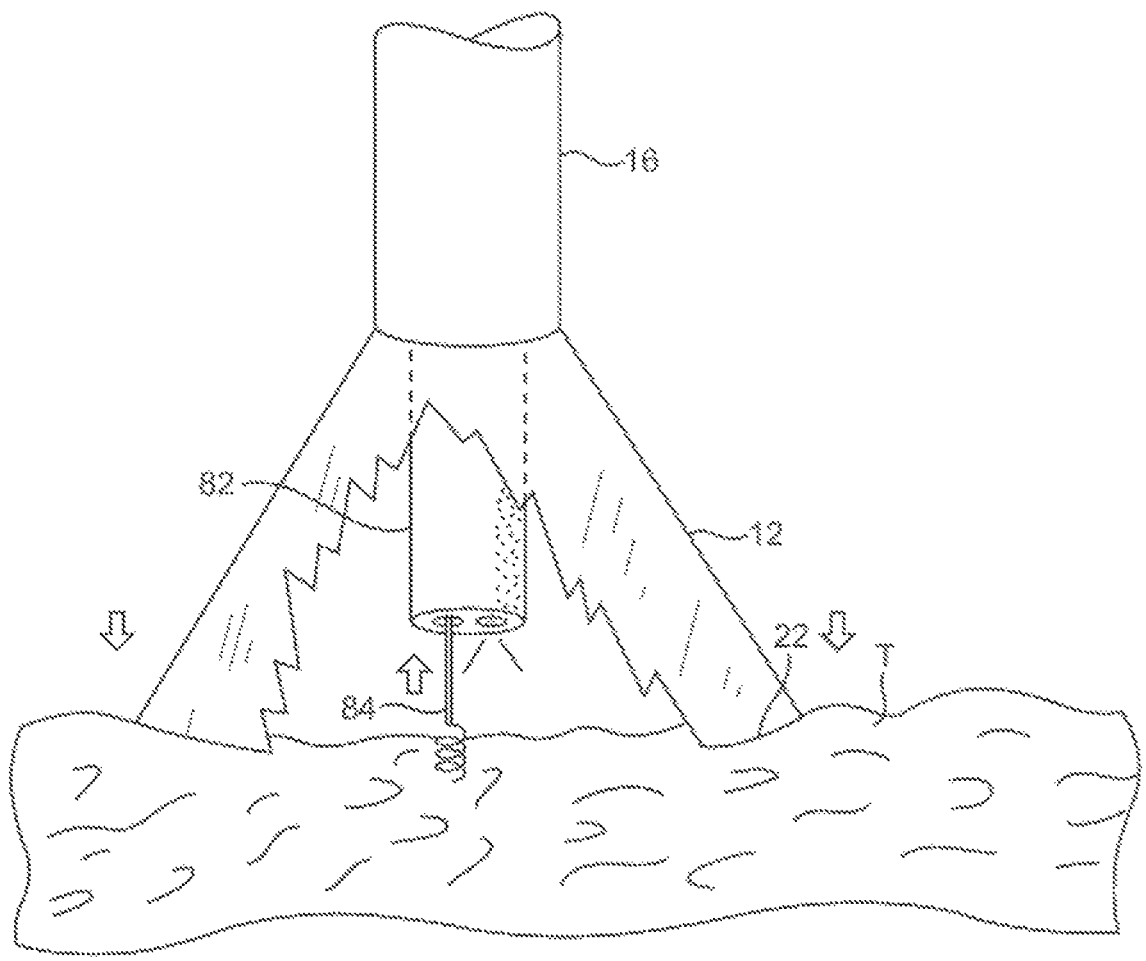

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, anchoring mechanisms such as a helical tissue piercing device 84 may be passed through the tool delivery catheter 82, as shown in FIG. 7A, and into imaging hood 12.

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7B, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. After a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
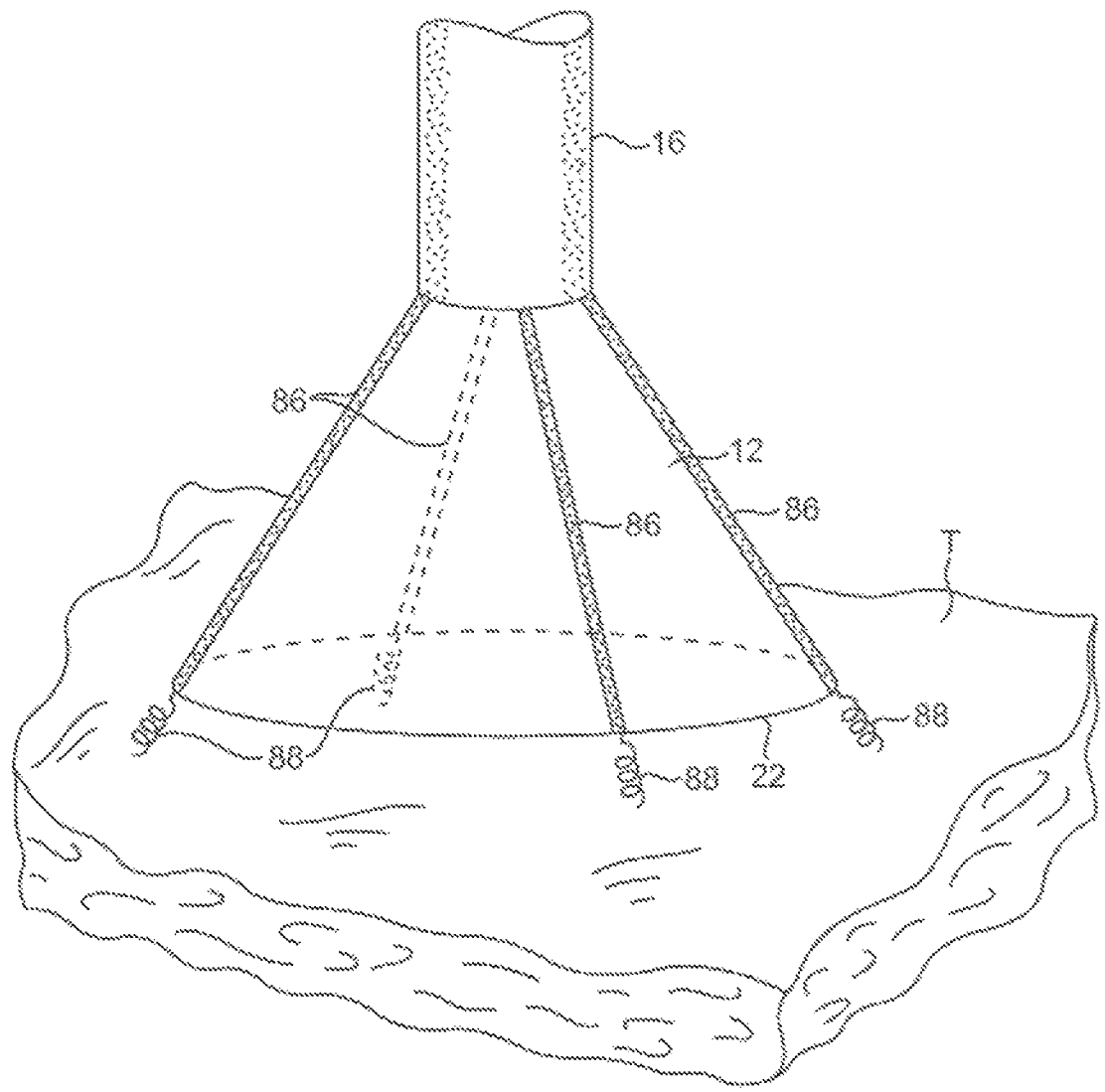
FIG. 7C shows another variation for anchoring the imaging hood having one or more tubular support members integrated with the imaging hood; each support members may define a lumen therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
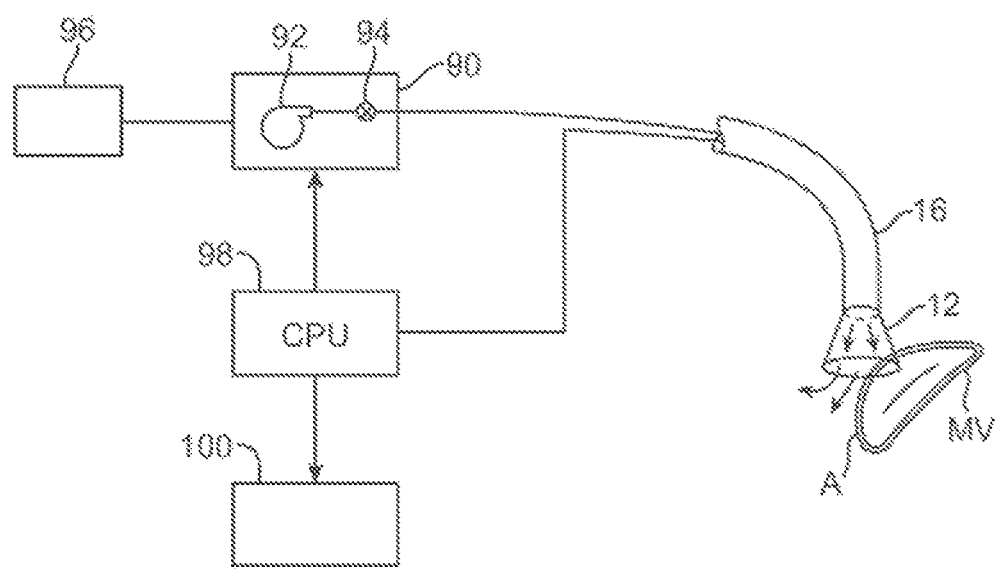
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
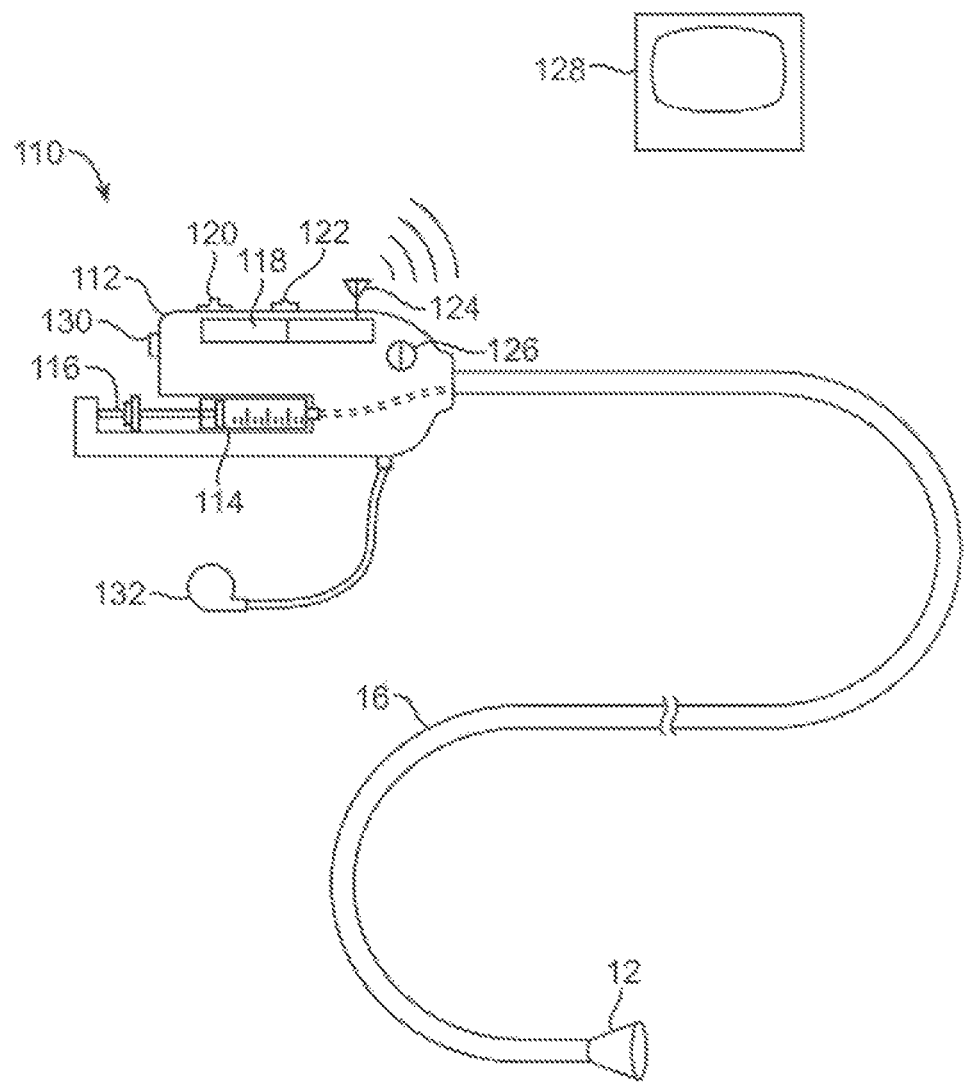
FIG. 8B shows a further illustration of a hand-held variation of the fluid delivery and tissue manipulation system.

FIG. 8B shows a further illustration of a hand-held variation of the fluid delivery and tissue manipulation system 110. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG, Inc., Bellevue, Wash.), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16. Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
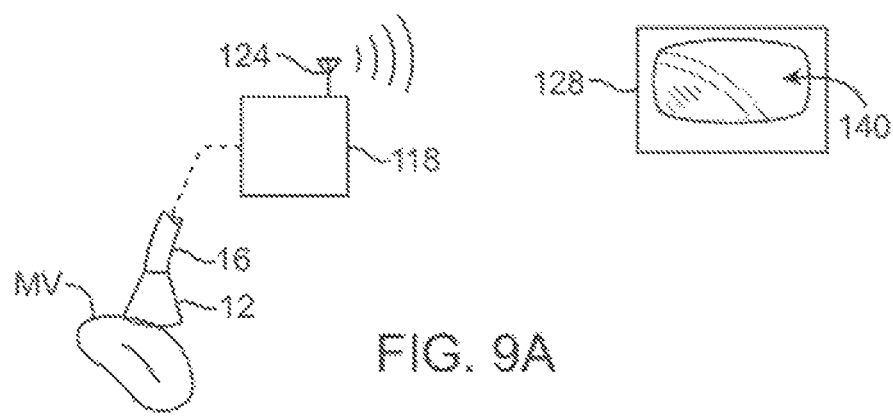
FIGS. 9A to 9C illustrate an example of capturing several images of the tissue at multiple regions.
Figure 9B:
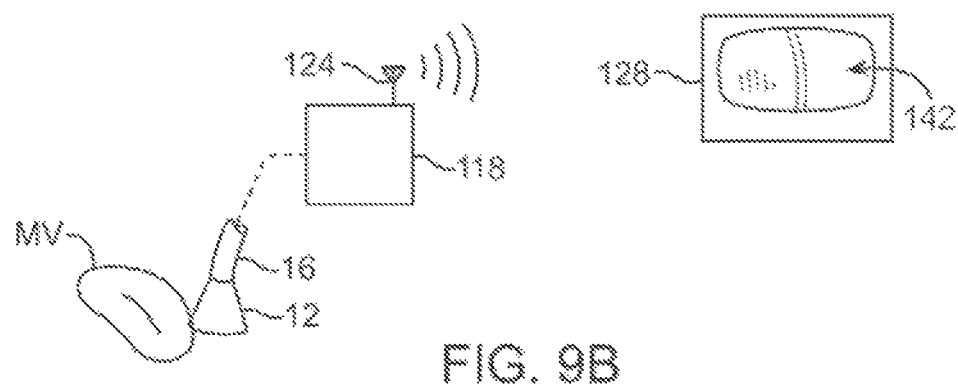
Figure 9C:
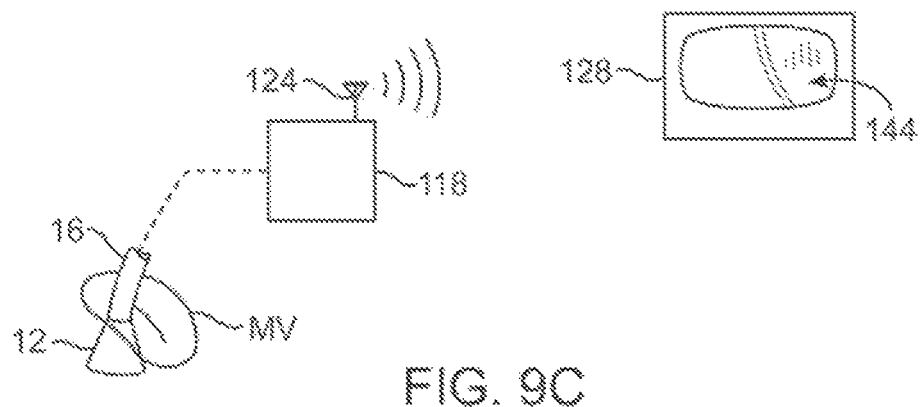

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 140 may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10A:
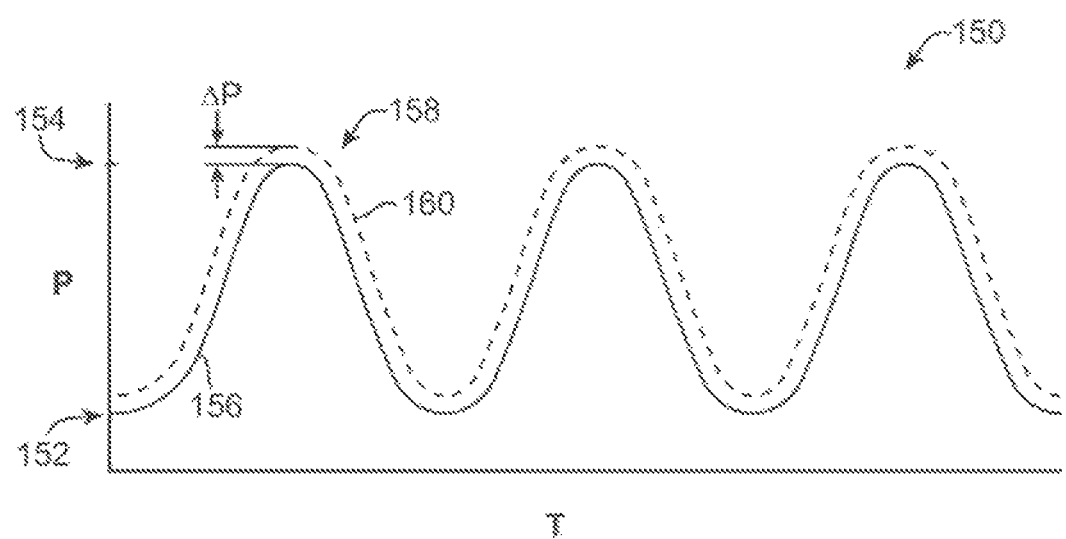
FIGS. 10A and 10B show charts illustrating how fluid pressure within the imaging hood may be coordinated with the surrounding blood pressure; the fluid pressure in the imaging hood may be coordinated with the blood pressure or it may be regulated based upon pressure feedback from the blood.

One example is shown in FIG. 10A which shows a chart 150 illustrating how fluid pressure within the imaging hood 12 may be coordinated with the surrounding blood pressure. Chart 150 shows the cyclical blood pressure 156 alternating between diastolic pressure 152 and systolic pressure 154 over time T due to the beating motion of the patient heart. The fluid pressure of the imaging fluid, indicated by plot 160, within imaging hood 12 may be automatically timed to correspond to the blood pressure changes 160 such that an increased pressure is maintained within imaging hood 12 which is consistently above the blood pressure 156 by a slight increase $\Delta P$, as illustrated by the pressure difference at the peak systolic pressure 158. This pressure difference, $\Delta P$; may be maintained within imaging hood 12 over the pressure variance of the surrounding blood pressure to maintain a positive imaging fluid pressure within imaging hood 12 to maintain a clear view of the underlying tissue. One benefit of maintaining a constant $\Delta P$ is a constant flow and maintenance of a clear field.

Figure 10B:
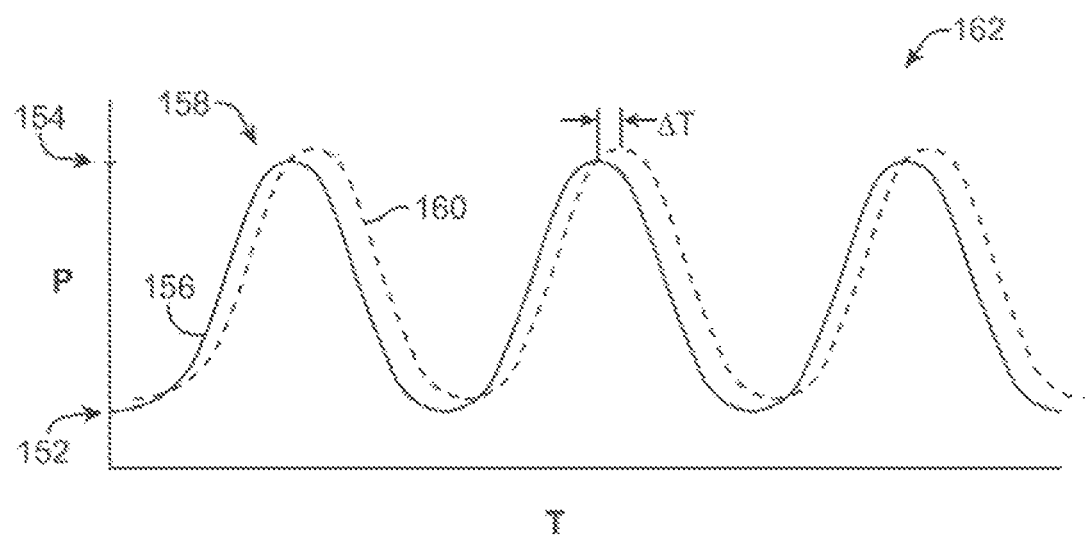

FIG. 10B shows a chart 162 illustrating another variation for maintaining a clear view of the underlying tissue where one or more sensors within the imaging hood 12, as described in further detail below, may be configured to sense pressure changes within the imaging hood 12 and to correspondingly increase the imaging fluid pressure within imaging hood 12. This may result in a time delay, $\Delta T$, as illustrated by the shifted fluid pressure 160 relative to the cycling blood pressure 156, although the time delays $\Delta T$ may be negligible in maintaining the clear image of the underlying tissue. Predictive software algorithms can also be used to substantially eliminate this time delay by predicting when the next pressure wave peak will arrive and by increasing the pressure ahead of the pressure wave's arrival by an amount of time equal to the aforementioned time delay to essentially cancel the time delay out.

The variations in fluid pressure within imaging hood 12 may be accomplished in part due to the nature of imaging hood 12. An inflatable balloon, which is conventionally utilized for imaging tissue, may be affected by the surrounding blood pressure changes. On the other hand, an imaging hood 12 retains a constant volume therewithin and is structurally unaffected by the surrounding blood pressure changes, thus allowing for pressure increases therewithin. The material that hood 12 is made from may also contribute to the manner in which the pressure is modulated within this hood 12. A stiffer hood material, such as high durometer polyurethane or Nylon, may facilitate the maintaining of an open hood when deployed. On the other hand, a relatively lower durometer or softer material, such as a low durometer PVC or polyurethane, may collapse from the surrounding fluid pressure and may not adequately maintain a deployed or expanded hood.

In further controlling the flow of the purging fluid within the hood 12, various measures may be taken in configuring the assembly to allow for the infusion and controlled retention of the clearing fluid into the hood. By controlling the infusion and retention of the clearing fluid, the introduction of the clearing fluid into the patient body may be limited and the clarity of the imaging of the underlying tissue through the fluid within the hood 12 may be maintained for relatively longer periods of time by inhibiting, delaying, or preventing the infusion of surrounding blood into the viewing field.

In utilizing the hood 12 and various instruments through the hood for tissue treatment, hood 12 may be articulated in a variety of configurations to facilitate the access to regions within the heart. For instance, access to the left atrium of a patient's heart for performing treatments such as tissue ablation for atrial fibrillation may require hood 12 to be retroflexed in various configurations to enable sufficient access. Thus, the ability to control the steering or articulation of hood 12 within the patient's heart may facilitate tissue visualization and treatment.

Further examples of the visualization catheter assembly as well as methods of use are described in further detail in U.S. Pat. Pub. 2006/0184048 A1, which is incorporated herein by reference in its entirety.

When ablating the underlying visualized tissue, a number of instruments may be utilized for performing the ablation upon the tissue, e.g., advancing an ablation probe through the hood and into ablative contact with the tissue while under direct visualization. Yet because an ablative probe is surrounded by the purging fluid, such as saline, which is already utilized for visualizing through to the underlying tissue, the conductive properties of the fluid may be taken advantage of by passing electrical currents directly through the fluid itself to the underlying tissue. Thus, tissue regions which are directly imaged through the fluid within the imaging hood 12 may be ablated via electrical energy conducted through the fluid without the need for a separate ablation probe or instrument.

Figure 11:
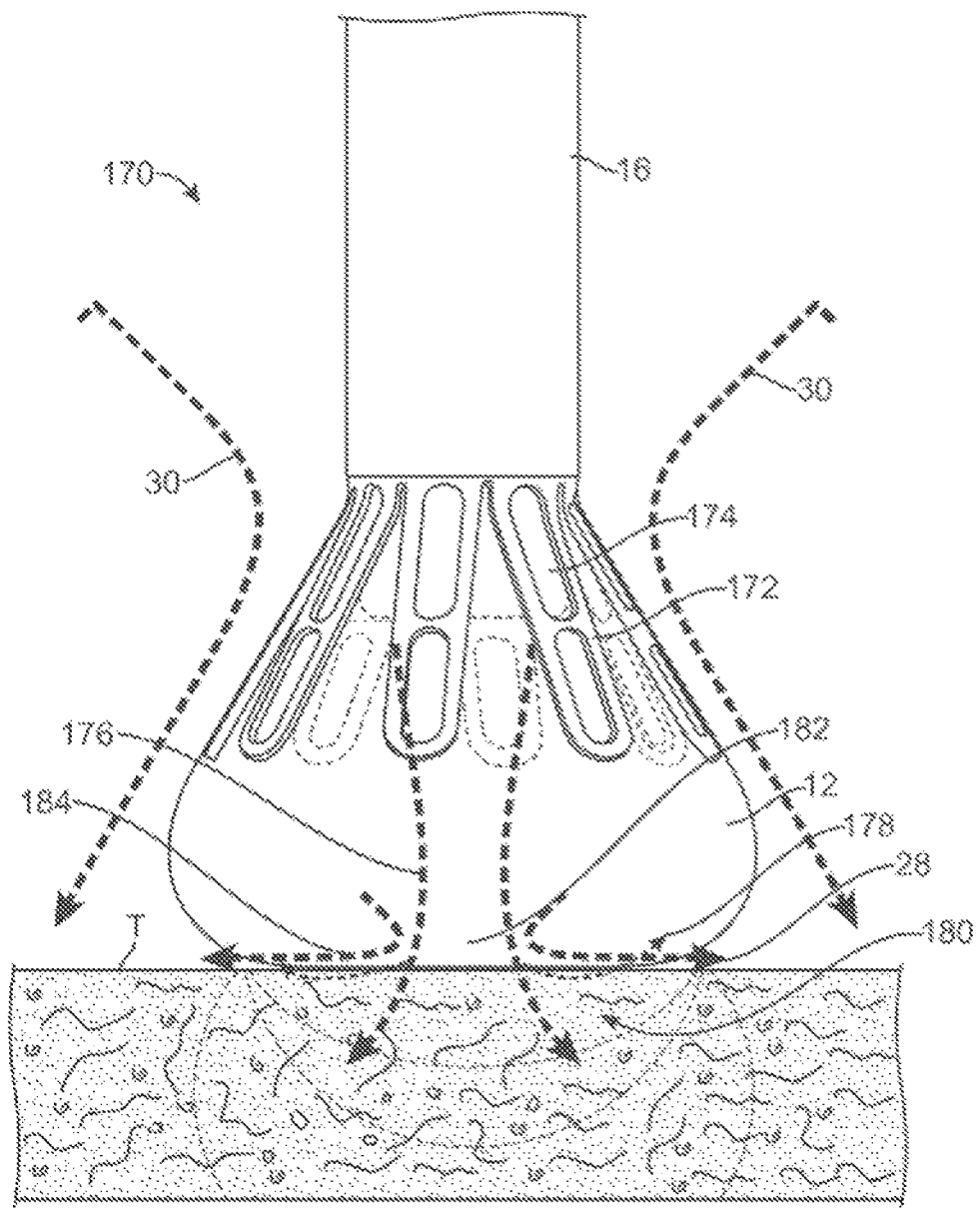
FIG. 11 illustrates a side view of an example of an imaging hood configured to ablate contacted tissue under visualization via one or more electrodes transmitting energy through the electrolytic purging fluid and into and through the underlying tissue.

FIG. 11 illustrates a side view of an example of such a visual electrode assembly 170 which may visualize the underlying tissue T in a manner, as described above. With the hood 12 positioned upon the tissue surface and the clearing fluid 178, such as saline, introduced into the hood interior to purge the bodily fluids 28 such as blood out of the hood 12, the underlying tissue may be visualized directly. In this example, a separate RF electrode 174 may be positioned through deployment catheter 16 to reside at least partially within hood 12 such that electrode 174 is in electrical contact with the purging fluid 178. Alternatively, electrode 174 need not reside within hood 12 at all but may be positioned more proximally of hood 12 within or along the catheter (or even reside within or along the handle) provided that electrode 174 is in electrical communication with the purging fluid 178 when the fluid 178 is introduced through hood 12. In yet other alternatives, electrode 174 may be introduced as an instrument separate from the deployment catheter 16 and handle altogether. In other variations, one or more of the support struts 172 may be optionally utilized as the discharging electrode, as described below in further detail.

As the purging fluid 178 passes through an aperture 182 defined over the distal membrane 184 which may cover the distal opening of hood 12, energy 176 may be discharged from electrode 174 such that it passes through the saline, which is electrolytic in nature, and is delivered directly to the visualized tissue visible through aperture 182 to ablate the underlying tissue 180. Further examples of such hood structures having apertures are shown and described in further detail in U.S. patent application Ser. No. 11/763,399 filed Jun. 14, 2007, which is incorporated herein by reference in its entirety.

As the visualized tissue is ablated 180 within the visualization field (alternatively called a therapy field), hood 12 may advantageously isolate the ablation site from surrounding blood 30 and may also contain the discharged energy 176 within hood 12 such that the amount of electrical energy delivered to the tissue is optimized and is not lost to any blood flow. Moreover, the saline fluid passing into the body from hood 12 through aperture 182 may additionally form a thin layer of saline flowing across the tissue to hood interface to provide cooling of the surrounding tissue surfaces.

Figure 12:
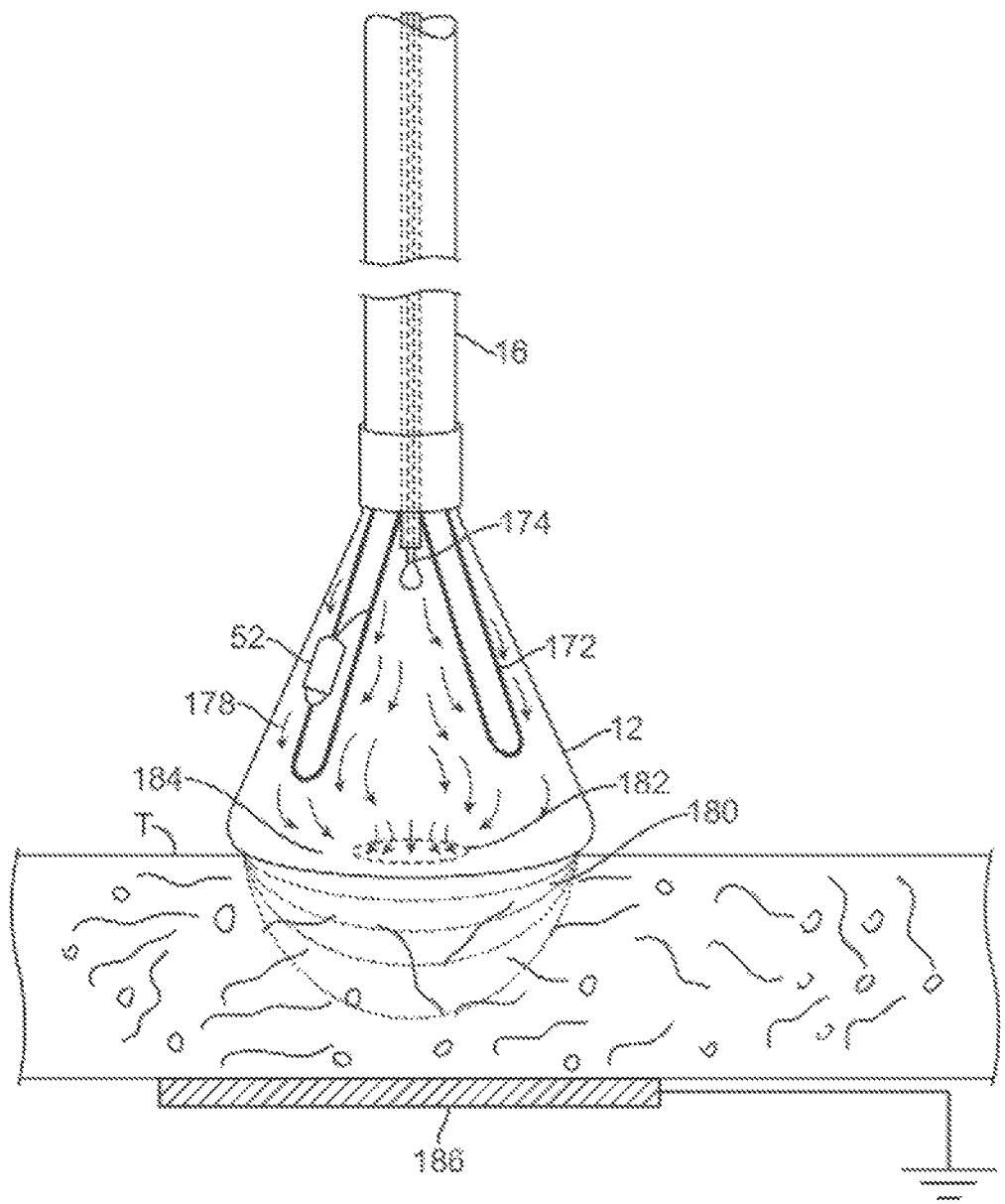
FIG. 12 shows a side view of another variation of the tissue visualization catheter ablating the underlying visualized tissue via a monopolar electrode assembly transmitting energy through the purging fluid.

FIG. 12 illustrates a further variation of the visual electrode assembly where the discharging electrode 174 is positioned within hood 12 distally of deployment catheter 16 and within the saline filled environment of hood 12. Imaging element 52 is illustrated positioned along an inner surface of hood 12 for visualizing the underlying tissue below, as described above. In this variation, the visual electrode 174 assembly is configured as a monopolar electrode. Thus, grounding plate 186 may be placed in contact along an exterior skin surface of the patient's body to provide a return electrode for the ablation energy 180 flowing into the underlying tissue.

Figure 13:
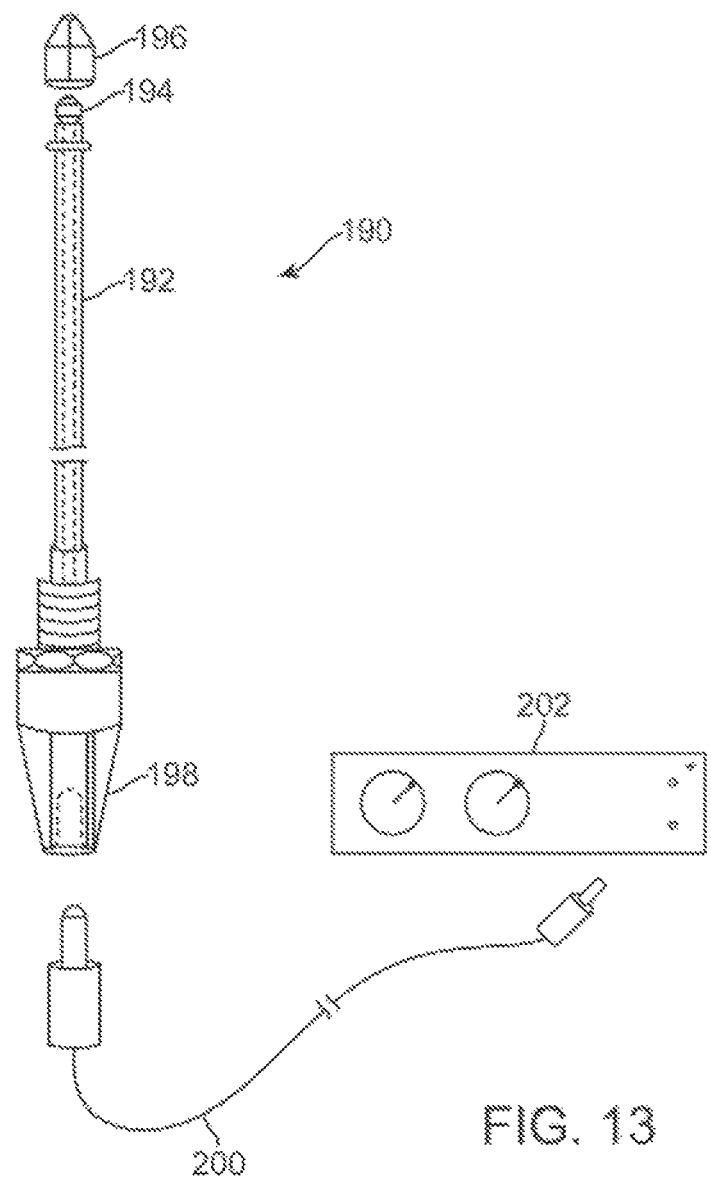
FIG. 13 shows an assembly view of an example of an electrode assembly connectable to an ablation generator and positionable at least partially through the hood.

As mentioned, the discharging electrode may comprise a conventional ablation electrode. In other variations, it may be specifically configured for discharging RF energy through an electrolytic fluid environment. The example illustrated in FIG. 13 shows an assembly view of electrode assembly 190 which generally comprises an electrode shaft 192 extending from a proximal connector 198 and ending in a distal tip 194. Electrode shaft 192 may be fabricated from various electrically conductive materials such as copper, stainless steel, Nitinol, silver, gold, platinum, etc. which is covered with an insulative coating such as PET, latex, or other biocompatible polymers, etc. A conductive tip 196 may define a low profile segment fabricated from or plated with a similar conductive material and can adopt the shape of a sphere, dome, cylinder or other desirable three-dimensional configuration configured to optimize the distal segment's surface area in contact with the distal tip 194 as well as the surrounding electrolytic fluid. The proximal connector 198 may be coupled to a cable 200 which is connectable, e.g., via a banana plug, etc., to an ablation energy generator 202. In use, the conductive tip 196 may be positioned within the hood 12 distally of deployment catheter 16 and spaced away from the underlying tissue to be ablated such that direct contact between the tip 196 and tissue does not occur, although direct ablation via contact may also be accomplished if so desired.

Figure 14:
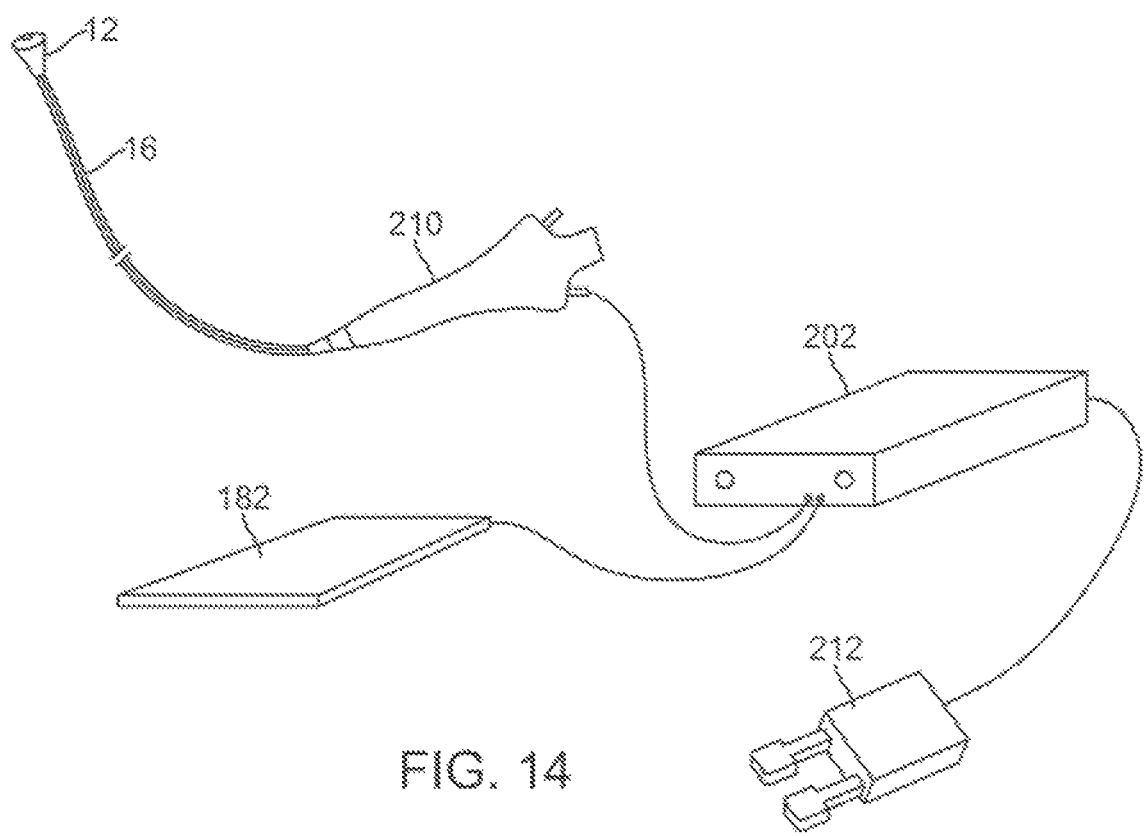
FIG. 14 illustrates an assembly view of one example of a visualization system configured for ablation through the purging fluid utilizing a monopolar electrode assembly.

As illustrated in the assembly view of FIG. 14, hood 12 and deployment catheter 16 may be coupled to handle 210, through which the electrode may be coupled to the energy generator 202. The example illustrated shows a monopolar ablation configuration and thus includes grounding plate 182 also electrically coupled to generator 202. A separate actuation assembly 212, e.g., foot pedal, may also be electrically coupled to generator 202 to allow for actuation of the ablation energy. Upon filling the hood 12 with saline and obtaining a clear view of the tissue region of interest, the RF ablation energy generator 202 can be activated via actuation assembly 212 to initiate the flow of electrical currents to be transmitted from the generator 202 and through the purging fluid, e.g., saline, via the electrode to electrically charge the saline within the imaging hood 12. The saline within the hood 12 may function as a visual electrode to channel the RF energy into the tissue that is in contact with the saline, subsequently ablating said tissue with the RF energy. Hypersalinity saline with higher concentration of salts can also be used to improve the conductivity of the visual electrode system.

Accordingly, the tissue visualization and manipulation catheter with visual electrode described herein provides a platform to perform tissue ablation under direct real time in vivo visualization of the tissue before, during, and after an ablation process. Moreover, the purging fluid (such as saline) introduced into the imaging hood may possess the dual functions of clearing the field of view within the hood 12 and of providing a medium for ablating tissue in contact such that the visualized tissue may be ablated effectively and uniformly over a larger region of tissue than possible with a conventional ablation electrode which typically ablates through direct tissue contact with a probe.

As the assembly allows for ablation of tissue directly visualized through hood 12, FIG. 15 illustrates an example of a system configured for enabling dual visualization and ablation. As shown in ablation assembly 220, hood 12 and deployment catheter 16 are coupled to handle 210, as previously described. Fluid reservoir 222, shown in this example as a saline-filled bag reservoir, may be attached through handle 210 to provide the clearing fluid and ablation medium. An optical imaging assembly 226 coupled to an imaging element positioned within or adjacent to hood 12 may extend proximally through handle 210 and be coupled to imaging processor assembly 224 for processing the images detected within hood 12. Assembly may also be coupled to a video receiving assembly 228 for receiving images from the optical imaging assembly 226. The video receiving assembly 228 may in turn be coupled to video processor assembly 230 which may process the detected images within hood 12 for display upon video display 232. Also shown are grounding plate 182 and ablation energy generator 202 which is coupled to ablation electrode within or proximate to hood 12, as previously described.

In use, as hood 12 is placed against the tissue region to be visualized and treated, as shown in the perspective view of FIG. 16A, visual confirmation of the desired tissue surface T or feature can be provided by the tissue visualization catheter via the imaging element. Upon visual confirmation, ablation generator 202 may be activated to ablate tissue exposed through a central aperture 240 having a diameter, e.g., 3 mm, defined in a distal membrane 242 extending over hood 12 as shown in the end view of FIG. 16B. The underlying tissue T may thus be ablated via the electrically charged purging fluid while still maintaining visual contact of the tissue T. As illustrated in the perspective view of FIG. 16C, a resulting lesion 180, such as a circularly-shaped lesion as illustrated, upon the tissue T approximating the size and shape of the aperture 240 can be accordingly formed because the flow reduction aperture 240 may effectively isolate the tissue region to be ablated to the area exposed to the fluid through aperture 240. Lesion size and shape can thus be modified by varying the size and the shape of the aperture at the distal face of the hood 12 where a relatively sufficient seal is formed between the aperture 240 and underlying tissue T to be treated.

In other treatment variations where a seal between the aperture and tissue surface is not formed tightly, as illustrated in the perspective and end views of FIGS. 16D and 16E, the lesion formed upon the tissue may approximate the diameter and size of the entire hood 12 itself rather than the size of aperture 240. FIG. 16E shows an end view of hood 12 having an overall diameter D which is larger than aperture 240. When placed upon the tissue and the purging fluid is introduced into hood 12, the saline fluid may seep through aperture 240 while purging the blood from within hood 12 as well from any space formed between the distal membrane 242 and the tissue surface within the confines of the hood diameter D. With the blood purged by the saline fluid, ablation energy may be actuated such that the energy flows through the fluid and into the space underlying aperture 240 and distal membrane 242. The resulting lesion 180' formed upon the tissue, as illustrated in FIG. 16F, may approximate the larger diameter D of hood 12 which is larger than the lesion formed through just aperture 240. Distal membrane 242, in this example, may thus act to isolate the tissue region directly beneath hood. 12 for lesion formation.

The relative differences between the area of the aperture and the area of distal membrane may be varied depending upon the desired lesion size as well as the tissue region to be treated. In some variations, the area of the distal membrane (or hood diameter in contact against the tissue surface) may be at least twice as large as the cross sectional area of the deployment catheter or of the aperture.

Figure 17:
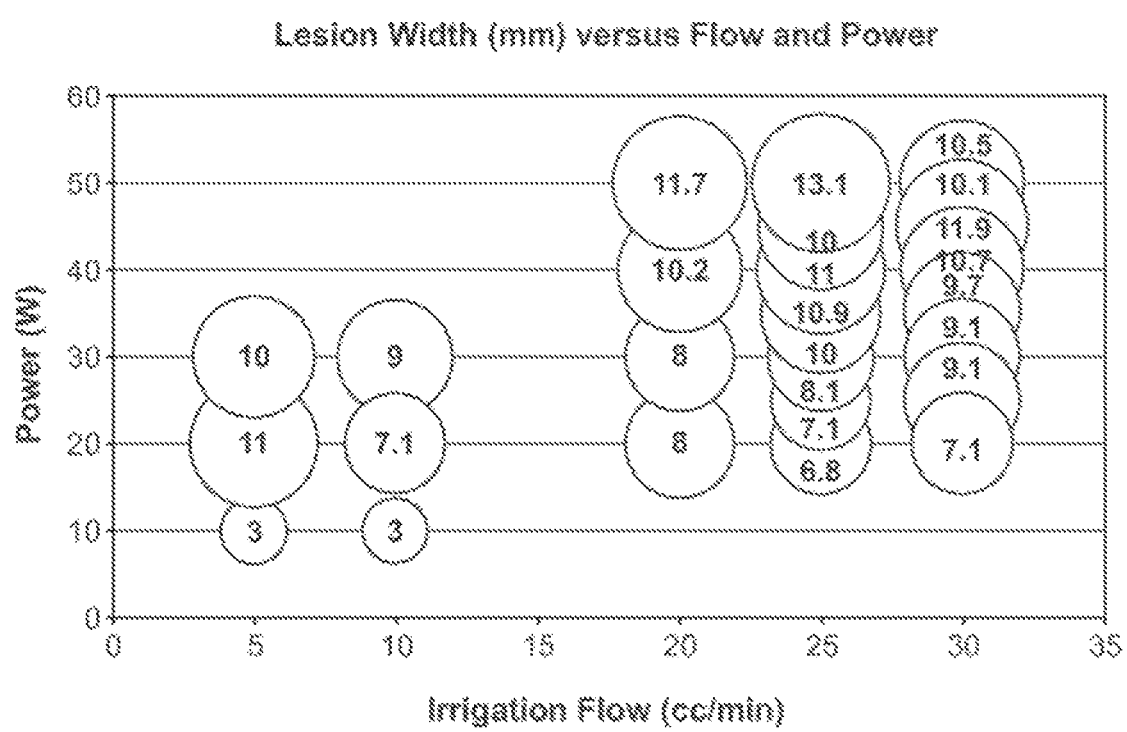
FIG. 17 shows a chart illustrating resultant lesion sizes formed during ablation treatment at various power levels and flow rates of the purging fluid.

Aside from aperture size and shape, other parameters which may be varied to adjust the ablative effects of the electrode may also include parameters such as the amount of power as well as the rate of purging fluid infusion (or irrigation flow) into hood 12. FIG. 17 illustrates a chart illustrating the resulting lesion widths (measured in millimeters) at specified irrigation flow rates (measured in cc/min) versus the amount of applied power (measured in Watts) through the discharging electrode. To produce the results, an imaging hood 12 was coupled to an irrigation pump and an RF energy generator (Stockert 70 RF Generator). The irrigation flow rate through the hood 12 was initially set at 15 cc/min and the RF power was initially set at 25 W for a predetermined duration time of, e.g., 60 sec. As the purging saline fluid was introduced into hood 12, ablation energy was actuated. If the underlying tissue did not generate any popping or produce any bubbles (which may be indicative of an impending endocardial eruption), the RF power was increased by 2 W and the ablation was repeated. If bubbles or popping did occur, the RF power was decreased by 2 W and the ablation was repeated. Generally, as illustrated in the chart, relatively higher irrigation flow rates (e.g., 25 cc/min) and relatively higher power levels (e.g., 50 W) produced relatively larger ablative lesions upon the underlying tissue.

Figure 18A:
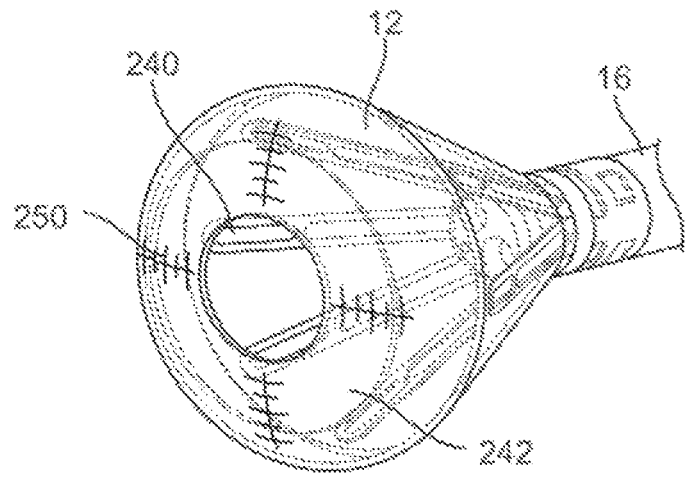
FIG. 18A illustrates a perspective view of an example of a visualization catheter which defines a number of gradations over a distal membrane for estimating the size of ablated lesions and other anatomical features under direct visualization.
Figure 18B:
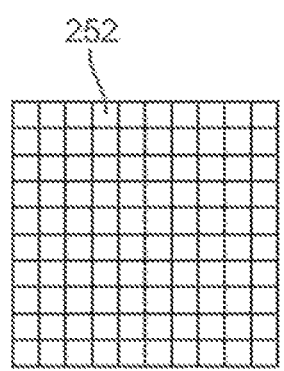
FIGS. 18B and 18C illustrate other examples of gradations which may be placed upon the distal membrane to facilitate visual estimation of lesion size.
Figure 18C:
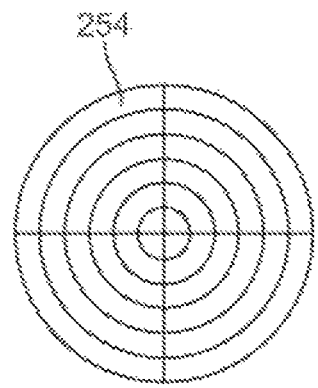

Once an ablation procedure has begun or has been completed, the resulting lesion size may generally approximate the aperture opening. However, in determining the size of multiple lesions or a relatively large lesion, visually estimating the size may be difficult through hood 12. Thus, one or more gradations 250 or markings may be placed upon the distal membrane 242 of hood 12 to allow for the visual measurement of underlying lesions or other anatomical features which may be imaged through hood 12. FIG. 18A shows a perspective view of one example of hood 12 having gradations 250 radially positioned upon membrane 242 much like a reticle. Other patterns or markings such as a grid patterned scale 252 or a concentric annular pattern 254, as shown respectively in FIGS. 18B and 18C, may be defined upon hood 12 or membrane 242.

Figure 19A:
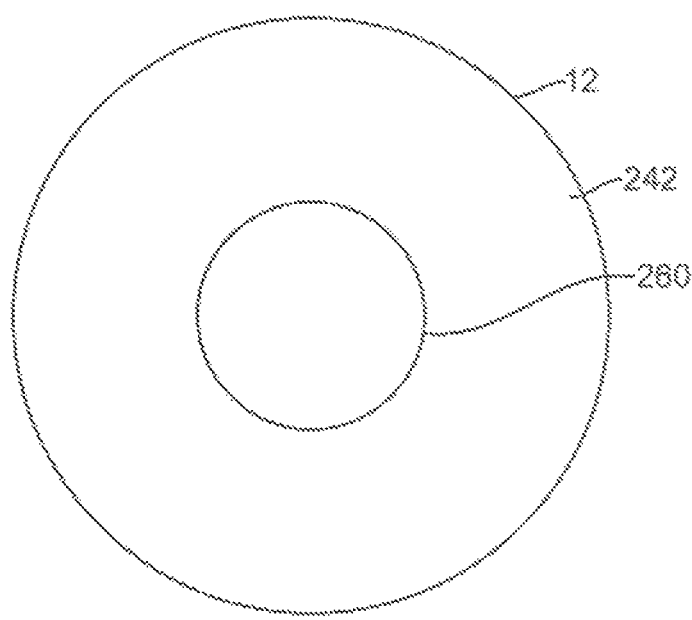
FIG. 19A shows another example of a distal membrane over the distal end of the hood defining a central aperture through which underlying tissue is visualized and ablated through the purging fluid.
Figure 19B:
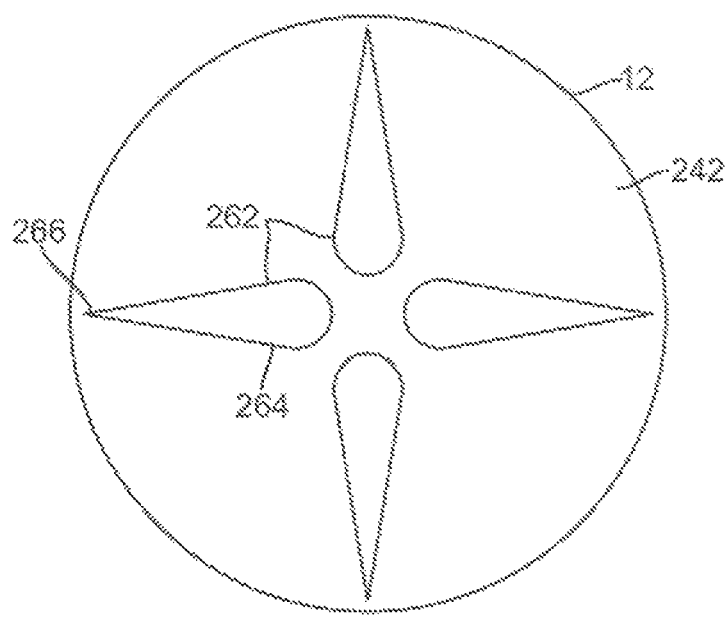
FIG. 19B shows another example of multiple apertures defined over the membrane in the shape of uniformly spaced apertures which taper radially.

Returning to aperture size and shape in forming lesions upon the tissue surface, generally, the smaller the tissue surface area exposed through the aperture to the ablative fluid, the higher the relative ablation current density at the exposed tissue and the deeper the lesion formed into the tissue. The distance between the electrode and the underlying tissue may also contribute to the energy distribution through the tissue. As the electrode is closer to the tissue surface, the energy transfer is improved yet the farther away from the tissue surface, the more even the distribution of the energy transfer upon the tissue and the resulting lesion. However, placement of the electrode at too far a distance from the tissue may result in overheating of the saline fluid. Thus, a balance between electrode positioning and aperture size, shape, and/or placement may be utilized as parameters for tissue ablation. FIG. 19A illustrates an end view of hood 12 having a distal membrane 242 formed over the opening of hood 12 and defining a central aperture 260 having a diameter of, e.g., 3 mm, with a hood 12 having an outer diameter of, e.g., 8 mm. FIG. 19B illustrates another variation having multiple, e.g., four, uniformly spaced tapered tear-drop shaped apertures 262 each having a widened first end 264 and a tapered second end 266 extending radially from the center of hood 12. Because the density of the discharged energy is higher at relatively smaller exposed areas, the discharged ablative energy may be uniformly maintained along the length of each aperture 262 as the higher energy density may offset the increased radial distance from the discharging electrode to result in a uniformly ablated lesion.

Figure 19C:
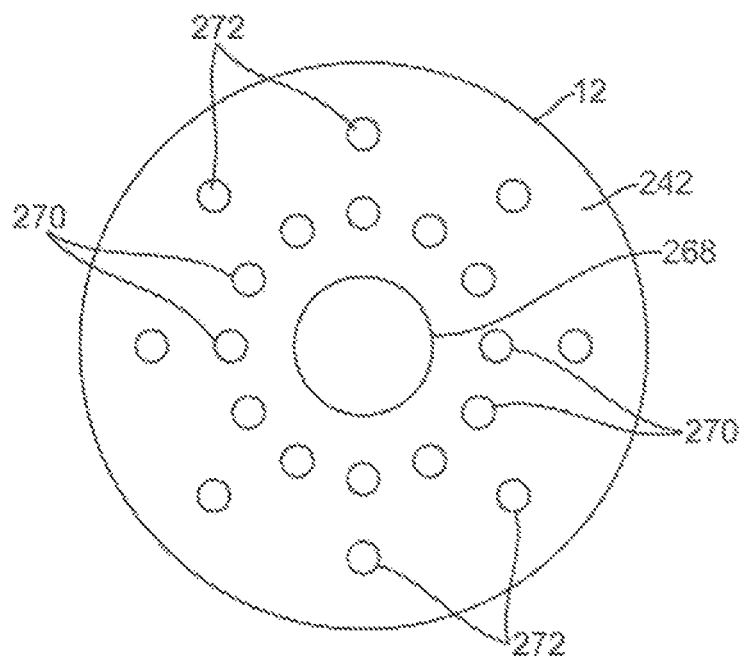
FIG. 19C shows another example of a central aperture surrounded circumferentially by multiple smaller apertures.
Figure 19D:
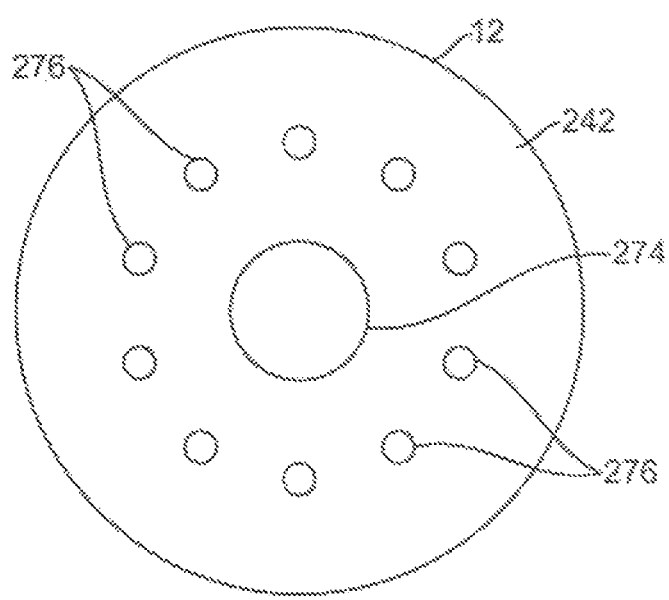
FIG. 19D shows yet another example of a central aperture surrounded circumferentially by a multiple smaller apertures.

Another multiple aperture variation is shown in the end view of FIG. 19C, which illustrates a central aperture 268 having a diameter of, e.g., 2 mm, with a plurality of secondary apertures 270 (e.g., twelve apertures) each having a diameter of, e.g., 0.5 mm, spaced annularly at a first radius over membrane 242. An additional plurality of tertiary apertures 272 (e.g., eight apertures) each also having a diameter of, e.g., 0.5 mm, and spaced annularly at a second radius over membrane 242 may also be defined over membrane energy 242. Yet another variation is shown in the end view of FIG. 19D which illustrates a central aperture 274 having a diameter of, e.g., 2 mm, and a plurality of secondary apertures 276 each having a diameter of, e.g., 0.5 mm, spaced annularly at a first radius.

Figure 20A:
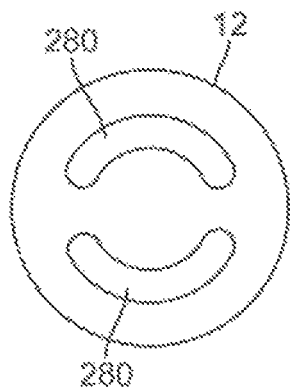
FIGS. 20A and 20B show an end view of a hood having semicircular-shaped apertures and the resulting lesion formed upon the treated tissue, respectively.
Figure 20B:
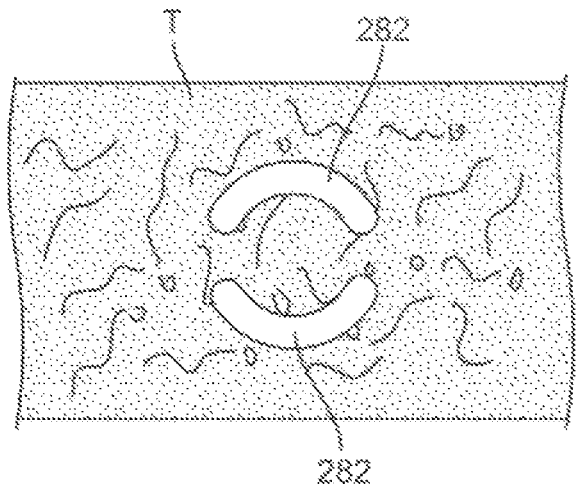
Figure 21A:
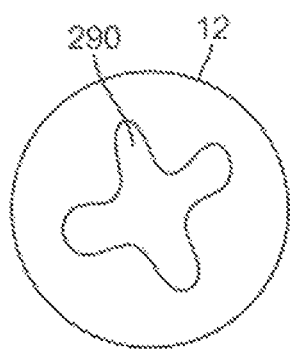
FIGS. 21A and 21B show an end view of another hood having a cross-shaped aperture and the resulting lesion formed upon the treated tissue, respectively.
Figure 21B:
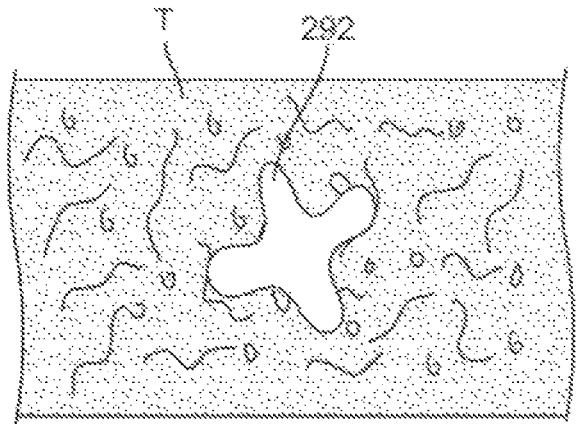

Other configurations for the aperture may also take the form as shown in the end view of hood 12 in FIG. 20A, which illustrates two circumferentially spaced semicircular apertures 280. When a tight seal is established between the aperture and tissue, the resulting lesions through the apertures are illustrated in the correspondingly ablated lesions 282 upon tissue T in FIG. 20B. Alternatively, as shown in the end view of FIG. 21, aperture may be formed as a crossed aperture 290 which may also form a correspondingly crossed lesion 292 upon tissue T in FIG. 21B when a sufficient seal is established between the aperture and tissue. These examples are intended to be illustrative and not limiting such that any variety of alternative aperture shapes and sizes may be utilized as so desired.

Figure 22A:
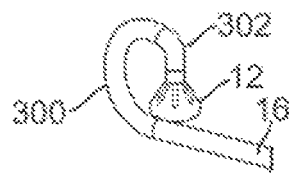
FIGS. 22A to 22C show perspective views of one variation of the visualization catheter with articulation capabilities.
Figure 22B:
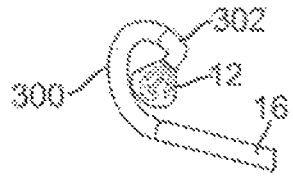
Figure 22C:
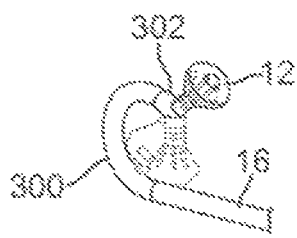

Intravascularly accessing the various tissue regions, e.g., within the various chambers of the heart, a deployment catheter having multiple steering capabilities may be utilized. An example is illustrated in FIGS. 22A to 22C, which show perspective views of a hood 12 attached to a steerable segment of a deployment catheter 16. The steerable segment may generally comprise a proximal steering section 300 configured to articulate within a single plane and a distal steering section 302 coupled distally of steering section 300 and configured to articulate in any number of directions, as shown. Further details of such an articulatable deployment catheter are shown in greater detail in U.S. patent application Ser. No. 12/108,812 filed Apr. 24, 2008, which is, incorporated herein by reference in its entirety. Alternatively, any number of other conventional steering catheters may also be utilized if so desired.

Figure 23B:
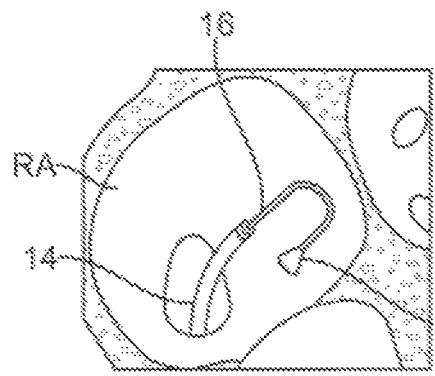
FIGS. 23A to 23D illustrate partial cross-sectional side views of a visualization catheter articulating with a chamber of the heart for visualization and ablation treatment.
Figure 23C:
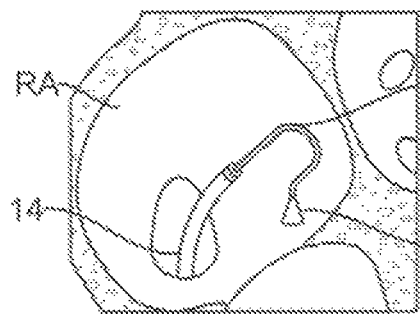
Figure 23D:
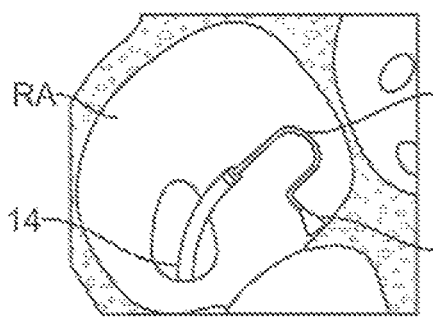
Figure 23A:
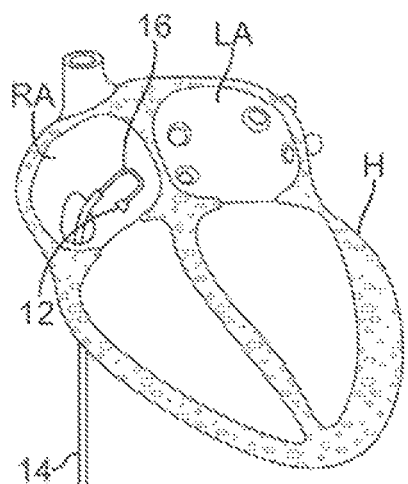

Deployment catheter may be advanced through an outer sheath 14, e.g., through a femoral access route and into the right atrium RA of a patient's heart via the superior vena cava, as illustrated in FIG. 23A. Other intravascular access routes are of course possible and this particular access route is shown for illustrative purposes. In any case, once the deployment catheter having the articulatable segment has been introduced into the heart chamber, the steering sections 300, 302 of catheter 16 may be articulated to position hood 12 against any region of tissue within the chamber for visualization and/or treatment, as illustrated in the partial cross-sectional views of FIGS. 23B to 23D.

Figure 24:
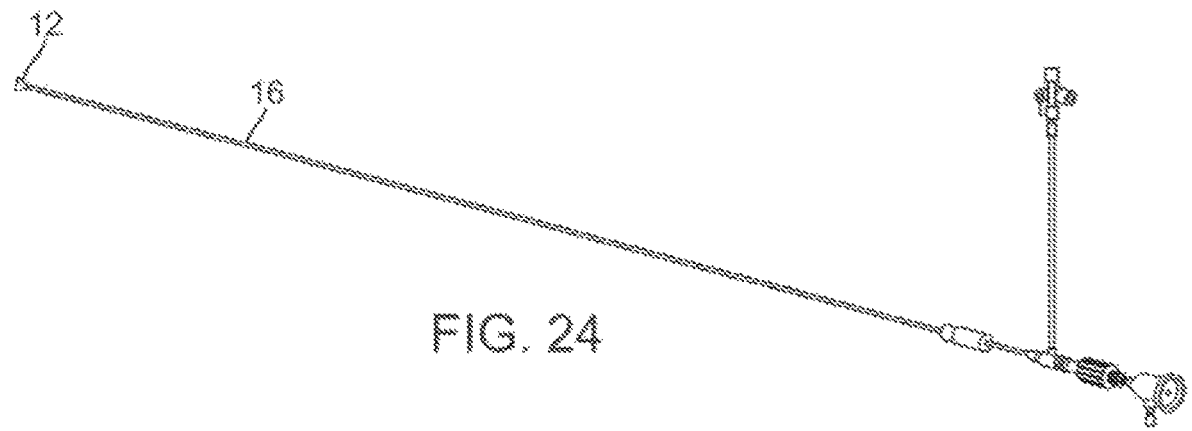
FIG. 24 shows a perspective view of a visualization catheter.
Figure 25B:
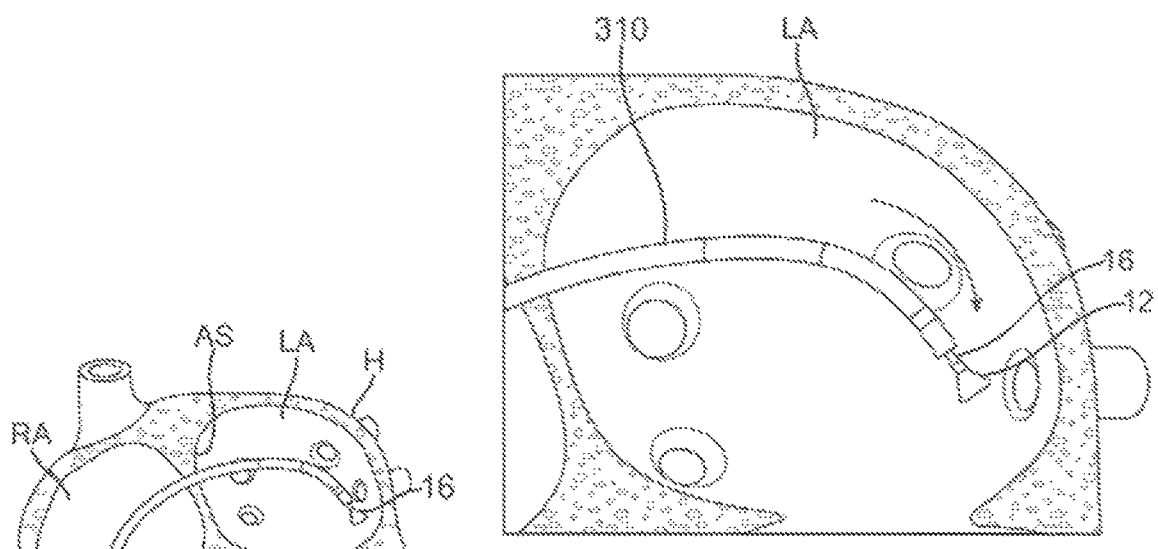
FIGS. 25A and 25B show partial cross-sectional side views of the visualization catheter advanced through and articulated by a steerable sheath.
Figure 25A:
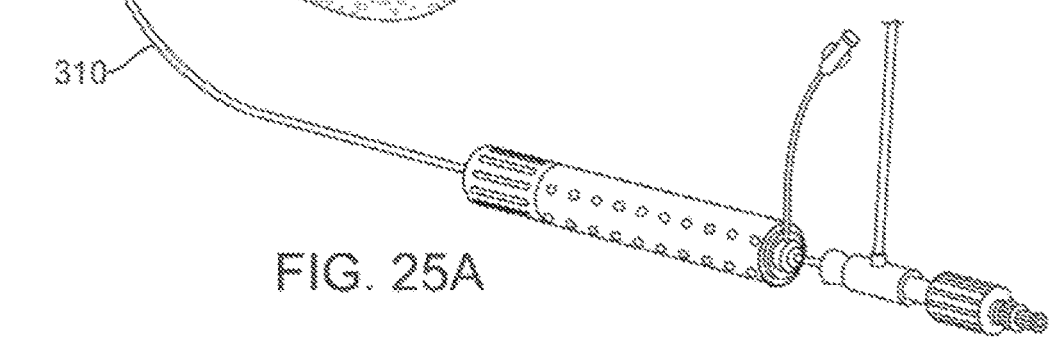

In another variation, a passively steerable hood 12 and deployment catheter 16, as shown in the perspective view of FIG. 24, may be intravascularly introduced into the chambers of the heart, such as the left atrium LA, through a delivery catheter or sheath 310 which may itself be articulatable to control a position of hood 12 within the heart chamber such as the left atrium LA for visualization and/or treatment, as shown in the partial cross-sectional side and detail side views of FIGS. 25A and 25B, respectively. Another variation is illustrated in the partial cross-sectional side and detail side views of FIGS. 26A and 26B, which illustrate a robotically controlled sheath 312 which may articulate an articulatable section 316 of the sheath via one or more control mechanisms 314 to control a position of hood 12 and deployment catheter 16. Further details of such a system are shown and described in detail in U.S. patent application Ser. No. 11/848,429 filed Aug. 31, 2007, which is incorporated herein by reference in its entirety.

Figure 27A:
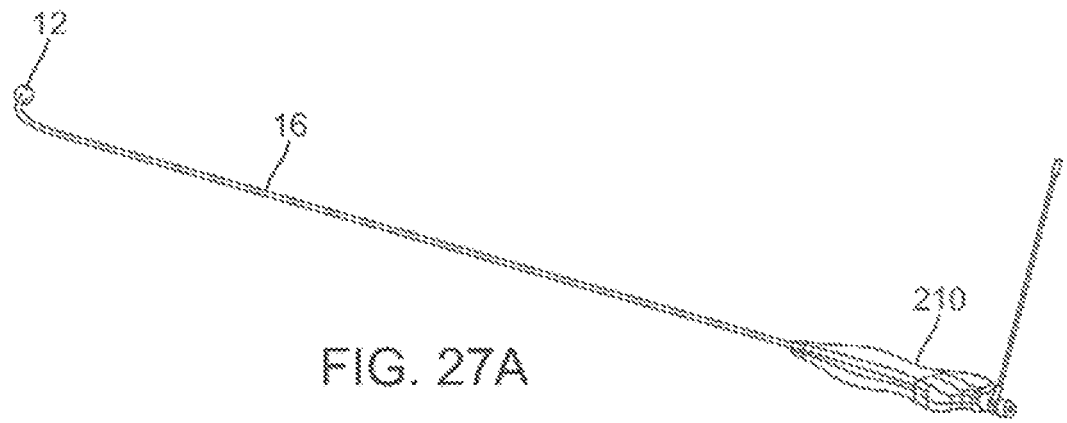
FIGS. 27A to 27C illustrate perspective views of an imaging hood having a number of directional indicators marked upon a distal membrane which correspond to directional indicators placed upon the handle for selective articulation regardless of hood orientation.
Figure 27C:
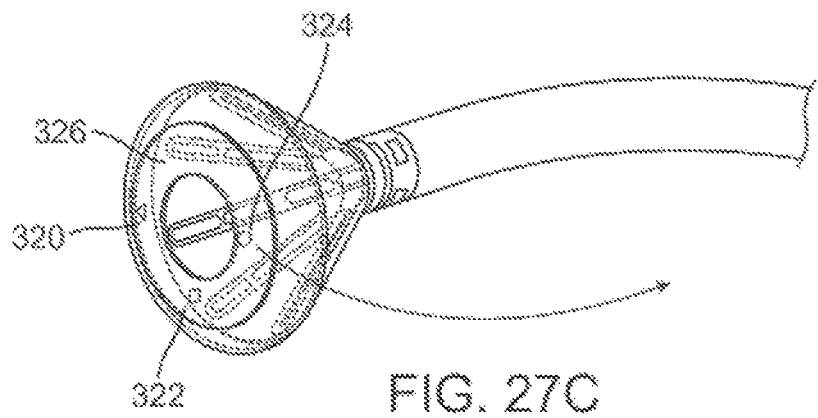
Figure 27B:
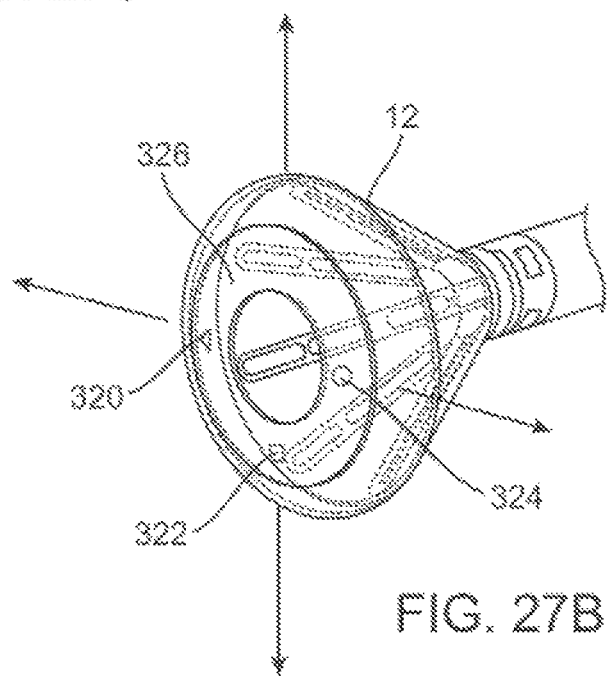

Another example of a steering assembly which may be utilized with the ablative visual electrode assembly is illustrated in the perspective view of FIG. 27A which illustrates hood 12 and deployment catheter 16 coupled to handle 210. Handle 210 may define one or more markings over the steering controls which correspond with identical or similar markings defined along the distal membrane of hood 12. For example, FIG. 27B illustrates a perspective detail view of hood 12 illustrating a first directional indicator 320 at a first location along hood 12, a second directional indicator 322 at a second location along hood 12, a third directional indicator 324 at a third location along hood 12, and a fourth directional indicator 326 along a fourth location along hood 12. Each directional indicator may be distinct from one another and may correspond to the indicators located on handle 210. As the user visualizes the tissue through hood 12, if the hood 12 needed to be repositioned in any particular direction along the tissue, the user may note the direction to be moved relative to the indicators marked on hood 12 and may thus manipulate the controls on handle 210 accordingly such that movement of the controls in the chosen direction may articulate the hood 12 in the same direction, as illustrated in FIG. 27C. Such a feature may be highly advantageous relative to the absence of visual markings as it may be difficult for the user to steer the hood 12 in a desired direction after it is inserted into the patient's body due to the changes in hood orientation relative to the handle 210 orientation.

Figure 28A:
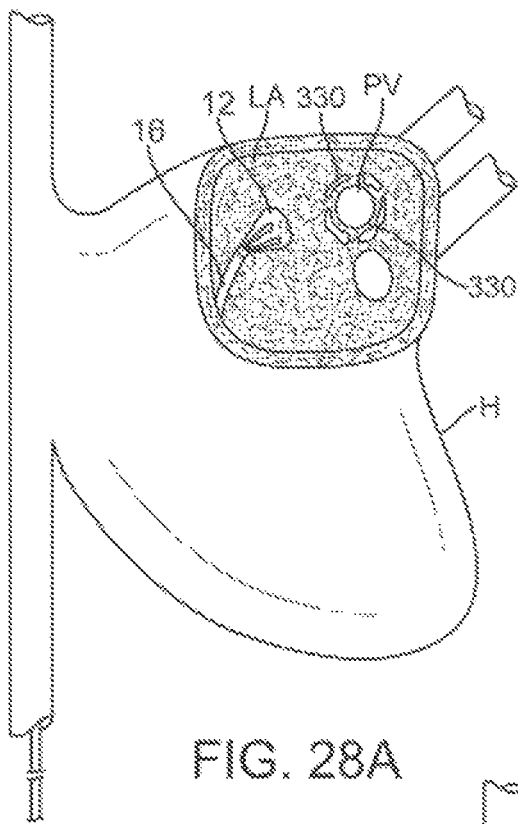
FIGS. 28A and 28B show cross sectional side views of the left atrium having discontiguous lesions formed about the pulmonary vein ostium and the imaging hood inspecting and further ablating.
Figure 28B:
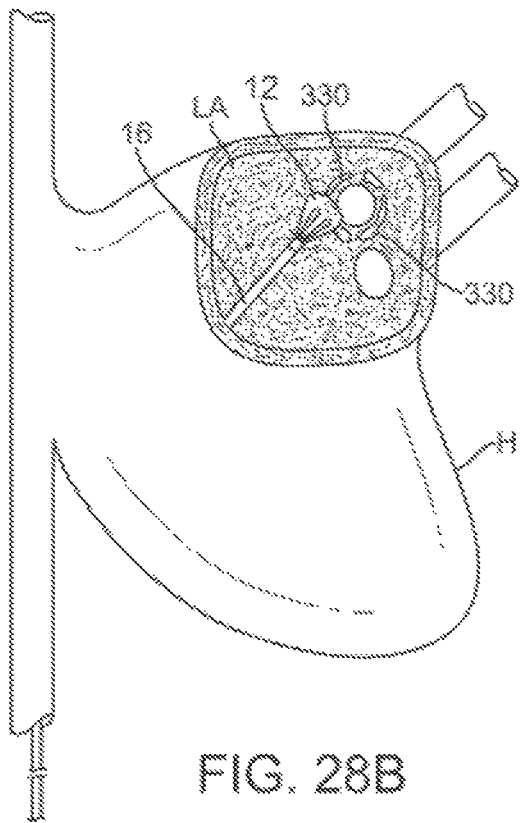
Figure 29:
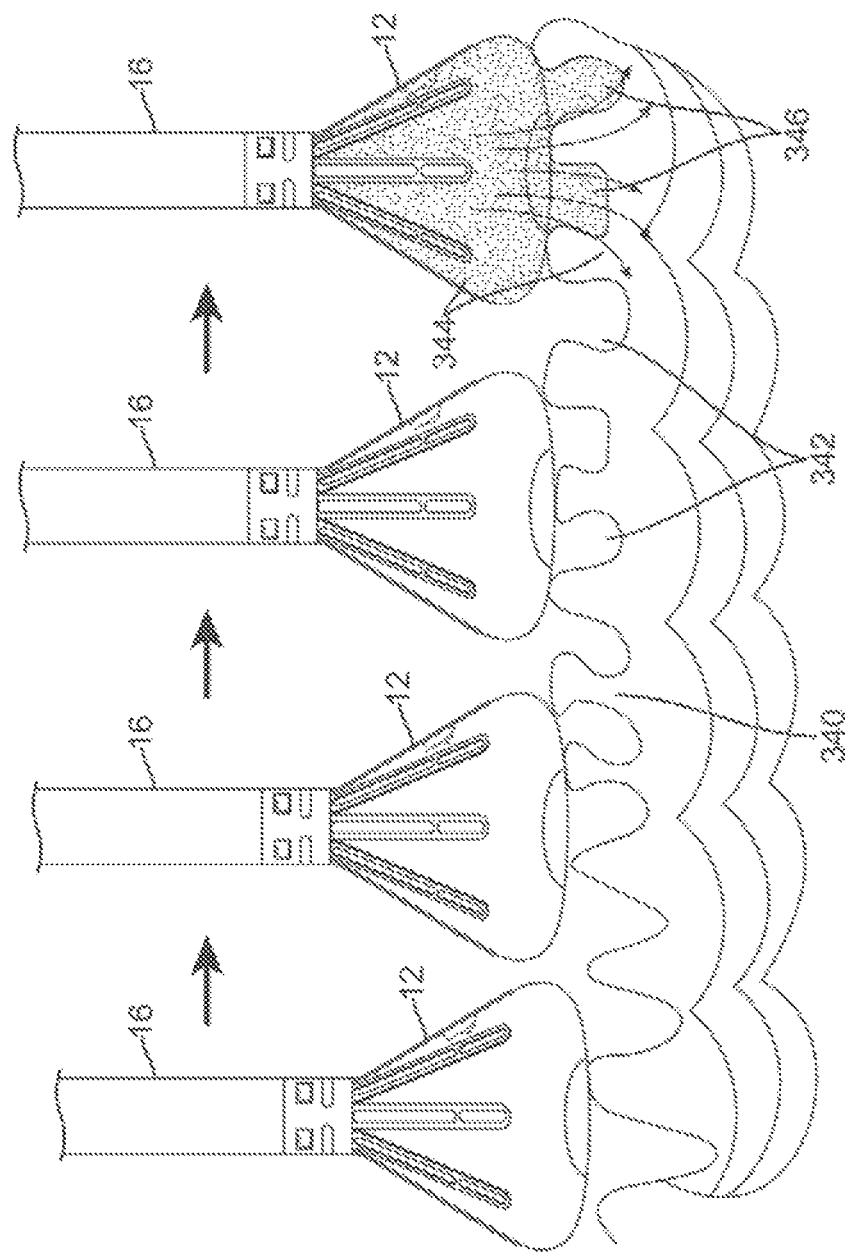
FIG. 29 illustrates an example of how the imaging hood may be positioned over trabeculated tissue for imaging and/or ablation treatment.
Figure 30:
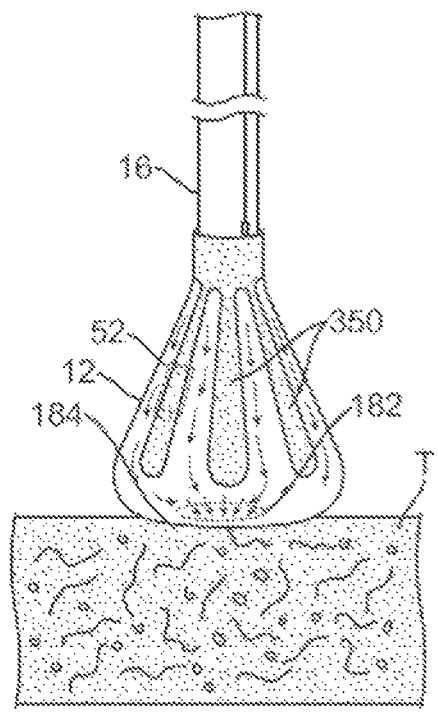
FIG. 30 shows a side view of another variation of imaging and treatment catheter with electrically conductive struts delivering energy to the underlying tissue.

Once the hood 12 has been desirably positioned within the chamber, such as the left atrium LA as shown in the partial cross-sectional view of the heart H in FIG. 28A, hood 12 may be articulated utilizing any of the mechanisms and methods described herein to be placed against tissue such as the ostia of the pulmonary veins PV for visualization and/or treatment. A number of lesions 330 may thus be formed about the pulmonary vein PV ostium either continuously such that each lesion formed overlaps an adjacent lesion to aggregately form a continuously-adjoined lesion or a number of discontiguous lesions may be formed adjacent to one another. Hood 12 may be articulated to visually inspect lesions which may have been formed previously in prior treatments for locating discontiguities or gaps between adjacent lesions. Once identified, the visual electrode may be activated to close any gaps by ablating the underlying tissue visualized to form a contiguous lesion upon the tissue, as shown in the partial cross-sectional view of FIG. 28B. This process can be repeated until a contiguous lesion is formed on the desired pulmonary vein ostium, e.g., so as to isolate electrical signals from propagating from the pulmonary vein PV to the left atrium LA. Such methods may be used to treat conditions for cardiac arrhythmia such as atrial fibrillation, ventricular tachycardia, etc.

In positioning hood 12 against the tissue surface to be visualized and/or ablated, the surface anatomy may present an uneven surface which may generally inhibit the formation of a sufficient seal between the hood aperture and tissue. An example may include trabeculated tissue surfaces 340 which define a number of tissue folds 342. As illustrated in the partial cross-sectional side view of FIG. 29, hood 12 may still form a sufficient seal against the tissue surface by repositioning the hood 12 over the trabeculated tissue surface 340 at a location where the purging fluid 344 introduced into hood 12 is able to temporarily fill the underlying folds 342 such that the fluid is retained 346 within the folds. In this manner, visualization may be accomplished and ablation energy may be transmitted through the fluid 344 and into the underlying trabeculated tissue.

Rather than utilizing a separate ablation electrode positioned through deployment catheter 16 and within hood 12, one or more of the support struts which may be embedded in the architecture of hood 12 may be utilized as a discharging ablation electrode. An example is illustrated in the side view of FIG. 30, which shows hood 12 having a number of support struts 350 extending distally along or within membrane of hood 12. One or more of the support struts 350 may be fabricated from electrically conductive materials or coated with electrically conductive materials such as copper, stainless steel, Nitinol, silver, gold, platinum, etc. An insulated electrical wire through deployment catheter 16 may be, electrically connected to the one or more electrically conductive support struts 350 along the hood 12. In some variations, the conductive support struts 350 may be exposed internally within the hood 12 while exteriorly of hood 12, the support struts 350 may be covered by the membrane (or wall) of hood 12 such that they are not in contact with fluids, tissue, or bodies outside the hood 12. Additionally, because this particular configuration does not require the use of a separate ablative electrode, the availability of space through the deployment catheter 16 is increased allowing for the insertion of additional instruments. Functionally, with the ablative energy activated, the electrical current may be discharged along the one or more conductive support struts 350 and through the purging fluid and into the underlying tissue exposed through aperture 182.

Figure 31:
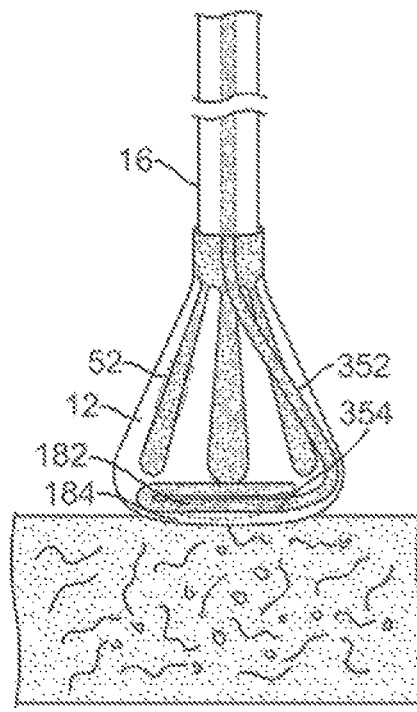
FIG. 31 shows a side view of another variation of the imaging and treatment catheter with an energy delivery ring electrode proximal to the hood aperture.

Another variation is shown in the side view of FIG. 31, which illustrates hood 12 having an energizable ring electrode 352 extending from a ring electrode support 354 and positioned within hood 12 in proximity to aperture 182. The energy delivery portion of ring electrode 352 may be confined to the ringed portion by insulation along support 354. Moreover, as support 354 is moved proximally or distally within hood 12 relative to aperture 182, the distance between ring electrode 352 and aperture 182 may be controlled to alter the ablative characteristics upon the underlying tissue through the aperture 182. Additionally, having the circular configuration around the aperture 182 of the hood 12 may also increase the efficiency of the ablation process as ablation energy is efficiently delivered to the ablation area.

Yet another variation is illustrated in the partial cross-sectional side and perspective views of FIGS. 32A and 32B, respectively, which show an energizable ring electrode 360 coated or placed directly upon the membrane of hood 12. Ring electrode 360 may be placed directly upon the membrane utilizing various techniques (e.g., sputter coating, chemical vapor deposition, etc.) where a layer of conductive material is sprayed or laid upon a mask and the underlying hood material to create the ringed structure. Electrode 360 may be connected electrically via a wire which passes along an interior surface of hood 12 and through deployment catheter 16. This particular variation illustrates ring electrode 360 formed upon an inner surface of membrane 184 within hood 12 adjacent to aperture 182. In other variations, ring electrode 360 may be formed along other locations within hood 12 along membrane 184 or further proximally along an inner surface of hood 12.

In any event, once the purging fluid is introduced into hood 12 and the underlying tissue T is visualized, ring electrode 360 may be energized resulting in a uniform dispersion of the energy 362 through the visualization fluid within hood 12 and into the underlying tissue T for ablative treatment. Additionally, ring electrode 360 may further provide structural rigidity to hood 12 and inhibit the hood membrane from folding undesirably. The sputter coated ring electrode 360 may have a thickness ranging anywhere from 0.1 to 5 micrometers and the width of the electrode 360 may be varied as so desired depending upon the ablative effects and energy discharge.

FIGS. 33A and 33B show partial cross-sectional side and perspective views, respectively, of yet another variation where the ring electrode 360 may be configured as a bipolar electrode assembly. As illustrated, with ring electrode 360 placed upon an inner surface of membrane 184 adjacent to aperture 182, a return electrode 364 may be similarly situated upon an exterior surface of membrane 184 such that the purging fluid introduced within hood 12 may be charged by ring electrode 360 and directed out of aperture 182 and towards return electrode 364 located on an external surface of membrane 184 in contact against the underlying tissue T such that the energy 362 may effectively ablate the tissue.

Figure 34A:
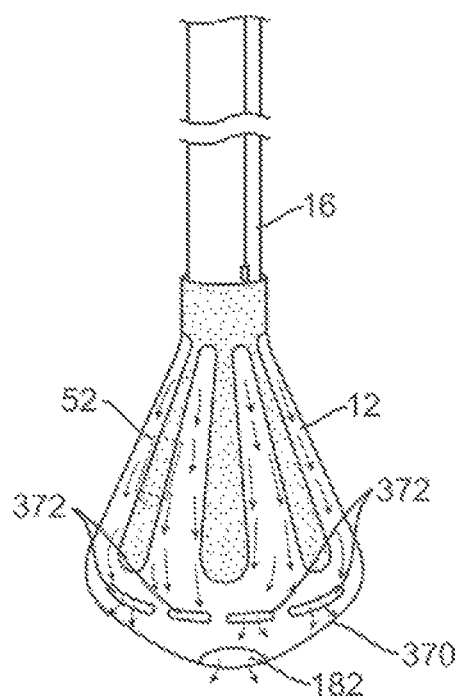
FIGS. 34A and 34B show side views of another variation of an imaging hood having a tapered distal membrane which defines one or several additional apertures for selective tissue ablation therethrough.
Figure 34B:
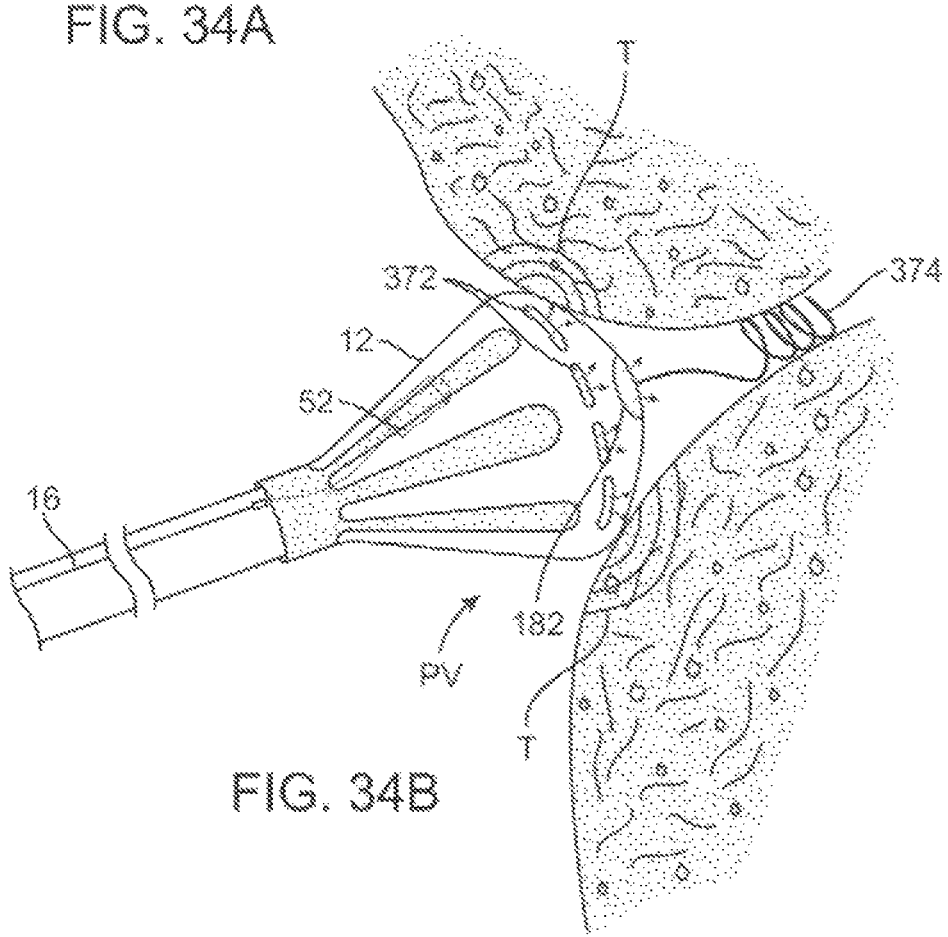

Aside from variations in the electrode structure or configuration, the hood and distal membrane may also be configured in alternative ways to change the ablative characteristics of the assembly. For instance, FIGS. 34A and 34B show side views of a variation of a visual electrode assembly where hood 12 may have an extendable membrane 370 disposed over hood 12 such that a distally extending conical or diamond shape configuration is formed when hood 12 is filled with saline fluid. The variation illustrated has multiple purging ports 372 defined circumferentially over extendable membrane 370 proximally of aperture 182 and may function as side irrigation channels for the saline fluid to purge blood out of hood 12 during visualization. Because the distally extending membrane 370 forms a tapered surface, this particular variation may be suited for contacting tissue surfaces at an angle, such as the ostium surrounding an opening of a pulmonary vein PV, as illustrated in FIG. 34B. The purging ports 372 may thus directly contact the underlying ostium and ablate the tissue directly through purging ports 372.

Direct visualization and inspection of the pulmonary vein ostium can be performed through hood 12 and ablation under direct visualization can be subsequently performed on the ostium through the ports 372 upon the exposed tissue of the ostium. Contiguous lesions can be formed by repeating the process and rotating the hood 12 along the longitudinal axis to reposition the visual electrode side ports 372 to surfaces that are un-ablated. An optional anchoring member 374, such as a helical anchor, may be deployed from deployment catheter 16, through aperture 182, and into the pulmonary vein PV where it may be deployed for temporarily securing itself against the vessel walls during visualization and/or ablation. Other tools such as guidewires, needles, dilators, graspers, ablation probes, other pulmonary vein anchors, etc. may also be utilized.

In the case where tools need not be used, the central aperture 182 may be enclosed entirely and in the event when tools are needed to pass through the enclosed distal face of the hood 12, a needle can be used to puncture through the hood membrane and other tools may be advanced through the opening to access to the exterior area of the hood 12.

Although multiple purging ports 372 are illustrated, a single side opening may be used instead. In such a variation of the device, the visualization catheter may be rotated by the user to form continuous lesions around the ostium of the pulmonary vein PV. The user may be able to visualize the tissue undergoing ablation and rotate the hood 12 to ablate an adjacent tissue region accordingly.

Figure 35A:
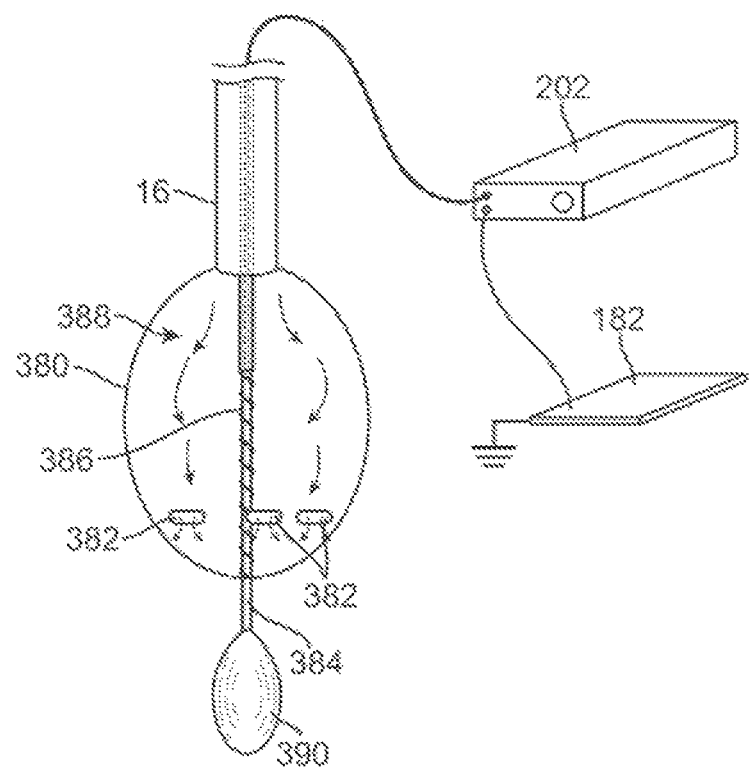
FIGS. 35A and 35B show side views of another variation of an imaging catheter configured as an expandable membrane having one or more apertures for selective tissue ablation therethrough.
Figure 35B:
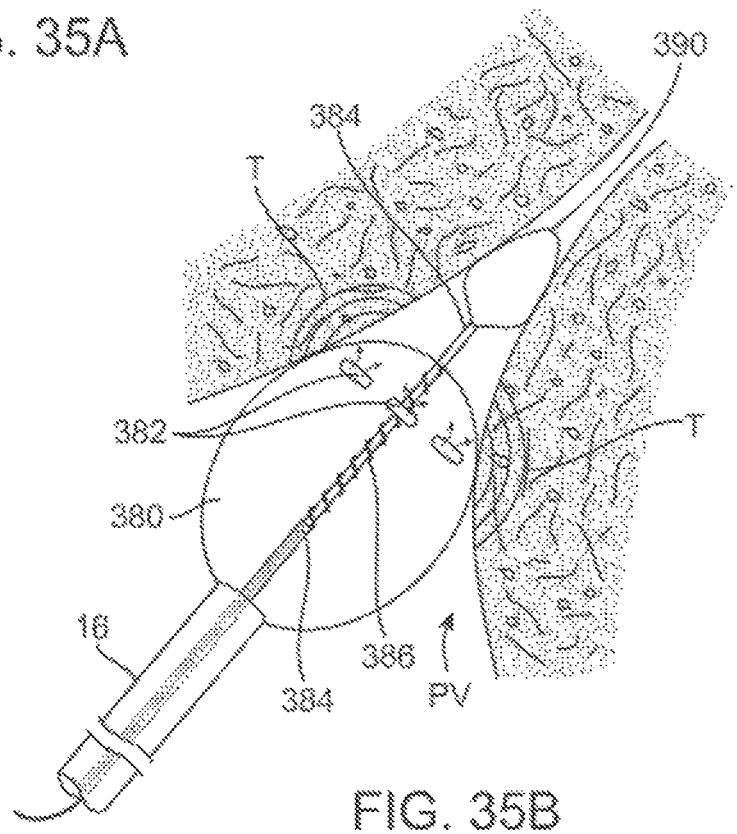

Another variation of an alternative hood structure is illustrated in the perspective and side views, respectively, of FIGS. 35A and 35B which show a visual electrode assembly which utilizes an expandable membrane 380 which is enclosed except for one or more side purging ports 382 through which the purging fluid 388 may escape. An electrode 386 may be positioned along a support member 384 which extends through membrane 380 and distally thereof. The electrode 386 may form a helical coil along the support member 384 and can terminate at the distal inner area of the membrane 380 to deliver ablation energy to areas in close proximity to the purging ports 382. Similar to the variation described above, because the surface of membrane 380 is tapered, the assembly may be particularly suited for positioning-against the ostium of a pulmonary vein PV so that ablation energy discharged from electrode 386 within membrane 380 may be directed through the purging fluid 388 escaping through the one or more purging ports 382 and into the tissue surrounding the ostium, as shown in FIG. 35B. A distal balloon anchor 390 may be positioned along a distal tip or portion of support member 384 for advancement into the pulmonary vein PV to provide temporary anchoring for the assembly.

Figure 36A:
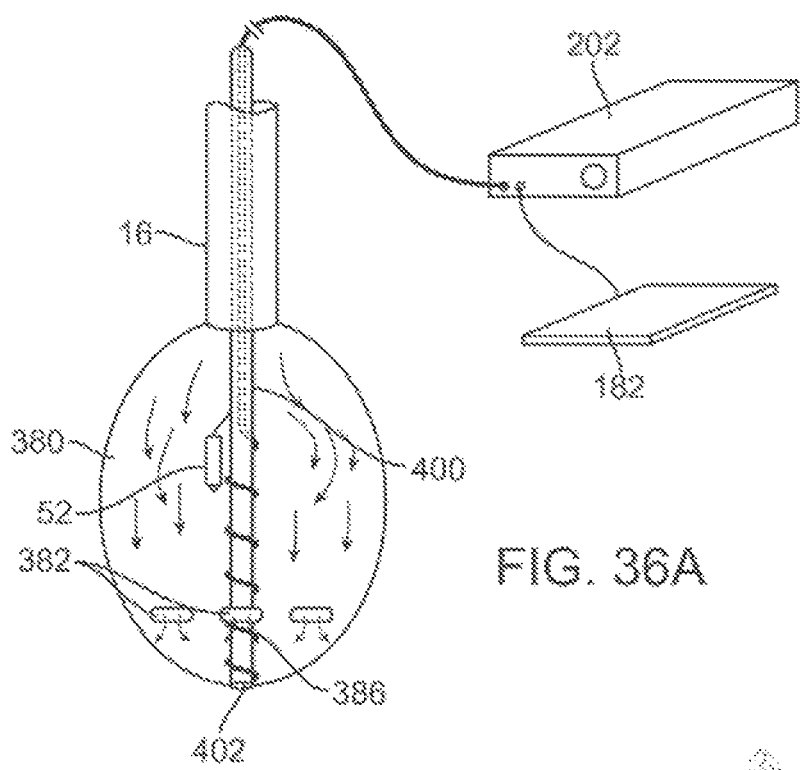
FIGS. 36A and 36B show side views of yet another variation of an imaging catheter with an expandable membrane having a lumen defined therethrough and one or more apertures for selective tissue ablation.
Figure 36B:
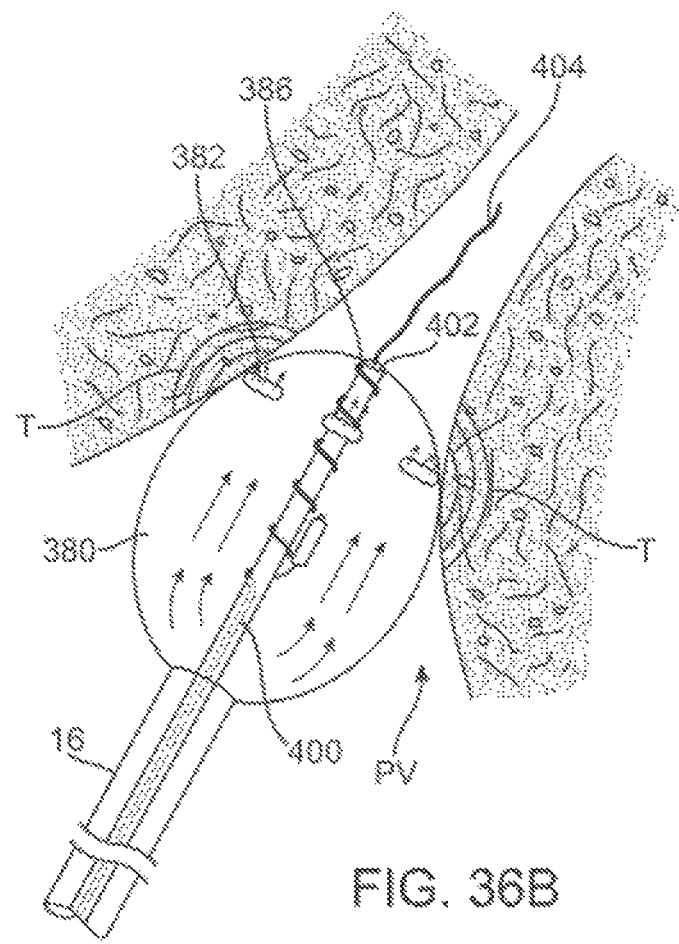

Similar to the variations above, FIGS. 36A and 36B illustrate perspective and side views, respectively, of another variation which utilizes an expandable membrane 380 and one or more purging ports 382 along a tapered membrane surface for positioning against an ostium of a vessel opening. This particular variation utilizes a support shaft 400 which defines a lumen opening 402 which opens at a distal end of expandable membrane 380. Imaging element 52 may be placed along support shaft 400 within membrane 380 and a number of various tools, such as guidewire 404, may be passed through shaft 400 and distally of lumen opening 402 for access into the pulmonary vein PV.

Figures 37A, 37B:
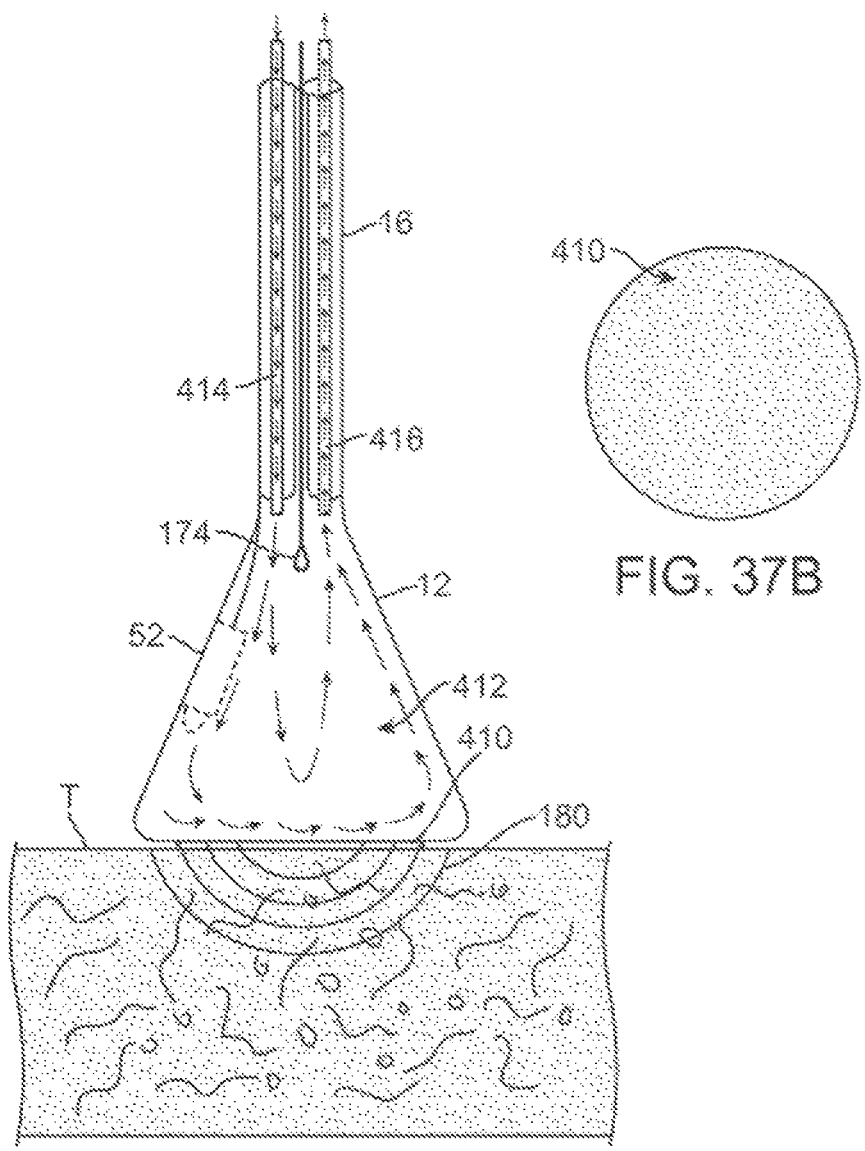
FIGS. 37A and 37B show side and end views, respectively, of an imaging catheter variation having a distal membrane defining a plurality of pores to facilitate purging fluid retention and circulation within the hood.

Another variation of a visual electrode ablation system is illustrated in the respective partial cross-sectional side and end views of FIGS. 37A and 37B. This particular variation may incorporate a distal membrane which defines a plurality of micro-pores or slots 410, illustrated in FIG. 37B. As the purging fluid is introduced within hood 12 via fluid lumen 414, the fluid may be recirculated 412 within hood 12 to provide cooling to the underlying tissue T contacted by the hood 12. The fluid 412 within hood 12 may be withdrawn from hood 12 via fluid return lumen 416. As the pressure of the fluid is increased within hood 12, the purging fluid may seep through the micro-pores or slots 410 and into contact with the underlying visualized tissue. The electrode, either via separate electrode 174 or via a conductive support strut, may be energized to transmit a current through this fluid and into the underlying tissue through the seeped fluid. The micro-pores or slots 410 may have a diameter ranging from, e.g., 50 to 500 micrometers. Moreover, with multiple irrigation channels, the circulating fluid 412 within the hood 12 may function to cool the ablated tissue surfaces and this additional cooling feature may facilitate the formation of deeper and relatively larger lesions.

Figure 38A:
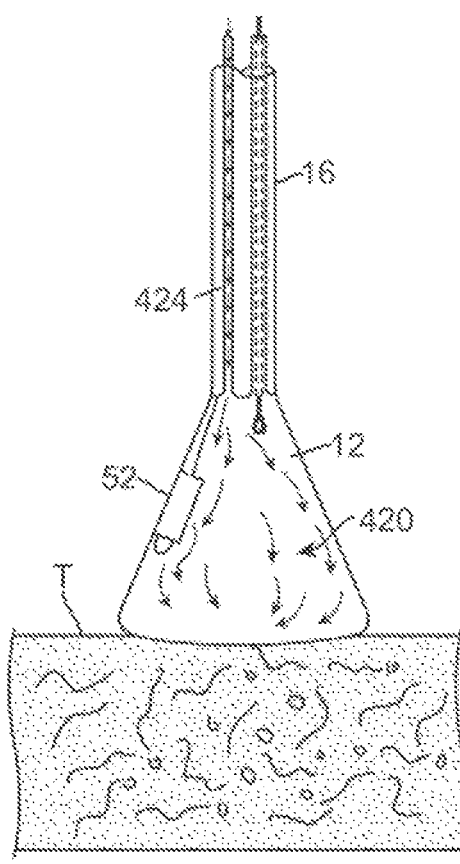
FIGS. 38A to 38C illustrate side views of an imaging catheter placed against a tissue surface and having a negative pressure created within the hood to isolate and ensure contact against the tissue region to be visualized and treated.
Figure 38C:
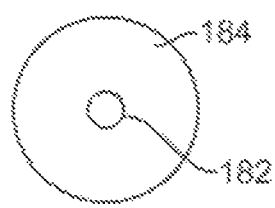
Figure 38B:
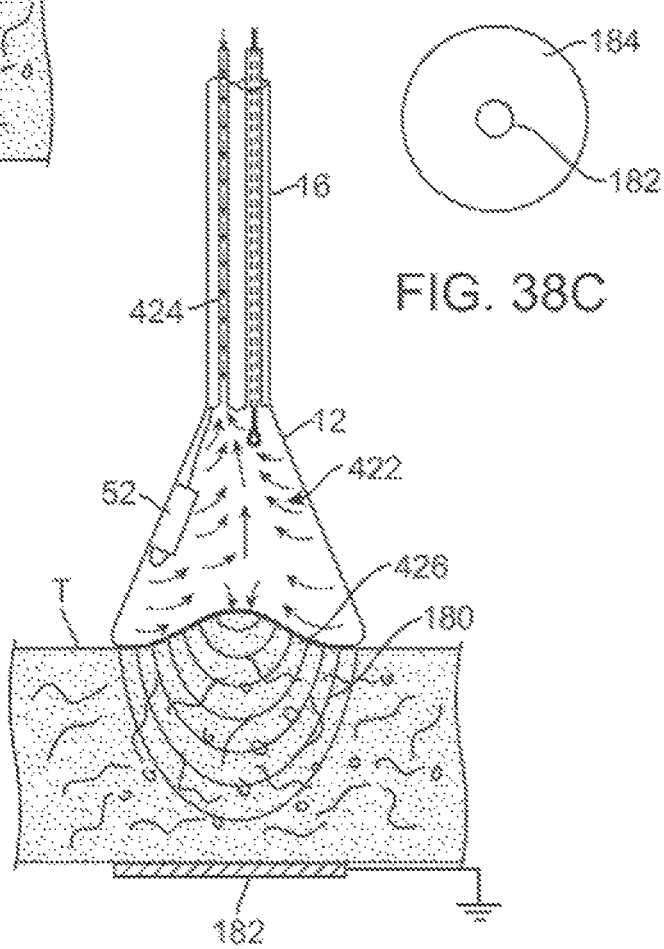

Another variation for improving the creation of lesions upon the underlying tissue is illustrated in the side and end views of FIGS. 38A to 38C. In this variation, hood 12 may be positioned against the tissue surface T and the interior of hood 12 may be filled with the purging fluid 420, as shown in FIG. 38A. Once the hood interior has been purged of any blood and visualization of the underlying tissue T is established, a negative pressure may be induced within hood 12 by withdrawing or suctioning 422 some of the purging fluid 420 proximally through infusion and/or suction lumen 424, as shown in FIG. 38B. The tissue in contact with the purging fluid through aperture 182 (shown in FIG. 38C) may be drawn against distal membrane 184 through aperture 182 by the negative pressure such that the adhered tissue 426 may become slightly elevated and partially drawn through aperture 182. With this seal created between the adhered tissue 426 through aperture 182, the tissue may be ablated while under visualization from imaging element 52 and an ablation area matching the aperture 182 area may be ensured. With the relative current density over the aperture 182, relatively deep and narrow lesions may be formed through the adhered tissue 426.

Figure 39A:
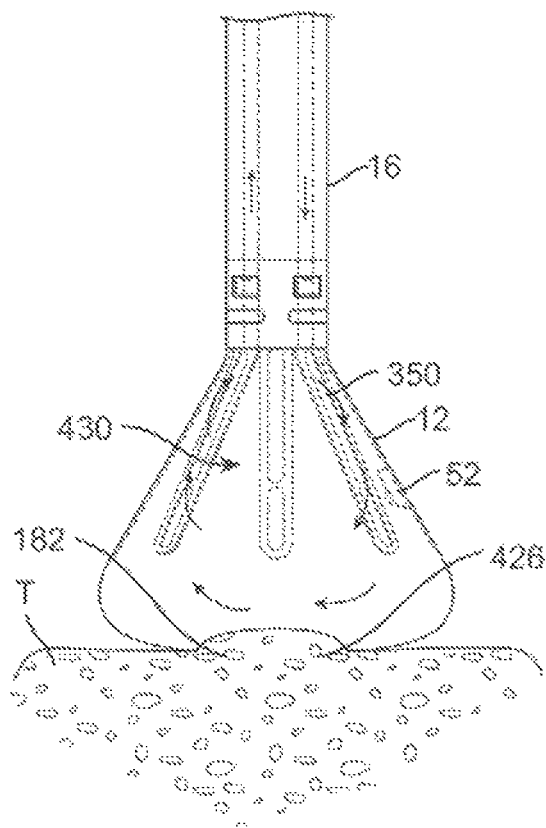
FIGS. 39A and 39B show side views of an imaging catheter positionable against a tissue surface and creating negative pressure within the hood to facilitate ablation via one or more electrically conductive struts along the hood.
Figure 39B:
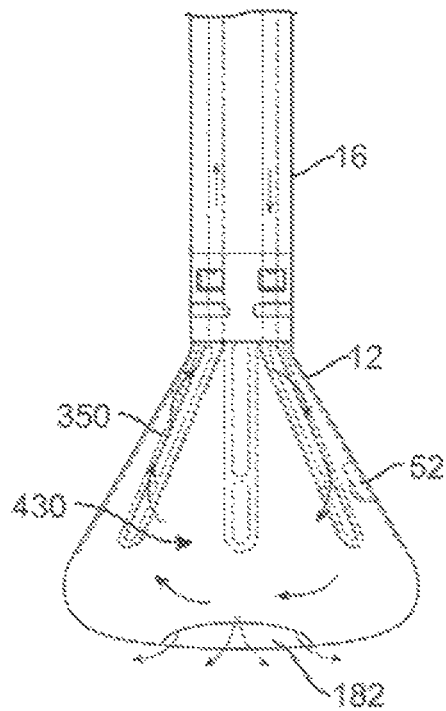

FIGS. 39A and 39B illustrate other variations of a hood 12 also configured for creating a negative pressure within the hood interior for creating a seal between the tissue and aperture 182. In this variation, the assembly may be configured to create a recirculating flow of fluid 430 within the hood interior once adhered to the tissue surface. As above, the hood interior may have the purging fluid introduced to clear the visualization field. With the infusion of the fluid into hood 12 at a first flow rate through a first lumen, the purging fluid may also be withdrawn from hood 12 at a second flow rate through a second lumen once the visualization field has been established. By maintaining the second flow rate for withdrawal at a relatively higher rate than the first flow rate for infusion into hood 12, an overall negative pressure may be maintained within hood 12 which may cause the underlying tissue 426 to become adhered against aperture 182, as illustrated in FIG. 39A, while a recirculating flow of fluid 430 is maintained within hood 12. This recirculating flow 430 may maintain a cooling effect upon the ablated tissue. Alternatively, by maintaining a first flow rate for infusion which is relatively higher than the second flow rate for withdrawal, a considerable amount of the purging fluid may be conserved as a result of efficiently purging the hood 12, as illustrated in FIG. 39B.

As the tissue is ablated during tissue treatments, the ability to directly and vividly visualize the ablation process without any ablation probe obstructing the visualization field may allow for visual monitoring of the ablation treatment, as illustrated in the view of the targeted tissue 440 as visible through aperture 182 along distal membrane 184 when viewed from within hood 12. For instance, heating of tissue may result in the formation of steam within the ablated tissue and micro-bubbles 442 on the tissue surface, which is indicative of a pending endocardial disruption. If an endocardial disruption occurs, the tissue may "pop" releasing tissue debris, e.g., charred tissue fragments, coagulated blood, etc., into the environment. Endocardial disruptions and the monitoring and clearing of tissue debris within hood 12 are described in further detail in U.S. patent application Ser. No. 11/775,819 filed Jul. 10, 2007, which is incorporated herein by reference in its entirety.

Figure 40A:
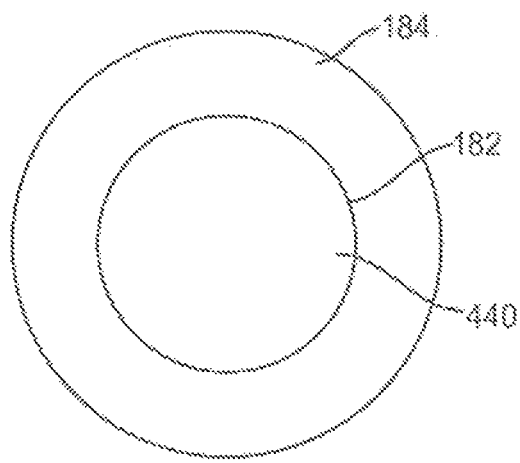
FIGS. 40A to 40C illustrate a view of the underlying tissue within the hood during an ablation procedure with bubble formation occurring upon the tissue surface.
Figure 40B:
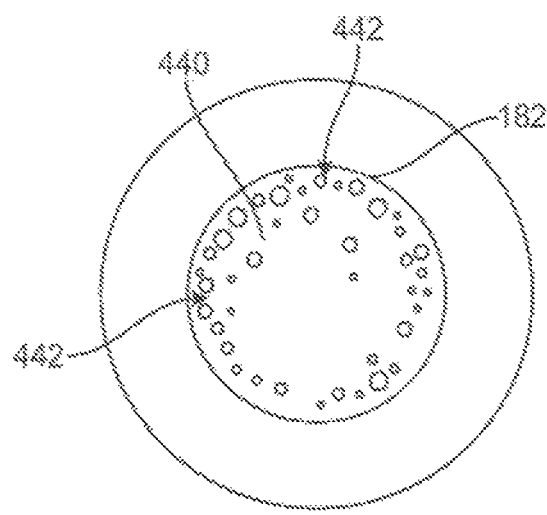
Figure 40C:
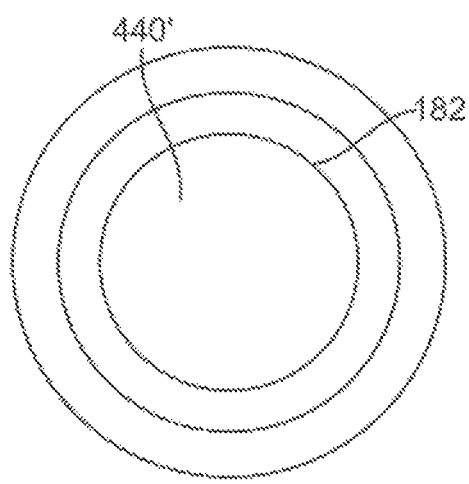
Figure 40D:
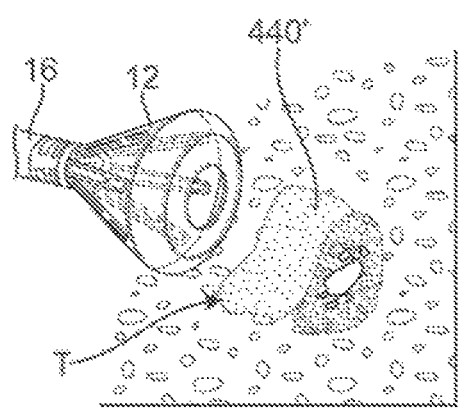
FIG. 40D illustrates a perspective view of the resultant lesion formed by ablating through the hood.

In this variation, as the visualized tissue is ablated through the purging fluid via a non-contacting electrode (e.g., separate electrode or conductive strut), the bubble formation 442 upon the tissue surface may be visually monitored directly and an algorithm may be employed for bubble detection which monitors the number and rate of bubble formation within the visualization field, as shown in FIG. 40B. Such an algorithm may accordingly pre-empt an endocardial disruption by automatically reducing or shutting down the power supplied to the electrode such that the underlying tissue is ablated without popping. The algorithm may run via a processor in an attached computer or within the visual imaging processor. The ablation may continue until the underlying tissue is blanched 440' which may serve as a visual indication of transmural tissue while avoiding the formation of any bubbles 442. With the ablation completed, hood 12 may be repositioned over another tissue region for treatment or removed from the region, as shown in the perspective view of FIG. 40D.

Figure 41:
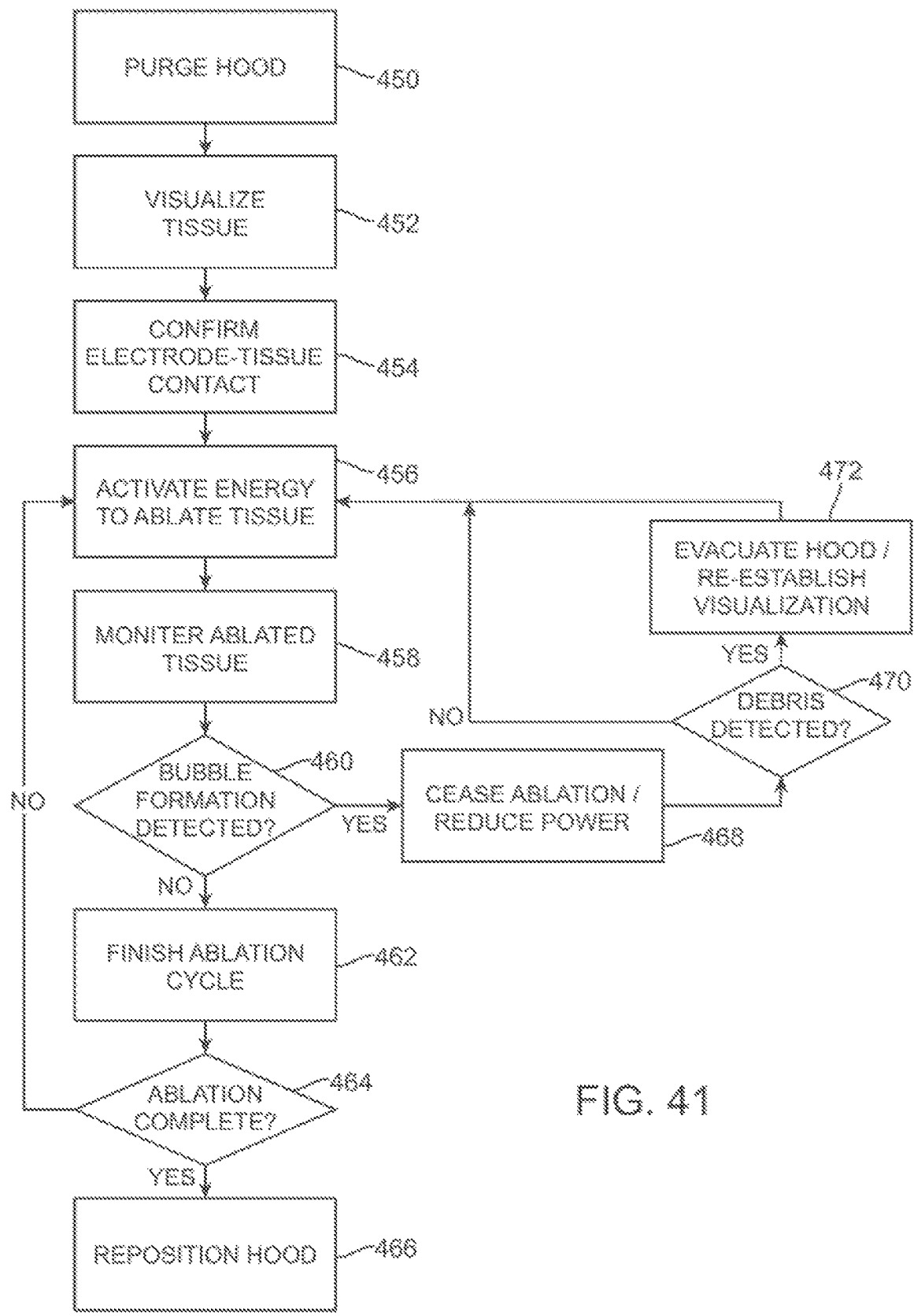
FIG. 41 shows a flowchart outlining an example of an algorithm for utilizing the visual detection of bubble formation upon the ablated tissue surface for preventing tissue eruptions.

FIG. 41 illustrates a flow chart of one example for an algorithm incorporated into software run by a processor in a computer or within the visual imaging processor which may be configured to monitor the quantity as well as the rate of bubble formation using technology such as the edge detection algorithms which are generally known in the art. In this example, once the hood, has been purged to clear the visualization field 450, the underlying tissue may be visualized 452. Electrode-to-tissue contact may be confirmed 454 by sending a test charge or by visually confirming the contact. The ablation energy may then be activated to ablate the tissue under visualization 456. While ablating the tissue, the tissue surface may be visually monitored 458 by the edge detection software. If no bubbles are visually detected within the field 460, the ablation cycle time may be finished 462 and the tissue may be evaluated 464 to determine whether sufficient lesion formation has been achieved. If further tissue ablation is required, then the ablation energy may again be activated 456 and the process repeated until sufficient lesion formation has been achieved. The hood 12 may then be repositioned 466 upon a second tissue region for treatment or the hood 12 may be removed from the area.

If during the ablation treatment, the software detects the formation of bubbles 460, the software may be configured to automatically cease ablation or reduce the power supplied to the electrode 468. Alternatively, the software may instead be configured to notify the user by an alarm and the user may then directly cease ablation or reduce power accordingly. In either case, with the power ceased or reduced, the software may be further configured to detect any debris which may have been released from the tissue by a disruption or the user may simply examine the visual field for any presence of debris 470 within the field. If no tissue debris is detected, ablation may resume 456 and the process continued. However, if tissue debris is detected, hood 12 may effectively enclose and contain the debris therewithin and the fluid and debris within hood 12 may be evacuated 472 through deployment catheter 16 either by the user or automatically by the processor upon detection of the debris. Once the hood 12 interior has been cleared, purging fluid may be re-introduced to re-establish the visualization field of the tissue being treated and ablation energy may again be activated 456 to continue the ablation process if so desired.

Figure 42:
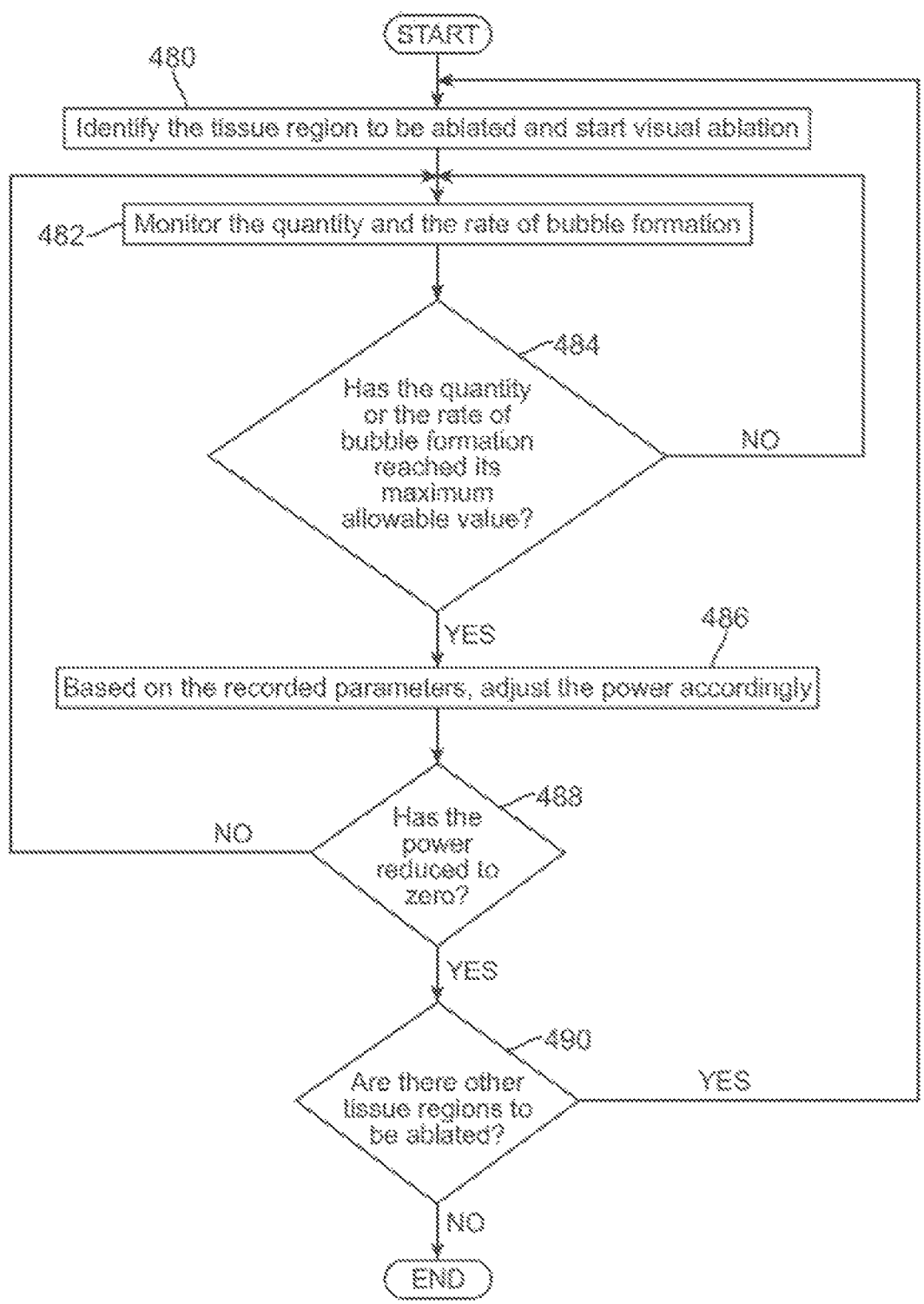
FIG. 42 shows another flowchart outlining an example of an algorithm for automatically reducing the ablation energy based upon bubble formation of the ablated tissue.

In reducing the power level or ceasing ablation altogether, FIG. 42 illustrates another example of an algorithm which may be used to adjust the power level accordingly. As above, once the hood 12 has been positioned upon the tissue to be treated and visualization established, ablation of the tissue may be initiated 480. The software may monitor the visualization field to detect the quantity and/or rate of bubble formation 482. If the quantity and/or rate of bubble formation have not exceeded a predetermined maximum allowable value, ablation may continue while being monitored. However, if the quantity and/or rate of bubble formation have exceeded the predetermined threshold value, the power level may be adjusted to be reduced 486 by a preset amount and ablation may be continued while monitoring the ablation process. If bubble formation is further detected at the lower power level and has again exceeded the predetermined value, the power level may again be lowered 486 and the process repeated until the power level has been reduced to zero 488. If the power has been shut down automatically, the user may make a determination as to whether other tissue regions are to be ablated 490, in which case hood 12 may be repositioned and the entire process repeated. If ablation is complete, hood 12 may then be removed from the area entirely.

Figure 43:
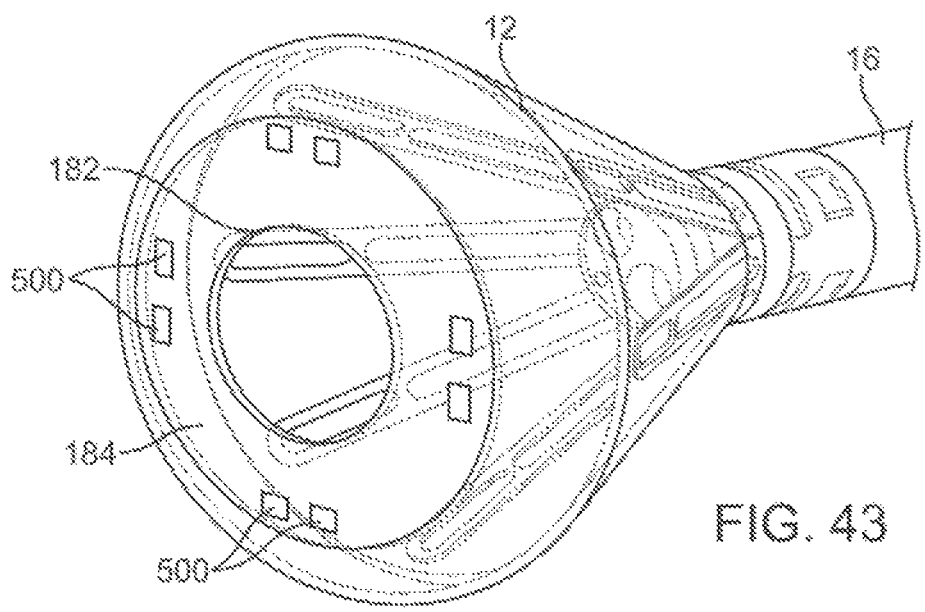
FIG. 43 shows a perspective view of a variation of the imaging hood with one or more electrocardiogram sensors disposed therealong for monitoring the ablated tissue.

Aside from visually monitoring and detecting for bubble formation, other assembly variations may additionally and/or alternatively incorporate other tissue monitoring features for use with ablation treatments for monitoring the underlying tissue before, during, and/or after an ablation treatment. An example is illustrated in the perspective view of FIG. 43, which shows hood 12 incorporating one or more electrocardiogram electrodes 500 placed upon distal membrane 184 for direct contact against the targeted tissue. Such electrocardiogram electrodes 500 may be positioned about membrane 184 and utilized for a combination of applications, such as electrode recording, pacing and ablation either simultaneously or sequentially separated by the desirable intervals of time, etc.

In other variations, in order to gain better contact with the tissue region during mapping or pacing procedures, hood 12 may incorporate at least one pair of support members 510 at the base of hood 12 within or upon distal membrane 184 on either or both sides of aperture 182 and which are biased to extend distally from hood 12 at an angle, as shown in the partial cross-sectional side view of FIG. 44A. Each support member 510 may contain an electrode assembly 512 having an electrode 514 distally positioned upon member 510, return electrode 516 proximally of electrode 514, and an optional third electrode 518 proximally of return electrode 516, as illustrated in the detail side view of FIG. 44C. When hood 12 is pressed against the tissue region T, because members 510 are biased to extend distally at an angle relative to hood 12, the electrodes 512 on members 510 may maintain proper contact with the tissue region T as shown in the partial cross-sectional side view of FIG. 44B. The hood 12 may therefore be easily pressed against the desired tissue region T to perform electrogram mapping, pacing, and other diagnostic or therapeutic procedures.

Figure 45:
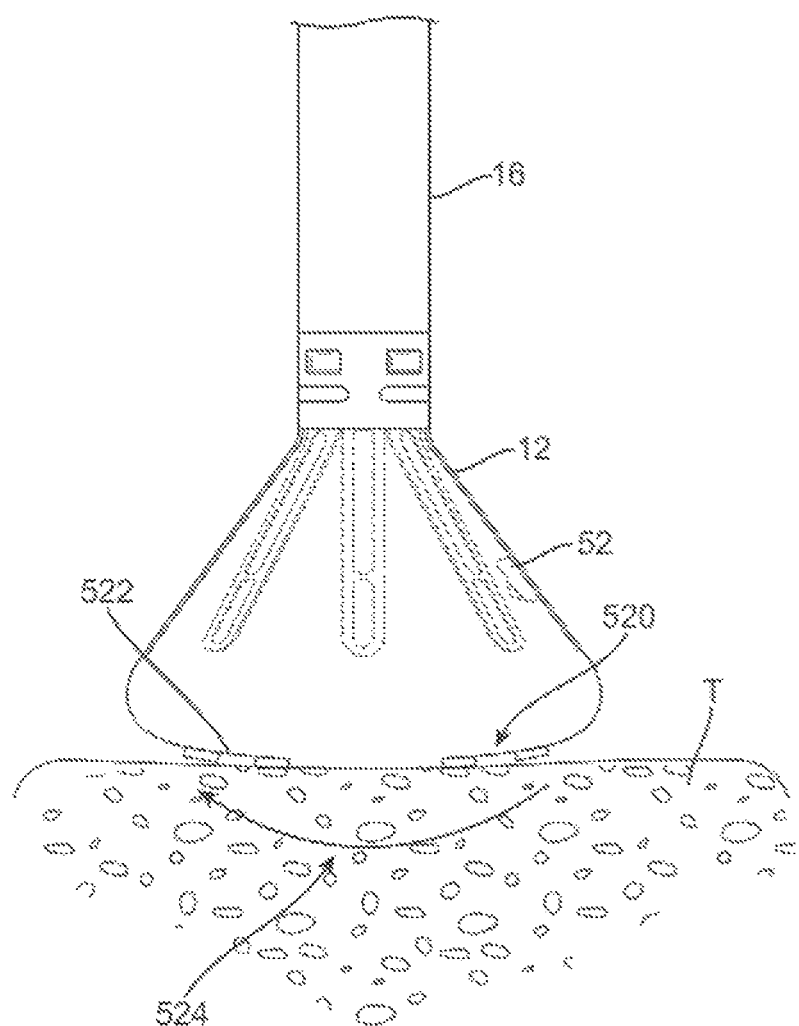
FIG. 45 shows a partial cross-sectional side view of another variation for detecting electrical activity of the underlying ablated tissue.

Another variation for monitoring the tissue before, during, or after an ablation procedure is illustrated in the partial cross-sectional side view of FIG. 45, which shows hood 12 positioned against a tissue surface T and having an electrode assembly 520 on a first side of the distal membrane over hood 12 and a return electrode assembly 522 on a second opposite side of the distal membrane over hood 12. The electrode assembly 520 may conduct measurement signals 524 to the return electrode assembly 522 through the underlying tissue and across the aperture where the treated tissue resides. The detected signals 524, or lack of received signals from electrode 520, by return electrode 522 may be used to determine a condition of the tissue region between the electrodes. If no signals are received by return electrode 522, this may bean indication that the ablated tissue is dead and hence does not allow conduction of electrical signals. This additional parameter may be utilized alone or in combination with the visual images of the treated tissue in determining whether the ablation has been thorough and complete.

Figure 46:
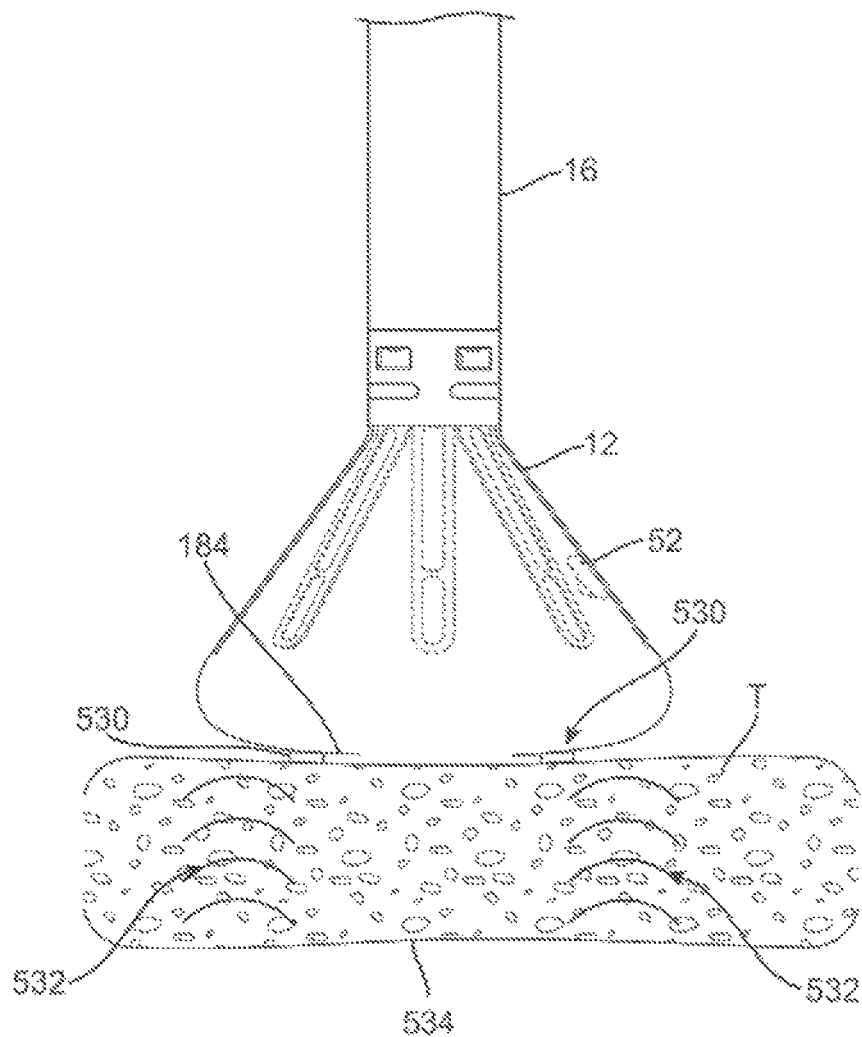
FIG. 46 shows a partial cross-sectional side view of another variation of the hood which incorporates one or more ultrasonic transducers for detecting a thickness of the underlying tissue for controlling the ablation energy.

Another variation is illustrated in the partial cross-sectional side view of FIG. 46, which shows hood 12 having one or more ultrasonic transducers 530 positioned upon hood 12 or distal membrane 184 in contact with the underlying tissue for determining a thickness of the tissue to be ablated. For example, prior to the initiation of tissue ablation, the one or more transducers 530 may be placed against the tissue surface to be treated and ultrasonic signals may be emitted into the tissue. The emitted signals may be reflected by any underlying obstructions or tissue interfaces 534 such that the return signals 532 received by the transducer or receiver may be automatically processed by software to analyze the return signals 532 for peaks of the ultrasonic waves received and the time intervals between them to determine a thickness of the underlying tissue. The thickness of the underlying tissue may be used to identify and confirm certain anatomical structures, such as the fossa ovalis, prior to transseptal puncturing or it may be used to assist the user in selecting a suitable power level and purging fluid flow rate in efficiently creating a lesion. The ultrasound transducers 530 can also be used to detect a distance between the hood 12 and the tissue during catheter manipulation. Before the hood 12 establishes visualization of the underlying tissue, the visual image through the hood 12 may appear red in color from, e.g., the surrounding blood environment, and the operator may not know if the hood 12 is relatively far from the tissue surface or if the hood is adjacent to the tissue surface yet is lacking a sufficient seal around the aperture or hood diameter. The ultrasound transducers 530 may thus be activated to provide this positional information to the user.

Yet another variation for monitoring the tissue for ablation treatment is illustrated in the side and perspective views, respectively, of FIGS. 47A and 47B. This variation utilizes one or more thermochromic indicators along the hood 12 or distal membrane 184 which are visible to the user through the visualization field for monitoring temperature changes in either or both of the underlying tissue or the purging fluid itself. As thermochromic materials undergo color changes indicative of the surrounding temperature, the changes in color of these indicators may be correlated to the temperature changes, either visually by the user or automatically by a software algorithm.

In the examples shown, a first thermochromic indicator 540 may be positioned along the exterior of membrane 184 for contact against the underlying tissue. The color changes in first indicator 540 may be viewed and detected through the distal membrane 184. Additionally and/or alternatively, a second thermochromic indicator 542 may be positioned along the interior of membrane 184 or along an inner surface of hood 12 to monitor temperature changes within the purging fluid itself. Examples of the color change in an indicator 542 are shown in the end views of FIGS. 48A to 48D. As illustrated, a first color of indicator 542' may be indicative of a first temperature level of the fluid within hood 12. As ablation treatment progresses and the fluid temperature rises within hood 12, indicator may change to a second color 542'' indicative of a second higher temperature level, and to a third color 542''' indicative of a third higher temperature level, and to yet a fourth color 542'''' indicative of still a fourth higher temperature level, and so on. In this manner, temperature levels may be monitored visually.

Figure 49:
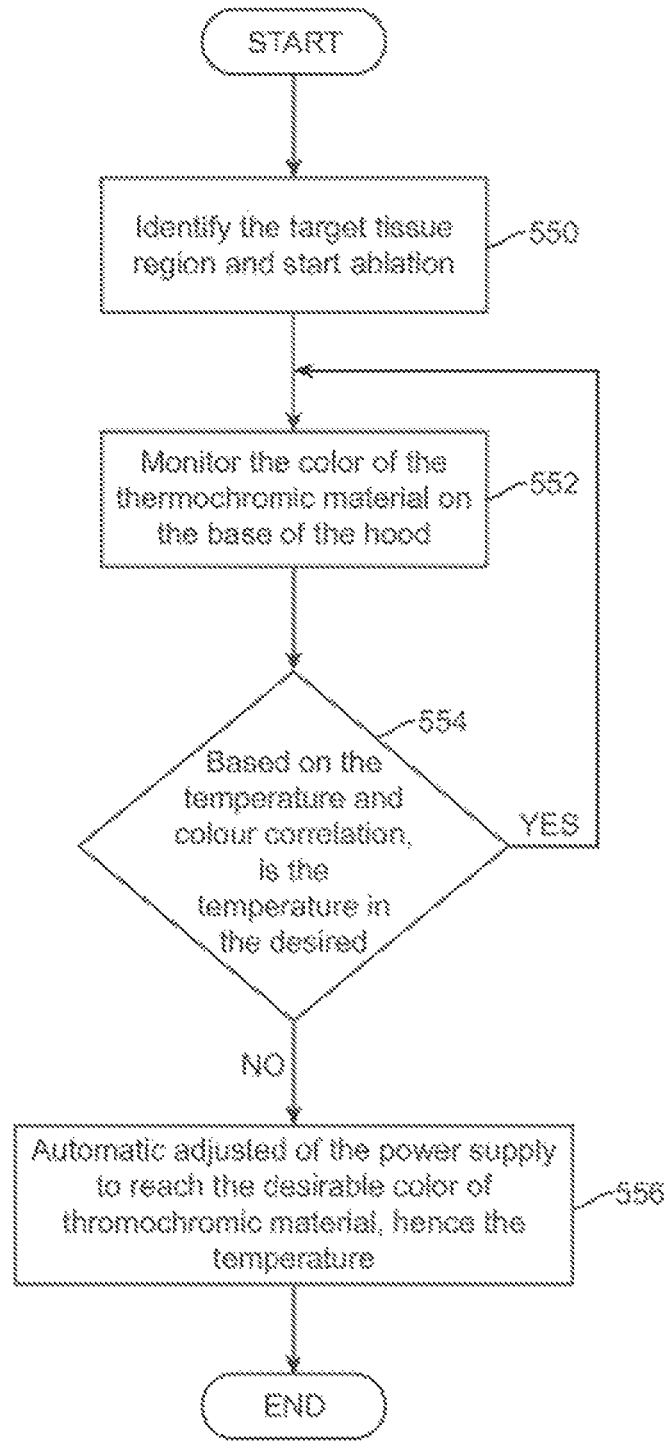
FIG. 49 shows a flowchart of an example for adjusting the ablation energy based upon the indicated temperature change of the thermochromic indicator.

An algorithm may be employed to correlate the observed color of the thermochromic indicator to a corresponding temperature of the region surrounding the thermochromic indicator. An automated software program employing the algorithm may be used to automatically detect the color of the thermochromic indicator and calculate the corresponding temperature and display it to the user. An automatic system may be used to regulate or switch off the power supplied to the purging fluid if the calculated temperature is close to exceeding the safe temperature limit. The example of FIG. 49 illustrates a flowchart where once the target tissue has been visually identified, ablation may proceed 550. The color the thermochromic indicator may accordingly be monitored 552 and based upon the color and correlated temperature level, a determination may be made as to whether the temperature is in a desirable range 554. If so, then the ablation may proceed while any color changes and correlated temperature are monitored. If the temperature has exceeded the desirable range 554, then the power supply may be automatically adjusted or lowered until a desirable color of the thermochromic indicator, and hence the temperature, has dropped below that level 556.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

The invention claimed is:

1. A method of ablating a tissue region within a blood-filled environment, comprising:
   restraining, with a hood, a fluid within a visualization field in a portion of the blood-filled environment, the hood having a plurality of support members extending from a base of the hood to bias the hood to a conical shape;
   injecting the fluid into the hood while extracting the fluid from the hood such that a rate at which the fluid is being injected is different than a rate at which the fluid is extracted;
   visualizing the tissue region through the fluid within the visualization field;
   forming a seal between the tissue region and an aperture of a distal membrane at a distal end of the hood such that the tissue region is pulled through the aperture proximally past the distal membrane; and
   while the aperture is sealed to the tissue region, with an electrode assembly positioned upon the support members, transmitting ablating electrical energy through the aperture, the aperture having a diameter that is less than an outer diameter of the distal membrane, the electrical energy being transmitted from the fluid into the visualized tissue region.

2. The method of claim 1 wherein the tissue region comprises a target tissue surface region within a chamber of a heart, wherein the target tissue surface region is visualized during ablation and while the heart is beating, and further comprising:
   expanding the hood from an insertion configuration to a deployed configuration within the chamber of the heart; and
   positioning the aperture in alignment with the target tissue surface region so that fluid is exposed to the tissue region and so that the ablating mitigates an arrhythmia of the heart.

3. The method of claim 2 wherein positioning comprises intravascularly advancing the hood into a chamber of a heart.

4. The method of claim 1 further comprising monitoring a change in color of the tissue region whereby a blanched color is indicative of lesion formation.

5. The method of claim 1 further comprising monitoring the tissue region for formation of bubbles.

6. The method of claim 5 further comprising monitoring a quantity and/or rate of bubble formation.

7. The method of claim 6 further comprising automatically adjusting a power level of the electrical energy based upon the quantity and/or rate of bubble formation.

8. The method of claim 1 wherein visualizing comprises inspecting the tissue region for discontiguous lesion formations.

9. The method of claim 8 wherein transmitting comprises transmitting electrical energy through an aperture along one or more gaps between discontiguous lesions.

10. The method of claim 1 further comprising monitoring a thermochromic indicator positioned upon the hood for changes in temperature.

11. The method of claim 10 further comprising adjusting a power level of the electrical energy based upon the changes in temperature.

12. The method of claim 1 wherein restraining comprises creating a negative pressure within the visualization field such that the tissue region is adhered to the aperture.

13. The method of claim 12 further comprising recirculating the fluid within the visualization field.

14. The method of claim 1, wherein the rate at which the fluid is injected is greater than the rate at which the fluid is extracted.

15. The method of claim 1, wherein the rate at which the fluid is injected is less than the rate at which the fluid is extracted.

16. A method of ablating a target tissue region, the target tissue region being disposed along a tissue surface, the method comprising:
- restraining a conductive fluid within a hood, the hood comprising a distal membrane, the distal membrane comprising an aperture having a diameter that is less than an outer diameter of the distal membrane, the hood having a plurality of support members extending from a base of the hood to bias the hood to a conical shape;
- using negative pressure of a purging fluid, forming a seal between the tissue region and the aperture such that the tissue region is pulled through the aperture proximally past the distal membrane; and
- while the aperture is sealed to the tissue region, with an electrode assembly positioned upon the support members, selectively directing ablating energy through the purging fluid into the target tissue region through the aperture and through the tissue surface while imaging the tissue surface along the target tissue region.

* * * * *